US011566258B2

(12) United States Patent
Periyannan et al.

(10) Patent No.: US 11,566,258 B2
(45) Date of Patent: Jan. 31, 2023

(54) STEM RUST RESISTANCE GENE

(71) Applicant: Commonwealth Scientific and Industrial Research Organisation, Acton (AU)

(72) Inventors: Sambasivam Kuppusamy Periyannan, Turner (AU); Peter Norman Dodds, Aranda (AU); Rohit Mago, Acton (AU); Evans Lagudah, Ngunnawal (AU)

(73) Assignee: Commonwealth Scientific and Industrial Research Organisation, Acton (AU)

( * ) Notice: Subject to any disclaimer, the term of this patent is extended or adjusted under 35 U.S.C. 154(b) by 608 days.

(21) Appl. No.: 15/779,782

(22) PCT Filed: Nov. 21, 2016

(86) PCT No.: PCT/AU2016/051131
§ 371 (c)(1),
(2) Date: May 29, 2018

(87) PCT Pub. No.: WO2017/091847
PCT Pub. Date: Jun. 8, 2017

(65) Prior Publication Data
US 2020/0270627 A1 Aug. 27, 2020

(30) Foreign Application Priority Data
Dec. 1, 2015 (AU) ................ 2015904976

(51) Int. Cl.
*C12N 15/82* (2006.01)
*A01H 1/02* (2006.01)
*A01H 1/04* (2006.01)
*C07K 14/415* (2006.01)
*A23K 10/30* (2016.01)
*A21D 2/38* (2006.01)

(52) U.S. Cl.
CPC ........... *C12N 15/8282* (2013.01); *A01H 1/02* (2013.01); *A01H 1/04* (2013.01); *C07K 14/415* (2013.01); *A21D 2/38* (2013.01); *A23K 10/30* (2016.05); *C07K 2319/00* (2013.01)

(58) Field of Classification Search
None
See application file for complete search history.

(56) References Cited

U.S. PATENT DOCUMENTS 8,889,957 B1 * 11/2014 Mason .................... A01H 5/10
800/312

FOREIGN PATENT DOCUMENTS

WO        2014194371    12/2014

OTHER PUBLICATIONS

RGA1d [*Aegilops taushii*], Aug. 16, 2013 (Year: 2013).*
Periyannan, The Gene Sr33, an ortholog of Barley Mia Genes, Encodes Resistance to Wheat Stem Rust Race Ug99, Science, Aug. 16, 2013 (Year: 2013).*
AU Examination Report, Application No. 2016363108, dated Nov. 2, 2021.
Meyers, Blake C., et al. (2003), "Genome-Wide Analysis of NBS-LRR-Encoding Genes in *Arabidopsis*", The Plant Cell, 15:809-834.
Eurasian Patent Application 201891314, Office Action and its English translation dated Jan. 30, 2020, 16 pages.
Mago, R., et at., "The wheat Sr50 gene reveals rich diversity at a cereal disease resistance locus.", Nature Plants, 2015, vol. 1, article 15186.
GenBank Accession No. KT725812, "Secale cereale RGA1-A gene, complete cds", Nov. 22, 2015, 3 pages.
Periyannan, S., et al., "The gene Sr33, an ortholog of barley Mla genes, encodes resistance to wheat stem rust race Ug99.", Science , 2013, 341(6147):786-788.
GenBank Accession No. AGQ17379.1, "RGA1b [*Aegilops tauschii*]", Jul. 14, 2013, 2 pages.
GenBank Accession No. KF031283.1, "Aegilops tauschii cultivar AUS18913 RGA1d gene, complete cds", Aug. 16, 2013, 2 pages.
Anugrahwati, D., et al., "Isolation o f wheat-rye IRS recombinants that break the linkage between the stem rust resistance gene SrR and secalin.", Genome, 2008, 51(5):341-349.
Seeholzer, S., et al., "Diversity at the Mla powdery mildew resistance locus from cultivated barley reveals sites o f positive selection." Molecular Plant-Microbe Interactions, 2010, 23(4):497-509.
GenBank Accession No. GU245948.1, "*Hordeum vulgare* subsp. *vulgare* cultivar RS170-10 x Piccolo A MLA25-1 mRNA, complete cds", May 5, 2010, 2 pages.
Cesari, S., et al., "Cytosolic activation o f cell death and stem rust resistance by cereal MLA-family CC-NLR proteins.", Proceedings of the National Academy of Sciences, 2016, 113(36):10204-10209.
Ukrainian Patent Application a201807258, Office Action and its English translation dated Nov. 15, 2021, 19 pages.
Response to AU Examination Report, Application No. 2016363108, dated Aug. 19, 2022, 12 pages.

* cited by examiner

*Primary Examiner* — Weihua Fan
*Assistant Examiner* — Brian James Sullivan
(74) *Attorney, Agent, or Firm* — Carol L. Francis; Rudy J. Ng; Bozicevic, Field & Francis, LLP

(57) ABSTRACT

The present invention relates to a transgenic plant which integrated into its genome an exogenous polynucleotide encoding a polypeptide which confers resistance to one or more races of *Puccinia graminis* f. sp. *tritici*, such as the Ug99 group of races *Puccinia graminis* f. sp. *tritici*.

Figure 1:
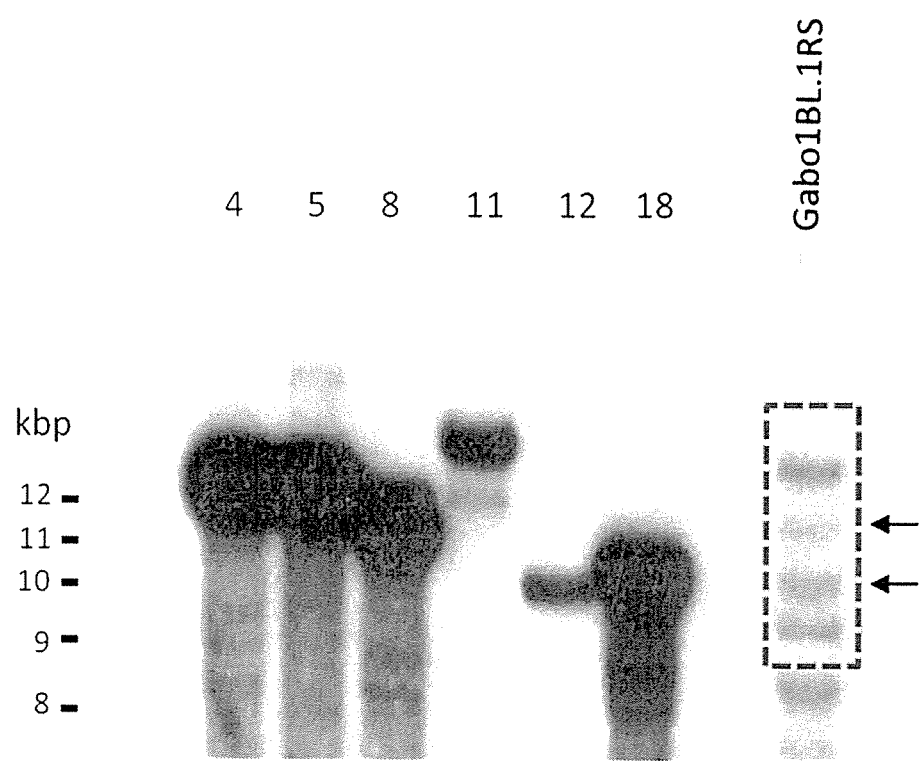

13 Claims, 3 Drawing Sheets
Specification includes a Sequence Listing.

STEM RUST RESISTANCE GENE

INCORPORATION BY REFERENCE OF SEQUENCE LISTING PROVIDED AS A TEXT FILE

A Sequence Listing is provided herewith a text file, "RICE-208 Seq Listing_ST25", created on Sep. 28, 2020 and having a size of 83 kb. The contents of the text file are incorporated by reference herein in their entirety.

FIELD OF THE INVENTION

The present invention relates to a transgenic plant which has integrated into its genome an exogenous polynucleotide encoding a polypeptide which confers resistance to one or more races of *Puccinia graminis*, such as the Ug99 group of races of *Puccinia graminis* f sp. *tritici*.

BACKGROUND OF THE INVENTION

The fungal pathogen *Puccinia graminis* Pers. f sp. *tritici* (Pgt), the causal agent of wheat stem rust, is a major threat to wheat production, in part because of the level of devastation it can inflict on wheat crops with near complete losses in severe epidemics. Although rust resistant cultivars had controlled the disease for over 40 years, the appearance in Uganda in 1999 of Pgt race TTKSK, commonly known as Ug99, and the subsequent spread of its derivatives to other parts of Africa and the Middle East, has highlighted the continuing danger of stem rust. Ug99 and derivative strains are virulent on plants containing the stem rust resistance gene Sr31, which had previously provided effective resistance for over thirty years (Ellis et al., 2014), as well as many other common stem rust resistance (Sr) genes (Singh et al., 2011). The recent appearance of another Pgt race (different to the Ug99 lineage) in Germany and Ethiopia in 2013-2014 attacking important commercial wheat varieties has raised further serious concerns for wheat production. While an international collaboration called the Borlaug Global Rust Initiative (BGRI) has since been actively involved in strategies to control stem rust, changes in global climate and warming can potentially open additional areas for rust epidemics which were previously considered safe from stem rust (Chakraborty et al., 2011).

The control of wheat rust is dependent on the incorporation of effective resistance genes during breeding and combinations of multiple stem rust resistance genes are crucial for providing durable resistance, which necessitates the identification of new resistance genes. Wild and cultivated relatives of wheat provide an important pool of new genes effective against wheat rust pathogens. Cereal rye (*Secale cereale*) is one such source and several rye genes have been used in breeding rust resistant bread wheat and triticale. Indeed, the Sr31 resistance gene was introgressed from rye as a full chromosome substitution for wheat chromosome 1B or as a translocation of the short arm of rye chromosome 1 (1RS) from the rye cultivar Petkus (Zeller, 1973) to the long arm of wheat chromosome 1B (1BL) and conferred stem rust resistance for over 30 years in the field (Ellis et al., 2014). Sr50 (previously known as SrR) was also introgressed into wheat as translocations of 1RS to the long arms of wheat chromosomes 1B and 1D, but sourced from the rye cultivar Imperial (Shepherd 1973; Mago et al., 2004). A third stem rust resistance gene, also known as Sr1RS$^{Amigo}$, was introgressed as a 1RS translocation from rye cultivar Insave to wheat chromosome 1A in cultivar Amigo (Zeller and Fuchs, 1983). Because these rye genes gave resistance to all known Pgt strains, it was not clear whether they represented different resistance specificities. Both Sr31 and Sr50 are associated with a cluster of genes on 1RS (Mago et al., 2004 and 2005), encoding coiled-coil nucleotide binding leucine-rich repeat (CC-NB-LRR) proteins orthologous to the barley Mla gene cluster, that provides resistance to *Blumeria graminis* f. sp. *hordei* (powdery mildew pathogen) (Wei et al., 1999 and 2002). However, it was not known which if any of these proteins was the product of the Sr50 gene itself. The recently cloned Sr33 gene from *Triticum tauschii* (Periyannan et al., 2013) is an ortholog of Mla, and like Sr50 provides resistance to worldwide Pgt isolates so again it has not been possible to distinguish these two specificities.

The Mla locus of barley is one of the most diverse classes of resistance genes in cereals, encoding more than 30 different alleles with different resistance specificities to barley powdery mildew (Seeholzer et al., 2010). This locus is also a potential source of useful disease resistance in other cereals, including wheat. For instance, the wheat TmMla1 gene present in the diploid A-genome wheat species *Triticum monococcum* is an ortholog of Mla and confers race-specific resistance to wheat powdery mildew (Jordan et al., 2011). The recently identified Sr33 gene, transferred to wheat from the diploid D-genome species *Ae. tauschii*, is the first known member of the Mla family to provide resistance to Pgt (Periyannan et al., 2013).

There is an urgent need for the identification of genes which confer at least some level of resistance to plants, especially wheat, against *Puccinia graminis*, such as the Ug99 group of races of *Puccinia graminis* f sp. *tritici*.

SUMMARY OF THE INVENTION

The present inventors have identified polypeptides which confer at least some level of resistance to plants, especially rye and wheat, against *Puccinia graminis*, such as the Ug99 group of races of *Puccinia graminis* f. sp. *tritici*.

Thus, in a first aspect the present invention provides a transgenic plant which has integrated into its genome an exogenous polynucleotide encoding a polypeptide which confers resistance to *Puccinia graminis*, wherein the polynucleotide is operably linked to a promoter capable of directing expression of the polynucleotide in a cell of the plant.

In an embodiment, the *Puccinia graminis* is *Puccinia graminis* f. sp. *tritici*. In a further embodiment, the *Puccinia graminis* f. sp. *tritici* is a race of the Ug99 group.

In another embodiment, the transgenic plant has enhanced resistance to *Puccinia graminis* when compared to an isogenic plant lacking the exogenous polynucleotide.

In an embodiment, the polypeptide is an Sr50 polypeptide.

In a further embodiment,
i) the polypeptide comprises amino acids having a sequence as provided in SEQ ID NO:1, a biologically active fragment thereof, or an amino acid sequence which is at least 82% identical to SEQ ID NO:1, and/or
ii) the polynucleotide comprises nucleotides having a sequence as provided in SEQ ID NO:10, a sequence which is at least 82% identical to SEQ ID NO:10, or a sequence which hybridizes to SEQ ID NO:10.

In an embodiment, the polypeptide comprises one or more, preferably all, of a coiled coil (CC) domain, an nucleotide binding (NB) domain and a leucine rich repeat (LRR) domain.

In a further embodiment, the polypeptide comprises one or more, preferably all, of a p-loop motif, and a kinase3a motif in the NB domain.

In an embodiment, the p-loop motif comprises the sequence GxxGxGK(T/S)T (SEQ ID NO:4), more preferably the sequence GFGGLGKTT (SEQ ID NO:5).

In an embodiment, the kinase 3a motif comprises the sequence GxxxxxTxR (SEQ ID NO:6), more preferably the sequence GSRLITTTR (SEQ ID NO:7).

In a further embodiment, the LRR domain comprises about 5 to about 20, or about 10 to about 20, imperfect repeats of the sequence xxLxLxxxx (SEQ ID NO:8).

In an embodiment, the polypeptide confers greater resistance to *Puccinia graminis* f sp. *tritici* race TTKSK than Sr33 (with a sequence of amino acids as provided in SEQ ID NO:13). In another embodiment, Sr33 (with a sequence of amino acids as provided in SEQ ID NO:13) confers greater resistance to *Puccinia graminis* f. sp. *tritici* race QFCSC than a polypeptide of the invention. In an embodiment, as detailed in Example 2, the greater resistance is determined when the polypeptide of the invention is in *T. aestivum* line Gabo 1DL.1RS-DR.A1 and when Sr33 is in *T. aestivum* line Westonia/CS1D5405.

Preferably, the plant is a cereal plant. Examples of transgenic cereal plants of the invention include, but are not limited to wheat, barley, maize, rice, oats, sorghum and triticale. In a particularly preferred embodiment, the plant is wheat.

In a further embodiment, the plant comprises one or more further exogenous polynucleotides encoding another plant pathogen resistance polypeptide. Examples of such other plant pathogen resistance polypeptides include, but are not limited to, Lr34, Lr1, Lr3, Lr2a, Lr3ka, Lr11, Lr13, Lr16, Lr17, Lr18, Lr21, LrB, Sr35 and Sr33. In an embodiment, the plant at least further comprises an exogenous polynucleotide encoding plant pathogen resistance polypeptide Sr33. For example, the at least further comprises an exogenous polynucleotide encoding a polypeptide comprising amino acids having a sequence as provided in SEQ ID NO:13 or SEQ ID NO:14, or an amino acid sequence which is at least 87% identical, at least 90% identical, or at least 95% identical, to one or both of SEQ ID NO:13 and SEQ ID NO:14 which confers resistance to *Puccinia graminis*.

Preferably, the plant is homozygous for the exogenous polynucleotide.

In an embodiment, the plant is growing in a field.

In a further aspect, the present invention provides a transgenic plant which has integrated into its genome an exogenous polynucleotide encoding a polypeptide which comprises amino acids having a sequence as provided in SEQ ID NO:1, or an amino acid sequence which is at least 82% identical to SEQ ID NO:1, wherein the polynucleotide is operably linked to a promoter capable of directing expression of the polynucleotide in a cell of the plant.

Also provided is a population of at least 100 transgenic plants of the invention growing in a field.

In a further aspect, the present invention provides a process for identifying a polynucleotide encoding a polypeptide which confers resistance to *Puccinia graminis* comprising:

i) obtaining a polynucleotide operably linked to a promoter, the polynucleotide encoding a polypeptide comprising amino acids having a sequence as provided in SEQ ID NO:1, a biologically active fragment thereof, or an amino acid sequence which is at least 82% identical to SEQ ID NO:1, ii) introducing the polynucleotide into a plant, iii) determining whether the level of resistance to *Puccinia graminis* is modified relative to an isogenic plant lacking the polynucleotide, and iv) optionally, selecting a polynucleotide which when expressed confers resistance to *Puccinia graminis*.

In an embodiment the process has one or more of the following, a) the polynucleotide comprises nucleotides having a sequence as provided in SEQ ID NO:10, a sequence which is at least 82% identical to SEQ ID NO:10, or a sequence which hybridizes to SEQ ID NO:10, b) the plant is a cereal plant such as a wheat plant, c) the polypeptide is a plant polypeptide or mutant thereof, and d) step ii) further comprises stably integrating the polynucleotide operably linked to a promoter into the genome of the plant.

Also provided is a substantially purified and/or recombinant *Puccinia graminis* plant resistance polypeptide.

In an embodiment, the polypeptide is an Sr50 polypeptide.

In another embodiment, the polypeptide comprises amino acids having a sequence as provided in SEQ ID NO:1, a biologically active fragment thereof, or an amino acid sequence which is at least 82% identical, at least 90% identical, or at least 95% identical, to SEQ ID NO:1.

In a further aspect, the present invention provides a substantially purified and/or recombinant polypeptide comprising amino acids having a sequence as provided in SEQ ID NO:1, or an amino acid sequence which is at least 82% identical, at least 90% identical, or at least 95% identical, to SEQ ID NO:1.

In an embodiment, a polypeptide of the invention is a fusion protein further comprising at least one other polypeptide sequence. The at least one other polypeptide may be, for example, a polypeptide that enhances the stability of a polypeptide of the present invention, or a polypeptide that assists in the purification or detection of the fusion protein.

In yet a further aspect, the present invention provides an isolated and/or exogenous polynucleotide comprising nucleotides having a sequence as provided in SEQ ID NO:10, a sequence which is at least 82% identical to SEQ ID NO:10, a sequence encoding a polypeptide of the invention, or a sequence which hybridizes to SEQ ID NO:10.

In another aspect, the present invention provides a chimeric vector comprising the polynucleotide of the invention.

Preferably, the polynucleotide is operably linked to a promoter.

In a further aspect, the present invention provides a recombinant cell comprising an exogenous polynucleotide of the invention and/or a vector of the invention.

The cell can be any cell type such as, but not limited to, a plant cell, a bacterial cell, an animal cell or a yeast cell.

Preferably, the cell is a plant cell. More preferably, the plant cell is a cereal plant cell. Even more preferably, the cereal plant cell is a wheat cell.

In a further aspect, the present invention provides a method of producing the polypeptide of the invention, the method comprising expressing in a cell or cell free expression system the polynucleotide of the invention.

Preferably, the method further comprises isolating the polypeptide.

In yet another aspect, the present invention provides a transgenic non-human organism comprising an exogenous polynucleotide of the invention, a vector of the invention and/or a recombinant cell of the invention.

Preferably, the transgenic non-human organism is a plant. Preferably, the plant is a cereal plant. More preferably, the cereal plant is a wheat plant.

In another aspect, the present invention provides a method of producing the cell of the invention, the method comprising the step of introducing the polynucleotide of the invention, or a vector of the invention, into a cell.

Preferably, the cell is a plant cell.

In a further aspect, the present invention provides a method of producing a transgenic plant of the invention, the method comprising the steps of
 i) introducing a polynucleotide of the invention and/or a vector of the invention into a cell of a plant,
 ii) regenerating a transgenic plant from the cell, and
 iii) optionally harvesting seed from the plant, and/or
 iv) optionally producing one or more progeny plants from the transgenic plant, thereby producing the transgenic plant.

In a further aspect, the present invention provides a method of producing a plant which has integrated into its genome a polynucleotide encoding a polypeptide which confers resistance to *Puccinia graminis*, the method comprising the steps of
 i) crossing two parental plants, wherein at least one plant comprises a polynucleotide encoding a polypeptide which confers resistance to *Puccinia graminis*,
 ii) screening one or more progeny plants from the cross for the presence or absence of the polynucleotide, and
 iii) selecting a progeny plant which comprise the polynucleotide, thereby producing the plant.

In an embodiment, at least one of the parental plants is a transgenic plant of the invention, and the selected progeny plant comprises an exogenous polynucleotide encoding a polypeptide which confers resistance to *Puccinia graminis*.

In a further embodiment, at least one of the parental plants is a tetraploid or hexaploid wheat plant.

In yet another embodiment, step ii) comprises analysing a sample comprising DNA from the plant for the polynucleotide.

In another embodiment, step iii) comprises
 i) selecting progeny plants which are homozygous for the polynucleotide, and/or
 ii) analysing the plant or one or more progeny plants thereof for resistance to *Puccinia graminis*.

In an embodiment, the method further comprises
 iv) backcrossing the progeny of the cross of step i) with plants of the same genotype as a first parent plant which lacked a polynucleotide encoding a polypeptide which confers resistance to *Puccinia graminis* for a sufficient number of times to produce a plant with a majority of the genotype of the first parent but comprising the polynucleotide, and
 iv) selecting a progeny plant which has resistance to *Puccinia graminis*.

In yet another aspect, a method of the invention further comprises the step of analysing the plant for at least one other genetic marker.

Also provide is a plant produced using a method of the invention.

In another aspect, the present invention provides for the use of the polynucleotide of the invention, or a vector of the invention, to produce a recombinant cell and/or a transgenic plant.

In an embodiment, the transgenic plant has enhanced resistance to *Puccinia graminis* when compared to an isogenic plant lacking the exogenous polynucleotide and/or vector.

In a further aspect, the present invention provides a method for identifying a plant comprising a polynucleotide encoding a polypeptide which confers resistance to *Puccinia graminis*, the method comprising the steps of
 i) obtaining a nucleic acid sample from a plant, and
 ii) screening the sample for the presence or absence of the polynucleotide, wherein presence of the polynucleotide indicates that the plant is resistant to *Puccinia graminis*.

In an embodiment, the polynucleotide encodes a polypeptide of the invention.

In a further embodiment, the method identifies a transgenic plant of the invention.

In another embodiment, the method further comprises producing a plant from a seed before step i).

Also provided is a plant part of the plant of the invention.

In an embodiment, the plant part is a seed that comprises an exogenous polynucleotide which encodes a polypeptide which confers resistance to *Puccinia graminis*.

In a further aspect, the present invention provides a method of producing a plant part, the method comprising,
 a) growing a plant of the invention, and
 b) harvesting the plant part.

In another aspect, the present invention provides a method of producing flour, wholemeal, starch or other product obtained from seed, the method comprising;
 a) obtaining seed of the invention, and
 b) extracting the flour, wholemeal, starch or other product.

In a further aspect, the present invention provides a product produced from a plant of the invention and/or a plant part of the invention.

In an embodiment, the part is a seed.

In an embodiment, the product is a food product or beverage product. Examples include, but are not limited to;
 i) the food product being selected from the group consisting of: flour, starch, leavened or unleavened breads, pasta, noodles, animal fodder, breakfast cereals, snack foods, cakes, malt, beer, pastries and foods containing flour-based sauces, or
 ii) the beverage product being beer or malt.

In an alternative embodiment, the product is a non-food product. Examples include, but are not limited to, films, coatings, adhesives, building materials and packaging materials.

In a further aspect, the present invention provides a method of preparing a food product of the invention, the method comprising mixing seed, or flour, wholemeal or starch from the seed, with another food ingredient.

In another aspect, the present invention provides a method of preparing malt, comprising the step of germinating seed of the invention.

Also provided is the use of a plant of the invention, or part thereof, as animal feed, or to produce feed for animal consumption or food for human consumption.

In a further aspect, the present invention provides a composition comprising one or more of a polypeptide of the invention, a polynucleotide of the invention, a vector of the invention, or a recombinant cell of the invention, and one or more acceptable carriers.

In another aspect, the present invention provides a method of identifying a compound that binds to a polypeptide comprising amino acids having a sequence as provided in SEQ ID NO:1, a biologically active fragment thereof, or an amino acid sequence which is at least 82% identical to SEQ ID NO:1, the method comprising:
 i) contacting the polypeptide with a candidate compound, and
 ii) determining whether the compound binds the polypeptide.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Isolation of phage lambda DNA clones from the Sr50 locus. The autoradiograph shows hybridisation of P32-labelled probe B76 to DraI digested lambda clones 4, 5, 8, 11, 12, and 18 and genomic DNA of wheat plants Gabo 1BL.1RS. The gel-purified region used to make the lambda genomic DNA library is indicated on the Gabo1BL.1RS lane in a dotted box with the fragments missing in deletion mutants indicated by arrows.

Figure 2:
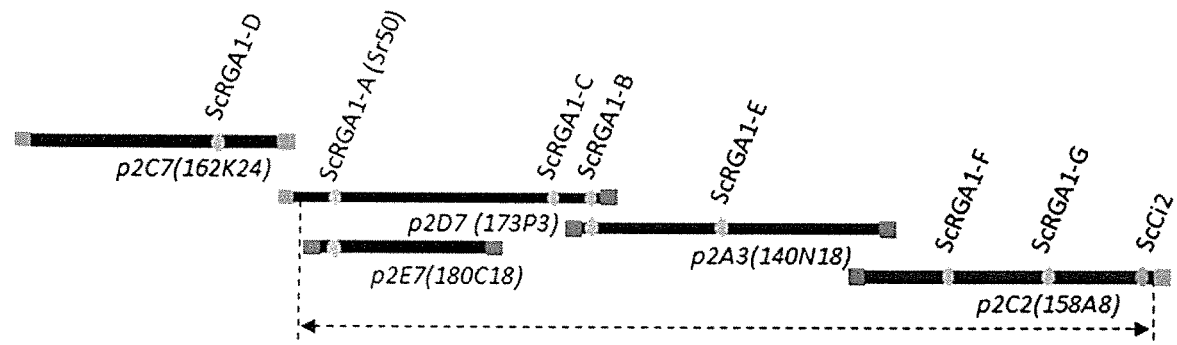

FIG. 2. Schematic representation of the BAC contig at the Sr50 locus. The map of five overlapping BAC clones is shown, spanning the deletion (dotted line) in mutant M2. BAC end sequences within the deletion were not present in M2, whereas BAC end sequences outside of the deletion were present in M2. The relative positions of ScRGA1-A to G gene family members and of a predicted chymotrypsin inhibitor gene (ScCI2) are shown within the five BAC clones. ScRGA1-A was shown to be the Sr50 gene as described herein.

Figure 3:
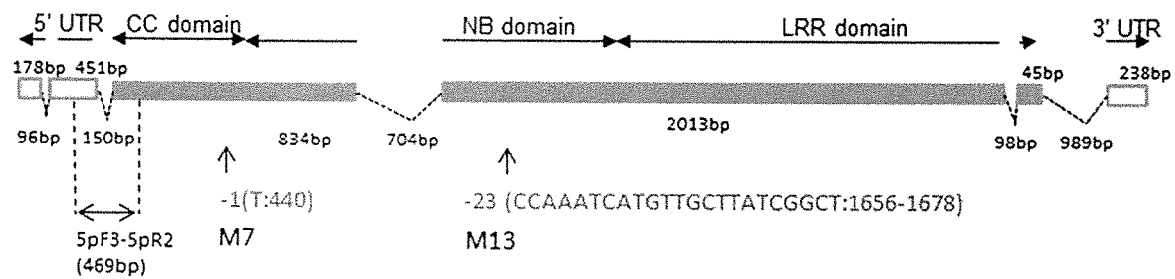

FIG. 3. Structure of the Sr50 gene. The Figure shows a schematic representation of the structure of the Sr50 (ScRGA1-A) gene including the 5' and 3' UTRs, the sizes of introns and exons (in basepairs; bp) and position of mutations in mutants M7 and M13. The relative positions of the CC, NB and LRR domains in the Sr50 polypeptide and the position of the 5pF3 and 5pR2 primers for amplification of a region including the translational start codon are also shown. The sequence of FIG. 3 is set forth in SEQ ID NO: 60.

Figure 4:
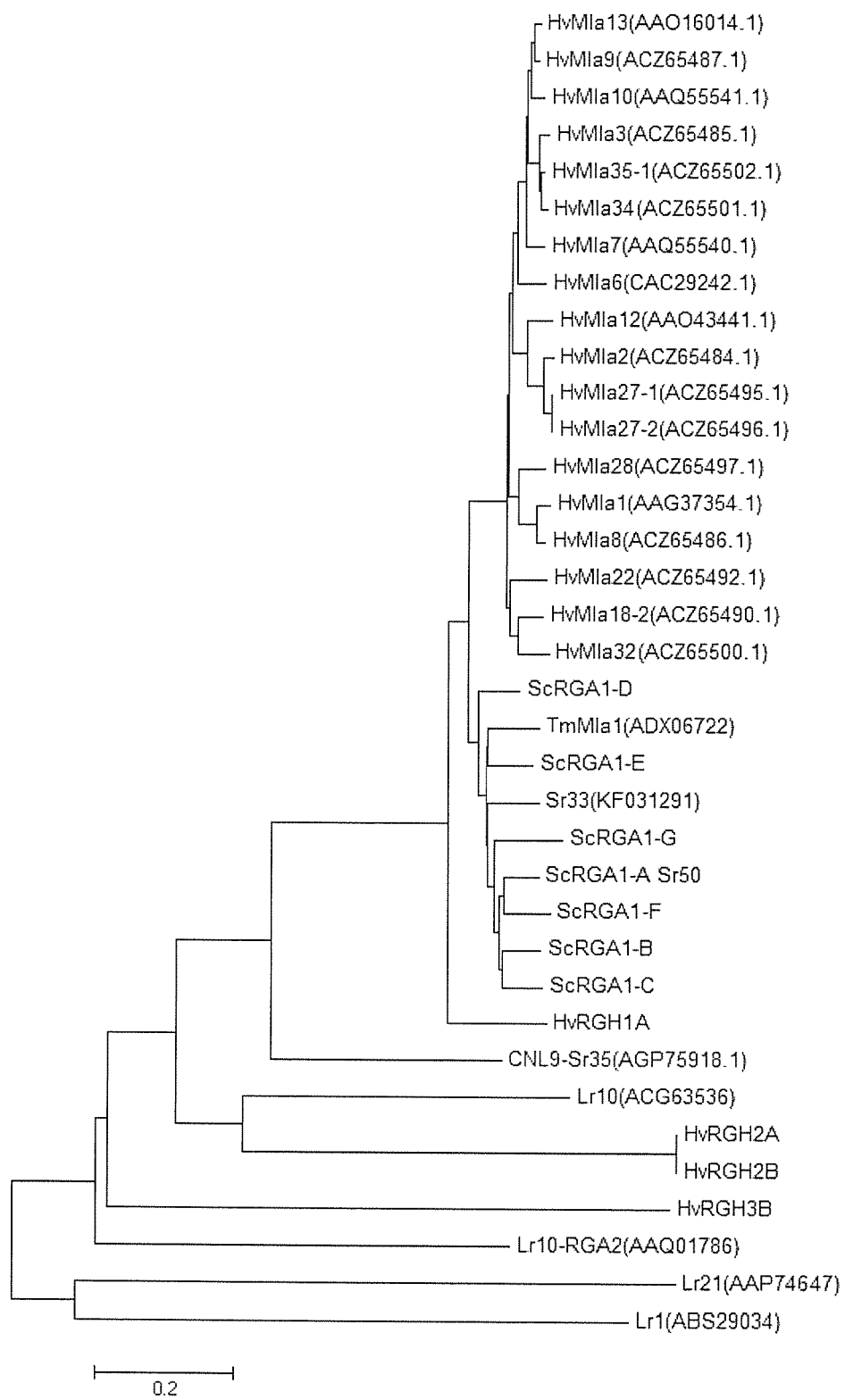

FIG. 4. Phylogenetic relationship of Sr50 and related Mla family CC-NB-LRR proteins. A neighbor-joining tree was obtained from the predicted amino acid sequences of ScRGA1 genes from *S. cereale*, known functional MLA members of barley (HvMLA), TmMLA from *T. monococcum*, Sr33, Sr35 and leaf rust resistance polypeptides Lr1, Lr10 and Lr21.

KEY TO THE SEQUENCE LISTING

SEQ ID NO:1—Amino acid sequence of stem rust resistance polypeptide (Sr50).

SEQ ID NO:2—Amino acid sequence of Sr50 variant from Svalofs Otello and Frontier.

SEQ ID NO:3—Amino acid sequence of Sr50 variant from Dwarf Petkus.

SEQ ID NO:4—Consensus p-loop motif.

SEQ ID NO:5—P-loop motif of polypeptide provided as SEQ ID NO:1.

SEQ ID NO:6—Consensus kinase 3a motif.

SEQ ID NO:7—Kinase 3a motif of polypeptide provided as SEQ ID NO:1.

SEQ ID NO:8—Consensus repeat of the LRR domain.

SEQ ID NO:9—Nucleotide sequence of cDNA encoding stem rust resistance polypeptide (Sr50).

SEQ ID NO:10—Nucleotide sequence of open reading frame encoding stem rust resistance polypeptide (Sr50).

SEQ ID NO:11—Nucleotide sequence of pVecNeoSr50 expression construct.

SEQ ID NO:12—Nucleotide sequence of pVecBarSr50 expression construct.

SEQ ID NO:13—Amino acid sequence of stem rust resistance polypeptide (from haplotype I) (Sr33).

SEQ ID NO:14—Amino acid sequence of allelic variant of the stem rust resistance polypeptide provided as SEQ ID NO:13 (from haplotype II) (Sr33).

SEQ ID NO:15—Functional nuclear export signal NES from HIV Rev.

SEQ ID NO:16—Non-functional nes.

SEQ ID NOs 17 to 59—Oligonucleotide primers.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, plant molecular biology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, more preferably +/−1%, more preferably +/−0.5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Stem Rust

As used herein, "stem rust" refers to the disease of plants caused by *Puccinia graminis* or to the causative fungal pathogen, *Puccinia graminis*, as the context determines. As used herein, "wheat stem rust" refers to the disease of plants caused by *Puccinia graminis* f sp. *tritici* or to the causative fungal pathogen, *Puccinia graminis* f. sp. *tritici*, as the context determines.

The Ug99 group of races of wheat stem rust (*Puccinia graminis* f. sp. *tritici*) (also known as 'TTKSK' under the North American nomenclature system) is a well known fungal pathogen of wheat and is commonly present in wheat fields in countries such as in Africa and the Middle East (Singh et al., 2011; Hodson et al., 2012). Ug99 can cause major crop losses and is virulent against resistance genes that have previously protected wheat against stem rust. There are currently eight known variants of group Ug99 which are closely related based on DNA marker analysis. Each variant of the pathogen which differs in its virulence/avirulence profile on a panel of wheat plants each comprising a different resistance R gene is known as a "race" of the pathogen. The Ug99 group of isolates are all closely related and are believed to have evolved from a common ancestor, but may differ in their virulence/avirulence profiles in which case they are considered different races. Seven of these eight variants are summarized in Table 2 of Singh et al. (2011). In an embodiment, the Ug99 group of stem rust races exhibit virulence on wheat plants comprising one or more of the resistance genes Sr31, Sr21, Sr24 and Sr36 (Singh et al., 2011). In one embodiment, the Ug99 group of stem rust races of *Puccinia graminis* f sp. *tritici* has virulence at least to wheat plants comprising the resistance gene Sr31 (Pretorius et al., 2000).

Polypeptides/Peptides

The present invention relates to polypeptides which confer resistance to a plant, for example a wheat plant, to stem rust, preferably to wheat stem rust such as the Ug99 group of races. In a preferred embodiment, the polypeptide is encoded by an allele or variant of an Sr50 gene which confers resistance to wheat stem rust. Examples of such polypeptides include, but are not limited to, those comprising an amino acid sequence as provided in SEQ ID NO:1. The polypeptide of the invention confers enhanced resistance to stem rust, preferably wheat stem rust such as the Ug99 group of races of *Puccinia graminis* f. sp. *tritici* when compared to an isogenic plant lacking a gene encoding the polypeptide. This term also refers to the naturally produced protein (or wild-type protein from which a mutant protein is derived) encoded by a gene conferring upon a plant (for example, wheat), when grown in normal field conditions, enhanced resistance to stem rust such as the Ug99 group of races of *Puccinia graminis* f sp. *tritici*. In a preferred embodiment, the polypeptide of the invention confers resistance specifically to stem rust, preferably specifically to wheat stem rust, more preferably it does not confer resistance to wheat leaf rust caused by the fungal pathogen *Puccinia triticina* and/or to powdery mildew. In this context, "specifically to stem rust" and "specifically to wheat stem rust" means that the conferred resistance is preferentially to stem rust or wheat stem rust in comparison to another fungal pathogen of the same plant species, preferably to many or most other fungal pathogens of the same species. In a more preferred embodiment, the polypeptide of the invention confers resistance to stem rust and at least two, or all three, of leaf rust, stripe rust and powdery mildew, preferably in wheat. In an embodiment, polypeptides of the invention are not encoded by the Sr35 gene of a wheat plant. In an embodiment, polypeptides of the invention are not encoded by the Sr35 gene of a wheat plant or its homologs, such as those that are at least 50% identical in amino acid sequence to the Sr35 polypeptide. In another embodiment, polypeptides of the invention are not encoded by the Sr33 gene of a wheat plant. In an embodiment, polypeptides of the invention are not encoded by the Sr33 gene of a wheat plant or its homologs, such as those that are at least 87% identical in amino acid sequence to the Sr33 polypeptide as described in WO 2014/000594 (SEQ ID NO's 13 and 14 herein). Thus, in an embodiment, a polypeptide of the invention does not comprise amino acids having a sequence at least 87% identical in amino acid sequence to SEQ ID NO:13 and/or SEQ ID NO:14. In a further embodiment, a polypeptide of the invention has an amino acid sequence which is more closely related (has a higher % identity level) to SEQ ID NO:1 than SEQ ID NO:13 and/or 14.

In a further embodiment, when expressed in a transgenic plant infected with stem rust, such as with a Ug99 race of *Puccinia graminis* f. sp. *tritici*, the cells of the plant display little, if any, signs of cell death (autofluorescence), for instance when compared to an isogenic plant expressing Sr45.

Polypeptides of the invention typically comprise a coiled coil (CC) domain towards the N-terminus, followed by an nucleotide binding (NB) domain and a leucine rich repeat (LRR) domain towards the C-terminus (see FIG. 3). Each of these three types of domains are common in polypeptides that confer resistance to plant pathogens. In addition, CC-NB-LRR containing polypeptides are a known large class of polypeptides which, as a class, confer resistance across a wide variety of different plant pathogens (see, for example, Bulgarelli et al., 2010; McHale et al., 2006; Takken et al., 2006; Wang et al., 2011; Gennaro et al., 2009; and Dilbirligi et al., 2003), although each CC-NB-LRR polypeptides is specific to a particular species or sub-species of pathogen. Accordingly, by aligning the polypeptides of the invention with other CC-NB-LRR polypeptides, combined with the large number of studies on these types of proteins as well as CC domains, NB domains and LRR domains, the skilled person has a considerable amount of guidance for designing functional variants of the specific polypeptides provided herein.

A coiled-coil domain or motif is a structural motif which is one of the most common tertiary structures of proteins where α-helices are coiled together like the strands of a rope. Computer programs have been devised to detect heptads and resulting in coiled-coil structures (see, for example Delorenzi and Speed, 2002). Coiled coils typically comprise a repeated pattern, hxxhcxc, of hydrophobic (h) and charged (c) amino-acid residues, referred to as a heptad repeats. The positions in the heptad repeat are usually labeled abcdefg, where a and d are the hydrophobic positions, often being occupied by isoleucine, alanine, leucine or valine. Folding a protein with these hepatds into an α-helical secondary structure causes the hydrophobic residues to be presented as a 'stripe' that coils gently around the helix in left-handed fashion, forming an amphipathic structure.

The NB domain is present in resistance genes as well as several kinases such as ATP/GTP-binding proteins. This domain typically contains three motifs: kinase-1a (p-loop), a kinase-2, and a putative kinase-3a (Traut 1994; Tameling et al., 2002). The consensus sequence of GxxGxGK(T/S)T (SEQ ID NO:4) (GFGGLGKTT (SEQ ID NO:5) in the polypeptide which confers resistance to *Puccinia graminis* provided as SEQ ID NO:1), and GxxxxxTxR (SEQ ID NO:6) (GSRLITTTR (SEQ ID NO:7) in the polypeptide which confers resistance to *Puccinia graminis* provided as SEQ ID NO:1) for the resistance gene motifs p-loop, kinase-2, and the putative kinase-3a, respectively, are different from those present in other NB-encoding proteins. Other motifs present in the NB domain of NB/LRR-type resistance genes are GLPL, RNBS-D and MHD (Meyers et al., 1999). The sequences interspersing these motifs and domains can be very different even among homologues of a resistance gene (Michelmore and Meyers, 1998; Pan et al., 2000).

A leucine-rich domain is a protein structural motif that forms an α/β horseshoe fold (Enkhbayar et al., 2004). The LRR domain contains 9-41 imperfect repeats, each about 25 amino acids long with a consensus amino acid sequence of xxLxLxxxx (SEQ ID NO:8) (Cooley et al., 2000). In an embodiment, a polypeptide of the invention comprises about 10 to about 20, more preferably about 12 to about 18, more preferably about 15 leucine rich repeats. These repeats commonly fold together to form a solenoid protein domain. Typically, each repeat unit has beta strand-turn-alpha helix structure, and the assembled domain, composed of many such repeats, has a horseshoe shape with an interior parallel beta sheet and an exterior array of helices.

In an embodiment, the polypeptide comprises one, two, three, four or more amino acids which are present in the amino acid sequence provided as SEQ ID NO:1 but which are not found in the corresponding amino acid position of a polypeptide comprising amino acids having a sequence as provided in SEQ ID NO:13 and SEQ ID NO:14.

In an embodiment, the polypeptide does not comprise amino acids having a sequence as provided in SEQ ID NO:1 or SEQ ID NO:2, a biologically active fragment thereof, or an amino acid sequence which is at least 87% identical to one or both of SEQ ID NO:13 and SEQ ID NO:14. In an embodiment, polypeptide does not comprise amino acids having a sequence as provided in SEQ ID NO:13 or SEQ ID NO:14.

In an embodiment, the polypeptide is from *S. cereale*.

As used herein, "resistance" is a relative term in that the presence of a polypeptide of the invention (i) reduces the disease symptoms of a plant comprising the gene (R gene) that confers resistance, relative to a plant lacking the R gene, and/or (ii) reduces pathogen reproduction or spread on a plant comprising the R gene. Resistance as used herein is relative to the "susceptible" response of a plant to the same pathogen. Typically, the presence of the R gene improves at least one production trait of a plant comprising the R gene when infected with the pathogen, such as grain yield, when compared to an isogenic plant infected with the pathogen but lacking the R gene. The isogenic plant may have some level of resistance to the pathogen, or may be classified as susceptible. Thus, the terms "resistance" and "enhanced resistance" are generally used herein interchangeably. Furthermore, a polypeptide of the invention does not necessarily confer complete pathogen resistance, for example when some symptoms still occur or there is some pathogen reproduction on infection but at a reduced amount. Enhanced resistance can be determined by a number of methods known in the art such as analysing the plants for the amount of pathogen and/or analysing plant growth or the amount of damage or disease symptoms to a plant in the presence of the pathogen, and comparing one or more of these parameters to an isogenic plant lacking an exogenous gene encoding a polypeptide of the invention.

By "substantially purified polypeptide" or "purified polypeptide" we mean a polypeptide that has generally been separated from the lipids, nucleic acids, other peptides, and other contaminating molecules with which it is associated in its native state. Preferably, the substantially purified polypeptide is at least 90% free from other components with which it is naturally associated.

Transgenic plants and host cells of the invention may comprise an exogenous polynucleotide encoding a polypeptide of the invention. In these instances, the plants and cells produce a recombinant polypeptide. The term "recombinant" in the context of a polypeptide refers to the polypeptide encoded by an exogenous polynucleotide when produced by a cell, which polynucleotide has been introduced into the cell or a progenitor cell by recombinant DNA or RNA techniques such as, for example, transformation. Typically, the cell comprises a non-endogenous gene that causes an altered amount of the polypeptide to be produced. In an embodiment, a "recombinant polypeptide" is a polypeptide made by the expression of an exogenous (recombinant) polynucleotide in a plant cell.

The terms "polypeptide" and "protein" are generally used interchangeably.

The % identity of a polypeptide is determined by GAP (Needleman and Wunsch, 1970) analysis (GCG program) with a gap creation penalty=5, and a gap extension penalty=0.3. The query sequence is at least 150 amino acids in length, and the GAP analysis aligns the two sequences over a region of at least 150 amino acids. More preferably, the query sequence is at least 500 amino acids in length, and the GAP analysis aligns the two sequences over a region of at least 500 amino acids. More preferably, the query sequence is at least 750 amino acids in length and the GAP analysis aligns the two sequences over a region of at least 750 amino acids. Even more preferably, the query sequence is at least 900 amino acids in length and the GAP analysis aligns the two sequences over a region of at least 900 amino acids. Even more preferably, the GAP analysis aligns two sequences over their entire length.

As used herein a "biologically active" fragment is a portion of a polypeptide of the invention which maintains a defined activity of the full-length polypeptide such as when expressed in a plant, such as wheat, confers (enhanced) resistance to stem rust, preferably wheat stem rust such as the Ug99 group of races of *Puccinia graminis* f. sp. *tritici* when compared to an isogenic plant not expressing the polypeptide. Biologically active fragments can be any size as long as they maintain the defined activity but are preferably at least 750 or at least 900 amino acid residues long. Preferably, the biologically active fragment maintains at least 10%, at least 50%, at least 75% or at least 90%, of the activity of the full length protein.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics. Preferred amino acid sequence mutants have only one, two, three, four or less than 10 amino acid changes relative to the reference wildtype polypeptide.

Mutant (altered) polypeptides can be prepared using any technique known in the art, for example, using directed evolution or rational design strategies (see below). Products derived from mutated/altered DNA can readily be screened using techniques described herein to determine if they confer resistance to *Puccinia graminis* (for example, a race of the Ug99 group of *Puccinia graminis* f sp. *tritici*) such as by producing a transgenic plant expressing the mutated/altered DNA and determining the ability of the plant to produce grain in the presence of the pathogen.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. In order to maintain activity, sites of interest include those not in an active site, such as a CC, BD or LRR domain, and those which are not highly conserved between different species. These sites, especially those falling within a sequence of at least three other non-conserved sites can generally be substituted in a relatively conservative or non-conservative manner. Examples of conservative substitutions are shown in Table 1 under the heading of "exemplary substitutions".

TABLE 1

Exemplary substitutions.

| Original Residue | Exemplary Substitutions |
| --- | --- |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |

TABLE 1-continued

Exemplary substitutions.

| Original Residue | Exemplary Substitutions |
| --- | --- |
| Thr (T) | ser |
| Trp (W) | tyr |
| Tyr (Y) | trp; phe |
| Val (V) | ile; leu; met; phe, ala |

In a preferred embodiment a mutant/variant polypeptide has one or two or three or four conservative amino acid changes when compared to a naturally occurring polypeptide. Details of conservative amino acid changes are provided in Table 1. In a preferred embodiment, the changes are not in one or more of the motifs which are highly conserved between the different polypeptides provided herewith. As the skilled person would be aware, such minor changes can reasonably be predicted not to alter the activity of the polypeptide when expressed in a recombinant cell.

In an embodiment, the protein of the invention is a CC-NB-LRR plant pathogen resistance gene which comprises domains configured as shown in FIG. 3.

The primary amino acid sequence of a polypeptide of the invention can be used to design variants/mutants thereof based on comparisons with closely related resistance polypeptides comprising NB and LRR domains, more preferably CC, NB and LRR domains. As the skilled addressee will appreciate, residues highly conserved amongst closely related CC-NB-LRR proteins are less likely to be able to be altered, especially with non-conservative substitutions, and activity maintained than less conserved residues (see above).

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. The polypeptides may be post-translationally modified in a cell, for example by phosphorylation, which may modulate its activity. These modifications may serve to increase the stability and/or bioactivity of the polypeptide of the invention.

Directed Evolution

In directed evolution, random mutagenesis is applied to a protein, and a selection regime is used to pick out variants that have the desired qualities, for example, increased activity. Further rounds of mutation and selection are then applied. A typical directed evolution strategy involves three steps:

1) Diversification: The gene encoding the protein of interest is mutated and/or recombined at random to create a large library of gene variants. Variant gene libraries can be constructed through error prone. PCR (see, for example, Leung, 1989; Cadwell and Joyce, 1992), from pools of DNaseI digested fragments prepared from parental templates (Stemmer, 1994a; Stemmer, 1994b; Crameri et al., 1998; Coco et al., 2001) from degenerate oligonucleotides (Ness et al 2002, Coco, 2002) or from mixtures of both, or even from undigested parental templates (Zhao et al., 1998; Eggert et al., 2005; Jézéquek et al., 2008) and are usually assembled through PCR. Libraries can also be made from parental sequences recombined in vivo or in vitro by either homologous or non-homologous recombination (Ostermeier et al., 1999; Volkov et al., 1999; Sieber et al., 2001). Variant gene libraries can also be constructed by sub-cloning a gene of interest into a suitable vector, transforming the vector into a "mutator" strain such as the *E. coli* XL-1 red (Stratagene) and propagating the transformed bacteria for a suitable number of generations. Variant gene libraries can also be constructed by subjecting the gene of interest to DNA shuffling (i.e., in vitro homologous recombination of pools of selected mutant genes by random fragmentation and reassembly) as broadly described by Harayama (1998).

2) Selection: The library is tested for the presence of mutants (variants) possessing the desired property using a screen or selection. Screens enable the identification and isolation of high-performing mutants by hand, while selections automatically eliminate all nonfunctional mutants. A screen may involve screening for the presence of known conserved amino acid motifs. Alternatively, or in addition, a screen may involve expressing the mutated polynucleotide in a host organism or part thereof and assaying the level of activity.

3) Amplification: The variants identified in the selection or screen are replicated many fold, enabling researchers to sequence their DNA in order to understand what mutations have occurred.

Together, these three steps are termed a "round" of directed evolution. Most experiments will entail more than one round. In these experiments, the "winners" of the previous round are diversified in the next round to create a new library. At the end of the experiment, all evolved protein or polynucleotide mutants are characterized using biochemical methods.

Rational Design

A protein can be designed rationally, on the basis of known information about protein structure and folding. This can be accomplished by design from scratch (de novo design) or by redesign based on native scaffolds (see, for example, Hellinga, 1997; and Lu and Berry, Protein Structure Design and Engineering, Handbook of Proteins 2, 1153-1157 (2007)). Protein design typically involves identifying sequences that fold into a given or target structure and can be accomplished using computer models. Computational protein design algorithms search the sequence-conformation space for sequences that are low in energy when folded to the target structure. Computational protein design algorithms use models of protein energetics to evaluate how mutations would affect a protein's structure and function. These energy functions typically include a combination of molecular mechanics, statistical (i.e. knowledge-based), and other empirical terms. Suitable available software includes IPRO (Interative Protein Redesign and Optimization), EGAD (A Genetic Algorithm for Protein Design), Rosetta Design, Sharpen, and Abalone.

Polynucleotides and Genes

The present invention refers to various polynucleotides. As used herein, a "polynucleotide" or "nucleic acid" or "nucleic acid molecule" means a polymer of nucleotides, which may be DNA or RNA or a combination thereof, and includes genomic DNA, mRNA, cRNA, and cDNA. Less preferred polynucleotides include tRNA, siRNA, shRNA and hpRNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein, or comprise one or more modified nucleotides not found in nature, well known to those skilled in the art. The polymer may be single-stranded, essentially double-stranded or partly double-stranded. Basepairing as used herein refers to standard basepairing between nucleotides, including G:U basepairs. "Complementary" means two polynucleotides are capable of basepairing (hybridizing) along part of their lengths, or along the full length of one or both. A "hybridized polynucleotide" means the polynucleotide is actually basepaired to its complement. The term "polynucleotide" is used interchangeably herein with the term "nucleic acid". Preferred polynucleotides of the invention encode a polypeptide of the invention.

By "isolated polynucleotide" we mean a polynucleotide which has generally been separated from the polynucleotide sequences with which it is associated or linked in its native state, if the polynucleotide is found in nature. Preferably, the isolated polynucleotide is at least 90% free from other components with which it is naturally associated, if it is found in nature. Preferably the polynucleotide is not naturally occurring, for example by covalently joining two shorter polynucleotide sequences in a manner not found in nature (chimeric polynucleotide).

The present invention involves modification of gene activity and the construction and use of chimeric genes. As used herein, the term "gene" includes any deoxyribonucleotide sequence which includes a protein coding region or which is transcribed in a cell but not translated, as well as associated non-coding and regulatory regions. Such associated regions are typically located adjacent to the coding region or the transcribed region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

A "Sr50 gene" as used herein refers to a nucleotide sequence which is homologous to the isolated Sr50 gene or Sr50 cDNA (SEQ ID NO:9) described herein. As described herein, some alleles and variants of the Sr50 gene family encode a protein that confers resistance to stem rust (for example as caused by the Ug99 group of races of *Puccinia graminis* f sp. *tritici*). Sr50 genes include the naturally occurring alleles or variants existing in cereals such as wheat. Nucleic acid molecules having the nucleotide sequence shown herein as SEQ ID NO:9 (cDNA) or SEQ ID NO:10 (open reading frame), encoding a protein with amino acid sequence SEQ ID NO:1, are examples of an Sr50 gene which confers resistance to stem rust.

A genomic form or clone of a gene containing the transcribed region may be interrupted with non-coding sequences termed "introns" or "intervening regions" or "intervening sequences", which may be either homologous or heterologous with respect to the "exons" of the gene. An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or, preferably, for integration into the host genome.

As used herein, a "chimeric gene" refers to any gene that comprises covalently joined sequences that are not found joined in nature. Typically, a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule", "recombinant polynucleotide" or variations thereof refer to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations.

Foreign or exogenous genes may be genes that are inserted into a non-native organism, native genes introduced into a new location within the native host, or chimeric genes. A "transgene" is a gene that has been introduced into the genome by a transformation procedure. The term "genetically modified" includes introducing genes into cells by transformation or transduction, mutating genes in cells and altering or modulating the regulation of a gene in a cell or organisms to which these acts have been done or their progeny.

Furthermore, the term "exogenous" in the context of a polynucleotide (nucleic acid) refers to the polynucleotide when present in a cell that does not naturally comprise the polynucleotide. The cell may be a cell which comprises a non-endogenous polynucleotide resulting in an altered amount of production of the encoded polypeptide, for example an exogenous polynucleotide which increases the expression of an endogenous polypeptide, or a cell which in its native state does not produce the polypeptide. Increased production of a polypeptide of the invention is also referred to herein as "over-expression". An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide of the invention operably linked to a promoter suitable of driving transcription of the open reading frame in a cell of interest.

In an embodiment, the polynucleotide is not naturally occurring such as comprising nucleotides having a sequence as provided in SEQ ID NO:10. For example, in an embodiment the polynucleotide is a codon optimised polynucleotide encoding a polypeptide comprising amino acids having a sequence as provided in SEQ ID NO:1, a biologically active fragment thereof, or an amino acid sequence which is at least 82% identical, at least 90% identical, or at least 95% identical, to SEQ ID NO:1, for expression in a plant other than rye (such as wheat).

In an embodiment, if present in a rye plant, or part (such a ryegrain) or cell thereof, the polynucleotide is not present on chromosome 1RS.

The % identity of a polynucleotide is determined by GAP (Needleman and Wunsch, 1970) analysis (GCG program) with a gap creation penalty=5, and a gap extension penalty=0.3. The query sequence is at least 450 nucleotides in length, and the GAP analysis aligns the two sequences over a region of at least 450 nucleotides. Preferably, the query sequence is at least 1,500 nucleotides in length, and the GAP analysis aligns the two sequences over a region of at least 1,500 nucleotides. Even more preferably, the query sequence is at least 2,700 nucleotides in length and the GAP analysis aligns the two sequences over a region of at least 2,700 nucleotides. Even more preferably, the GAP analysis aligns two sequences over their entire length.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In a further embodiment, the present invention relates to polynucleotides which are substantially identical to those specifically described herein. As used herein, with reference to a polynucleotide the term "substantially identical" means the substitution of one or a few (for example 2, 3, or 4) nucleotides whilst maintaining at least one activity of the native protein encoded by the polynucleotide. In addition, this term includes the addition or deletion of nucleotides which results in the increase or decrease in size of the encoded native protein by one or a few (for example 2, 3, or 4) amino acids whilst maintaining at least one activity of the native protein encoded by the polynucleotide.

The present invention also relates to the use of oligonucleotides, for instance in methods of screening for a polynucleotide of, or encoding a polypeptide of, the invention. As used herein, "oligonucleotides" are polynucleotides up to 50 nucleotides in length. The minimum size of such oligonucleotides is the size required for the formation of a stable hybrid between an oligonucleotide and a complementary sequence on a nucleic acid molecule of the present invention. They can be RNA, DNA, or combinations or derivatives of either. Oligonucleotides are typically relatively short single stranded molecules of 10 to 30 nucleotides, commonly 15-25 nucleotides in length. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least nucleotides, even more preferably at least 25 nucleotides in length. Oligonucleotides of the present invention used as a probe are typically conjugated with a label such as a radioisotope, an enzyme, biotin, a fluorescent molecule or a chemiluminescent molecule.

The present invention includes oligonucleotides that can be used as, for example, probes to identify nucleic acid molecules, or primers to produce nucleic acid molecules. Probes and/or primers can be used to clone homologues of the polynucleotides of the invention from other species. Furthermore, hybridization techniques known in the art can also be used to screen genomic or cDNA libraries for such homologues.

Polynucleotides and oligonucleotides of the present invention include those which hybridize under stringent conditions to one or more of the sequences provided as SEQ ID NO's: 9 and/or 10. As used herein, stringent conditions are those that (1) employ low ionic strength and high temperature for washing, for example, 0.015 M NaCl/0.0015 M sodium citrate/0.1% NaDodSO$_4$ at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid). A variant of a polynucleotide or an oligonucleotide of the invention includes molecules of varying sizes of, and/or are capable of hybridising to, the wheat genome close to that of the reference polynucleotide or oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise to the target region. In addition, variants may readily be designed which hybridise close to, for example to within 50 nucleotides, the region of the plant genome where the specific oligonucleotides defined herein hybridise. In particular, this includes polynucleotides which encode the same polypeptide or amino acid sequence but which vary in nucleotide sequence by redundancy of the genetic code. The terms "polynucleotide variant" and "variant" also include naturally occurring allelic variants.

Nucleic Acid Constructs

The present invention includes nucleic acid constructs comprising the polynucleotides of the invention, and vectors and host cells containing these, methods of their production and use, and uses thereof. The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In preferred embodiments of the present invention, the cis-acting sequence is an activator sequence that enhances or stimulates the expression of an expressible genetic sequence.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the genes from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, such as a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of an organism such as a plant. The term constitutive as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of, for example, the plant, such as, for example, endosperm, embryo, leaves, fruit, tubers or root. In a preferred embodiment, a promoter is expressed selectively or preferentially in leaves and/or stems of a plant, preferably a cereal plant. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the plastid, cytosol, vacuole, or apoplastic space may be achieved by the inclusion in the structure of the gene product of appropriate signals, eg. a signal peptide, for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in, for example, a plant. Typically, the promoter is expressed at a level 10-fold higher in the specific tissue or organ than in other tissues or organs.

In an embodiment, the promoter is a stem-specific promoter or a promoter which directs gene expression in an aerial part of the plant (green tissue specific promoter) such as a ribulose-1,5-bisphosphate carboxylase oxygenase (RUBISCO) promoter.

Examples of stem-specific promoters include, but are not limited to those described in U.S. Pat. No. 5,625,136, and Bam et al. (2008).

The promoters contemplated by the present invention may be native to the host plant to be transformed or may be derived from an alternative source, where the region is functional in the host plant. Other sources include the Agrobacterium T-DNA genes, such as the promoters of genes for the biosynthesis of nopaline, octapine, mannopine, or other opine promoters, tissue specific promoters (see, e.g., U.S. Pat. No. 5,459,252 and WO 91/13992); promoters from viruses (including host specific viruses), or partially or wholly synthetic promoters. Numerous promoters that are functional in mono- and dicotyledonous plants are well known in the art (see, for example, Greve, 1983; Salomon et al., 1984; Garfinkel et al., 1983; Barker et al., 1983); including various promoters isolated from plants and viruses such as the cauliflower mosaic virus promoter (CaMV 35S, 19S). Non-limiting methods for assessing promoter activity are disclosed by Medberry et al. (1992, 1993), Sambrook et al. (1989, supra) and U.S. Pat. No. 5,164,316.

Alternatively or additionally, the promoter may be an inducible promoter or a developmentally regulated promoter which is capable of driving expression of the introduced polynucleotide at an appropriate developmental stage of the, for example, plant. Other cis-acting sequences which may be employed include transcriptional and/or translational enhancers. Enhancer regions are well known to persons skilled in the art, and can include an ATG translational initiation codon and adjacent sequences. When included, the initiation codon should be in phase with the reading frame of the coding sequence relating to the foreign or exogenous polynucleotide to ensure translation of the entire sequence if it is to be translated. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

The nucleic acid construct of the present invention may comprise a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal functions for addition of polyadenylic acid tracts to the 3' end of a mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from an octopine synthase (ocs) gene or nopaline synthase (nos) gene of Agrobacterium tumefaciens (Bevan et al., 1983). Suitable 3' non-translated sequences may also be derived from plant genes such as the ribulose-1,5-bisphosphate carboxylase (ssRUBISCO) gene, although other 3' elements known to those of skill in the art can also be employed.

As the DNA sequence inserted between the transcription initiation site and the start of the coding sequence, i.e., the untranslated 5' leader sequence (5'UTR), can influence gene expression if it is translated as well as transcribed, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi (1987).

Vectors

The present invention includes use of vectors for manipulation or transfer of genetic constructs. By "chimeric vector" is meant a nucleic acid molecule, preferably a DNA molecule derived, for example, from a plasmid, bacteriophage, or plant virus, into which a nucleic acid sequence may be inserted or cloned. A vector preferably is double-stranded DNA and contains one or more unique restriction sites and may be capable of autonomous replication in a defined host cell including a target cell or tissue or a progenitor cell or tissue thereof, or capable of integration into the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, pBS-derived vectors, or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP 275957, a gene encoding a 5-enolshikimate-3-phosphate synthase (EPSPS) conferring tolerance to N-phosphonomethylglycine as, for example, described by Hinchee et al. (1988), a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., 1985), which may be employed in calcium-sensitive bioluminescence detection; a green fluorescent protein gene (Niedz et al., 1995) or derivatives thereof; a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Preferably, the nucleic acid construct is stably incorporated into the genome of, for example, the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which includes at least one polynucleotide molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

The level of a protein of the invention may be modulated by increasing the level of expression of a nucleotide sequence that codes for the protein in a plant cell, or decreasing the level of expression of a gene encoding the protein in the plant, leading to modified pathogen resistance. The level of expression of a gene may be modulated by altering the copy number per cell, for example by introducing a synthetic genetic construct comprising the coding sequence and a transcriptional control element that is operably connected thereto and that is functional in the cell. A plurality of transformants may be selected and screened for those with a favourable level and/or specificity of transgene expression arising from influences of endogenous sequences in the vicinity of the transgene integration site. A favourable level and pattern of transgene expression is one which results in a substantial modification of pathogen resistance or other phenotype. Alternatively, a population of mutagenized seed or a population of plants from a breeding program may be screened for individual lines with altered pathogen resistance or other phenotype associated with pathogen resistance.

Recombinant Cells

Another embodiment of the present invention includes a recombinant cell comprising a host cell transformed with one or more recombinant molecules of the present invention, or progeny cells thereof. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred host cells are plant cells, more preferably cells of a cereal plant, more preferably barley or wheat cells, and even more preferably a wheat cell.

Transgenic Plants

The term "plant" as used herein as a noun refers to whole plants and refers to any member of the Kingdom Plantae, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, cotyledons, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are cotyledon, embryo and embryo axis. The invention accordingly includes plants and plant parts and products comprising these.

As used herein, the term "seed" refers to "mature seed" of a plant, which is either ready for harvesting or has been harvested from the plant, such as is typically harvested commercially in the field, or as "developing seed" which occurs in a plant after fertilisation and prior to seed dormancy being established and before harvest.

A "transgenic plant" as used herein refers to a plant that contains a nucleic acid construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants".

A "non-transgenic plant" is one which has not been genetically modified by the introduction of genetic material by recombinant DNA techniques. In a preferred embodiment, the transgenic plants are homozygous for each and every gene that has been introduced (transgene) so that their progeny do not segregate for the desired phenotype.

As used herein, the term "compared to an isogenic plant", or similar phrases, refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein.

Transgenic plants, as defined in the context of the present invention include progeny of the plants which have been genetically modified using recombinant techniques, wherein the progeny comprise the transgene of interest. Such progeny may be obtained by self-fertilisation of the primary transgenic plant or by crossing such plants with another plant of the same species. This would generally be to modulate the production of at least one protein defined herein in the desired plant or plant organ. Transgenic plant parts include all parts and cells of said plants comprising the transgene such as, for example, cultured tissues, callus and protoplasts.

Plants contemplated for use in the practice of the present invention include both monocotyledons and dicotyledons. Target plants include, but are not limited to, the following: cereals (for example, wheat, barley, rye, oats, rice, maize, sorghum and related crops); beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape or other Brassicas, mustard, poppy, olives, sunflowers, safflower, flax, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers). Preferably, the plant is a cereal plant, more preferably wheat, rice, maize, triticale, oats, sorghum or barley, even more preferably wheat.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaerococcum, T. vavilovii*, and interspecies cross thereof. A preferred species of hexaploid wheat is *T. aestivum* ssp *aestivum* (also termed "breadwheat"). Tetraploid wheat includes *T. durum* (also referred to herein as durum wheat or *Triticum turgidum* ssp. durum), *T. dicoccoides, T. dicoccum, T. polonicum*, and interspecies cross thereof. In addition, the term "wheat" includes potential progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. Particularly preferred progenitors are those of the A genome, even more preferably the A genome progenitor is *T. monococcum*. A wheat cultivar for use in the present invention may belong to, but is not limited to, any of the above-listed species. Also encompassed are plants that are produced by conventional techniques using *Triticum* sp. as a parent in a sexual cross with a non-*Triticum* species (such as rye [*Secale cereale*]), including but not limited to Triticale.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

Transgenic plants, as defined in the context of the present invention include plants (as well as parts and cells of said plants) and their progeny which have been genetically modified using recombinant techniques to cause production of at least one polypeptide of the present invention in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

In a preferred embodiment, the transgenic plants are homozygous for each and every gene that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

As used herein, the "other genetic markers" may be any molecules which are linked to a desired trait of a plant. Such markers are well known to those skilled in the art and include molecular markers linked to genes determining traits such disease resistance, yield, plant morphology, grain quality, dormancy traits, grain colour, gibberellic acid content in the seed, plant height, flour colour and the like. Examples of such genes are the stripe rust resistance genes Yr10 or Yr17, the nematode resistance genes such as Cre1 and Cre3, alleles at glutenin loci that determine dough strength such as Ax, Bx, Dx, Ay, By and Dy alleles, the Rht genes that determine a semi-dwarf growth habit and therefore lodging resistance.

Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. Nos. 4,945,050 and 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. A particle delivery system suitable for use with the present invention is the helium acceleration PDS-1000/He gun is available from Bio-Rad Laboratories. For the bombardment, immature embryos or derived target cells such as scutella or calli from immature embryos may be arranged on solid culture medium.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. Nos. 5,177,010, 5,104,310, 5,004,863, 5,159,135). Further, the integration of the T-DNA is a relatively precise process resulting in few rearrangements. The region of DNA to be transferred is defined by the border sequences, and intervening DNA is usually inserted into the plant genome.

*Agrobacterium* transformation vectors are capable of replication in *E. coli* as well as *Agrobacterium*, allowing for convenient manipulations as described (Klee et al., Plant DNA Infectious Agents, Hohn and Schell, (editors), Springer-Verlag, New York, (1985): 179-203). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, Breeding Methods for Cultivar Development, J. Wilcox (editor) American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., Methods for Plant Molecular Biology, Academic Press, San Diego, (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. Nos. 5,004,863, 5,159,135, 5,518,908); soybean (U.S. Pat. Nos. 5,569,834, 5,416,011); *Brassica* (U.S. Pat. No. 5,463,174); peanut (Cheng et al., 1996); and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, WO 97/048814, U.S. Pat. Nos. 5,589,617, 6,541,257, and other methods are set out in WO 99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts. The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Marker Assisted Selection

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity. This process, termed "embryo rescue", used in combination with DNA extraction at the three leaf stage and analysis of at least one Sr50 allele or variant that confers enhanced resistance to stem rust to the plant, allows rapid selection of plants carrying the desired trait, which may be nurtured to maturity in the greenhouse or field for subsequent further backcrossing to the recurrent parent.

Any molecular biological technique known in the art can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000; Langridge et al., 2001). The invention also includes the use of molecular marker techniques to detect polymorphisms linked to alleles of the (for example) Sr50 gene which confers enhanced resistance to stem rust. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al. (2001).

In an embodiment, a linked loci for marker assisted selection is at least within 1 cM, or 0.5 cM, or 0.1 cM, or 0.01 cM from a gene encoding a polypeptide of the invention.

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (M. J. McPherson and S. G Moller (editors), BIOS Scientific Publishers Ltd, Oxford, (2000)). PCR can be performed on cDNA obtained from reverse transcribing mRNA isolated from plant cells expressing a Sr50 gene or allele which confers enhanced resistance to stem rust. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al., (supra) and Sambrook et al., (supra). Sequencing can be carried out by any suitable method, for example, dideoxy sequencing, chemical sequencing or variations thereof. Direct sequencing has the advantage of determining variation in any base pair of a particular sequence.

Tilling

Plants of the invention can be produced using the process known as TILLING (Targeting Induced Local Lesions IN Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique.

TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Plant/Grain Processing

Grain/seed of the invention, preferably cereal grain and more preferably wheat grain, or other plant parts of the invention, can be processed to produce a food ingredient, food or non-food product using any technique known in the art.

In one embodiment, the product is whole grain flour such as, for example, an ultrafine-milled whole grain flour, or a flour made from about 100% of the grain. The whole grain flour includes a refined flour constituent (refined flour or refined flour) and a coarse fraction (an ultrafine-milled coarse fraction).

Refined flour may be flour which is prepared, for example, by grinding and bolting cleaned grain such as wheat or barley grain. The particle size of refined flour is described as flour in which not less than 98% passes through a cloth having openings not larger than those of woven wire cloth designated "212 micrometers (U.S. Wire 70)". The coarse fraction includes at least one of: bran and germ. For instance, the germ is an embryonic plant found within the grain kernel. The germ includes lipids, fiber, vitamins, protein, minerals and phytonutrients, such as flavonoids. The bran includes several cell layers and has a significant amount of lipids, fiber, vitamins, protein, minerals and phytonutrients, such as flavonoids. Further, the coarse fraction may include an aleurone layer which also includes lipids, fiber, vitamins, protein, minerals and phytonutrients, such as flavonoids. The aleurone layer, while technically considered part of the endosperm, exhibits many of the same characteristics as the bran and germ and therefore is typically removed with the bran and germ during the milling process. The aleurone layer contains proteins, vitamins and phytonutrients, such as ferulic acid.

Further, the coarse fraction may be blended with the refined flour constituent. The coarse fraction may be mixed with the refined flour constituent to form the whole grain flour, thus providing a whole grain flour with increased nutritional value, fiber content, and antioxidant capacity as compared to refined flour. For example, the coarse fraction or whole grain flour may be used in various amounts to replace refined or whole grain flour in baked goods, snack products, and food products. The whole grain flour of the present invention (i.e.-ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In further embodiments, enzymes found within the bran and germ of the whole grain flour and/or coarse fraction are inactivated in order to stabilize the whole grain flour and/or coarse fraction. Stabilization is a process that uses steam, heat, radiation, or other treatments to inactivate the enzymes found in the bran and germ layer. Flour that has been stabilized retains its cooking characteristics and has a longer shelf life.

In additional embodiments, the whole grain flour, the coarse fraction, or the refined flour may be a component (ingredient) of a food product and may be used to product a food product. For example, the food product may be a bagel, a biscuit, a bread, a bun, a croissant, a dumpling, an English muffin, a muffin, a pita bread, a quickbread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In alternative embodiments, the whole grain flour, refined flour, or coarse fraction may be a component of a nutritional supplement. For instance, the nutritional supplement may be a product that is added to the diet containing one or more additional ingredients, typically including: vitamins, minerals, herbs, amino acids, enzymes, antioxidants, herbs, spices, probiotics, extracts, prebiotics and fiber. The whole grain flour, refined flour or coarse fraction of the present invention includes vitamins, minerals, amino acids, enzymes, and fiber. For instance, the coarse fraction contains a concentrated amount of dietary fiber as well as other essential nutrients, such as B-vitamins, selenium, chromium, manganese, magnesium, and antioxidants, which are essential for a healthy diet. For example 22 grams of the coarse fraction of the present invention delivers 33% of an individual's daily recommend consumption of fiber. The nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients. The supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage, this embodiment may be particularly attractive as a fiber supplement for children.

In an additional embodiment, a milling process may be used to make a multi-grain flour or a multi-grain coarse fraction. For example, bran and germ from one type of grain may be ground and blended with ground endosperm or whole grain cereal flour of another type of cereal. Alternatively bran and germ of one type of grain may be ground and blended with ground endosperm or whole grain flour of another type of grain. It is contemplated that the present invention encompasses mixing any combination of one or more of bran, germ, endosperm, and whole grain flour of one or more grains. This multi-grain approach may be used to make custom flour and capitalize on the qualities and nutritional contents of multiple types of cereal grains to make one flour.

It is contemplated that the whole grain flour, coarse fraction and/or grain products of the present invention may be produced by any milling process known in the art. An exemplary embodiment involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like. After grinding, the grain is discharged and conveyed to a sifter. Further, it is contemplated that the whole grain flour, coarse fraction and/or grain products of the present invention may be modified or enhanced by way of numerous other processes such as: fermentation, instantizing, extrusion, encapsulation, toasting, roasting, or the like.

Malting

A malt-based beverage provided by the present invention involves alcohol beverages (including distilled beverages)

and non-alcohol beverages that are produced by using malt as a part or whole of their starting material. Examples include beer, happoshu (low-malt beer beverage), whisky, low-alcohol malt-based beverages (e.g., malt-based beverages containing less than 1% of alcohols), and non-alcohol beverages.

Malting is a process of controlled steeping and germination followed by drying of the grain such as barley and wheat grain. This sequence of events is important for the synthesis of numerous enzymes that cause grain modification, a process that principally depolymerizes the dead endosperm cell walls and mobilizes the grain nutrients. In the subsequent drying process, flavour and colour are produced due to chemical browning reactions. Although the primary use of malt is for beverage production, it can also be utilized in other industrial processes, for example as an enzyme source in the baking industry, or as a flavouring and colouring agent in the food industry, for example as malt or as a malt flour, or indirectly as a malt syrup, etc.

In one embodiment, the present invention relates to methods of producing a malt composition. The method preferably comprises the steps of:

(i) providing grain, such as barley or wheat grain, of the invention, (ii) steeping said grain, (iii) germinating the steeped grains under predetermined conditions and (iv) drying said germinated grains.

For example, the malt may be produced by any of the methods described in Hoseney (Principles of Cereal Science and Technology, Second Edition, 1994: American Association of Cereal Chemists, St. Paul, Minn.). However, any other suitable method for producing malt may also be used with the present invention, such as methods for production of specialty malts, including, but limited to, methods of roasting the malt.

Malt is mainly used for brewing beer, but also for the production of distilled spirits. Brewing comprises wort production, main and secondary fermentations and post-treatment. First the malt is milled, stirred into water and heated. During this "mashing", the enzymes activated in the malting degrade the starch of the kernel into fermentable sugars. The produced wort is clarified, yeast is added, the mixture is fermented and a post-treatment is performed.

EXAMPLES

Example 1. Materials and Methods

Plant Material and Growth Conditions

Plants of two wheat lines containing independent Sr50 introgressions, Gabo1BL.1RS and Gabo1DL.1RS-DR.A1, and of the mutants M2 (00.002), M7 (00.007) and M13 (01.013) derived from these lines by γ-irradiation and ethyl methanesulfonate (EMS) treatment were used in the experiments described herein. These lines were as described by Rogowosky et al. (1991) and Mago et al. (2004). The Gabo1BL.1RS translocation was backcrossed five generations into wheat plants of the cultivar Federation to generate the resistance line Federation*5/Gabo1BL.1RS-1-1 containing Sr50 in the absence of the Gabo background genes. Plants of the Gabo1BL.1RS line were resistant to North American and African Pgt rust isolates by the presence of the Sr50 resistance gene.

*Nicotiana benthamiana* plants were grown in a growth chamber at 22° C. with a 16 hours light period, 8 hours dark per 24 hours.

Marker Analysis and Rust Phenotyping

Markers developed from an Mla gene-containing BAC from chromosome 5H of barley (Wei et al., 1999) and used for mutant analysis herein were as described by Mago et al. (2004). Stem rust phenotyping and mutant screening were done on 1 week old seedlings with *Puccinia graminis* f sp *tritici* (Pgt) race 98-1 2,3,5,6 (Sydney University culture accession 279) as described in Mago et al. (2009). To differentiate between Sr50 and Sr31, plants were phenotyped with Pgt races TTKSK (Ug99), TTKST and 98-1,2,3,5,7+50 (Sydney University culture accession 632). Transgenic plants were also phenotyped for leaf rust and stripe rust responses by inoculating seedlings with *P. triticina* pathotype 104-2,3,(6),(7),11 (Sydney University culture accession 423) and *P. striiformis* f. sp. *tritici* pathotype 110 E143A+ (Sydney University culture accession 444), respectively.

For rust infection assays to distinguish Sr50 from other resistance genes with different specificities, one-week-old seedlings were inoculated with Pgt races 34-2,4,5,7,11, (Plant Breeding Institute accession #760785); 34-2,12,13, (#840552); 126-5,6,7,11, (#334), TTKSK (04KEN156/04, Ug99), TTKST (06KEN19v3, Ug99+Sr24), QFCSC (03ND76C), TPMKC (74MN1409), TRTTF (06YEM34-1), TKKTP (13GER16-1), QCMJC (07WA140-515). Plants were also inoculated with *P. triticina* race 104-2,3,(6),(7),11 (#890172) and *P. striiformis* f. sp. *tritici* race 110 E143 A+(#861725). Infection types were scored as described (McIntosh, 1995).

Generation of Genomic DNA Lambda Library

DraI-digested genomic DNA preparations from wheat plants of the line Gabo1DL.1RS were electrophoresed on a 1% agarose gel overnight and the region of the gel containing fragments of between 9-13 kb was excised and DNA extracted and purified from the gel. The resulting DNA was ligated to BamHI adaptors and cloned into an EMBL3 λ-BamHI vector (Epicentre Technologies) and packaged using the MaxPlax (Epicentre Technologies) lambda packaging extracts according to the manufacturer's instructions. The library was hybridised with a probe derived from the LRR-encoding region of Mla1 (B76: Mago et al., 2004) and positive clones were identified and sequenced.

BAC Screening and Sequence Analysis

A wheat-rye ditelosomic addition line comprising a rye chromosome 1RS carrying Sr50 in the background of wheat cv. Chinese Spring was described by Simkova et al. (2008). A BAC library was prepared from flow sorted chromosome 1RS from this ditelosomic addition line. This 1RS chromosome-specific library was screened by DNA hybridisation using the B76 probe as described below. Positive BAC clones were purified and fingerprinted using high-information content BAC fingerprinting according to standard methods. BAC DNA was prepared using a modified alkaline lysis protocol (Sinnett et al., 1998). BAC end sequencing of clones in the minimal tiling path of the contig containing Sr50 was performed using primers designed to the pIndigo BAC vector using Sanger sequencing. BAC sequences were used to design specific PCR primers. Five BAC clones were sequenced using the Roche 454 sequencing platform. Repeat sequences present in the assembled BACs were masked using the Wheat Repeats Database (wheat.pw.usda.gov/ITMI/Repeats/blastrepeats3.html). Sequence reads were assembled using Newbler v2.3. Non-repeated sequences were analysed for genes using the gene prediction softwares FGENESH (www.softberry.com) and GENSCAN (genes.mit.edu/GENSCAN.html).

PCR Amplification of Sr50 Candidates

PCR amplification of candidate rust resistance genes from Gabo 1DL.1RS-DR.A1 and various susceptible M2 mutants used primer pairs flanking the genes. Amplified sequences were compared for nucleotide variations using multiple sequence alignment (CLUSTAL-European Bioinformatics Institute-www.edi.ac.uk/Tools/sequence.html). RNA extraction, cDNA synthesis, 5' and 3' RACE (rapid amplification of cDNA ends) were done using the methods described in Periyannan et al. (2013). Primers designed at the predicted 5' and 3' termini of Sr50 transcripts were used for RT-PCR analysis. For 5'- and 3'-RACE, primers designed at the 5' and 3' coding regions were used as the gene-specific primers.

Wheat Transformation

Two genomic DNA constructs each comprising Sr50 and therefore encoding the Sr50 polypeptide were generated. The first contained a 7.5 kb fragment including 2.4 kbp upstream and 1.38 kbp downstream regions relative to the protein coding region of ScRGA1-A in the binary vector pVecBarII. This fragment was amplified from Gabo1DL.1RS genomic DNA using primers F1-R1 followed by nested primers F2-R2 listed in Table 2 with PfuUltra II Fusion HS DNA Polymerase (Agilent Technologies) under the manufacturer's recommended conditions. The second construct contained a 9.8 kbp NotI fragment from BAC clone 180C18 including 4.2 kbp upstream and 1.88 kbp downstream regions relative to the protein coding region and inserted into the binary vector pVecNeo.

TABLE 2

Primers used for PCR amplification of Sr50, ScRGA1 candidates and BAC ends.

| Marker | Forward primer | Reverse primer |
| --- | --- | --- |
| Sr50-F1, R1 | TAGCGCTGCTCACATCCACCTC (SEQ ID NO: 17) | GATCCGCCGTTGTCGGCATTTGT (SEQ ID NO: 18) |
| Sr50-F2, R2 | ATTCATGCTTTTATACTCACTAATATC (SEQ ID NO: 19) | GGGCGTGACTGTGCTGCTT (SEQ ID NO: 20) |
| Sr50-F3 | TTCAGTGAAGTTGCCGCTGT (SEQ ID NO: 21) | |
| ScRGA1-A-VIGS | CGACAACTCCGGCAGATTTA (SEQ ID NO: 22) | GACAAGGATCGATAGTAATTGGTTC (SEQ ID NO: 23) |
| ScRGA1-A RT-qPCR | TCCACCTAAGGTACCTTGATCTAC (SEQ ID NO: 24) | GAGTTGGAACCACCTTATA (SEQ ID NO: 25) |
| ScRGA1-A RT-PCR | GCGCTGCCTGGAATAAGGTC (SEQ ID NO: 26) | TAAAACAAAGCCGCGGAAAAC (SEQ ID NO: 27) |
| RACE 5p, 3p | GATTCCTGCCTTTCTTAAACAAGCCGA (SEQ ID NO: 28) | TCGGCATGATGTCTTTGTTCG (SEQ ID NO: 29) |
| p2D7-F-end | GGCGGGCTGCTAGTATTTCC (SEQ ID NO: 30) | GCCATCGGATCTGGAGAGAA (SEQ ID NO: 31) |
| p2D7-R-end | CGTTGCAATGATGTACCATACG (SEQ ID NO: 32) | ACCGAGCTCGTGTGCTCAA (SEQ ID NO: 33) |
| p2E7-F-end | CAACAAGACGCACACCACCT (SEQ ID NO: 34) | GTGCAGTTGCAGAGGACCTG (SEQ ID NO: 35) |
| p2C2-F-end | TTCGCAGGTTCATCATGGTC (SEQ ID NO: 36) | CTCCCGAATTGGAAAGTGGA (SEQ ID NO: 37) |
| p2C2-F-end | CCTTGGCCTTTAGCTTGTGG (SEQ ID NO: 38) | TTGCCGGAAGCAAGAACTTT (SEQ ID NO: 39) |
| p1F7-F-end | CGGAGTGTTTGGATGAAAGG (SEQ ID NO: 40) | CCGATCCAGGGGATATAGGT (SEQ ID NO: 41) |
| p1F7-R-end | CTTCGTTAGGAATGGCAGGT (SEQ ID NO: 42) | CATGCCTGATTCAATGTTGC (SEQ ID NO: 43) |
| p2B8-F-end | GCACGCATGCATGTAGTTGA (SEQ ID NO: 44) | GGGAAGCTCCTGGTTTGTTG (SEQ ID NO: 45) |
| p2B8-R-end | ATCCGTGGGAGCTGTAGGTG (SEQ ID NO: 46) | AGATGGATTGGGCTGTGGAT (SEQ ID NO: 47) |
| p2C8-F-end | CGCTCAGTTTGCCGAAAAG (SEQ ID NO: 48) | ATCGGAGTCGTCGGAGAGAG (SEQ ID NO: 49) |
| p2C8-R-end | GGTCCCTTGCTCGTGAGTTC (SEQ ID NO: 50) | TGTGATGGTGATGCTTGTGC (SEQ ID NO: 51) |
| p2C7-F-end | TCTGAAGCCGGTCGAGTCTTC (SEQ ID NO: 52) | GGGAGTACTAGTCTCGCATCA (SEQ ID NO: 53) |

TABLE 2-continued

Primers used for PCR amplification of Sr50, ScRGA1 candidates and BAC ends.

| Marker | Forward primer | Reverse primer |
|---|---|---|
| p2C7-R-end | CATGGCTGCCACTCTCAAAG (SEQ ID NO: 54) | TCACGCACGTCAAGTCAAAA (SEQ ID NO: 55) |
| p2A3-F-end | TGGTACTGTGAAAGCGATTCTTATC (SEQ ID NO: 56) | GACGGCAAGATGGAGCAAGGA (SEQ ID NO: 57) |
| pIndigoBAC5 | GGATGTGCTGCAAGGCGATTAAGTTGG (SEQ ID NO: 58) | CTCGTATGTTGTGTGGAATTGTGAGC (SEQ ID NO: 59) |

Binary vectors pVecNeo and pVecBarII are derivatives of pWBvec8 (Wang et al., 1998) in which the 35S promoter::hygromycin resistance gene was replaced with a 35S promoter::NPTII selectable marker gene derived from pCMneoSTL2 (Maas et al., 1997), or the bialaphos resistance gene (bar) coding region as a selection marker for plant transformation.

Transformation of the stem rust susceptible wheat cultivar Fielder was done using *Agrobacterium tumefaciens* strain GV3101 (pMP90) as described (Ishida et al., 2014; Richardson et al., 2014). T0 transformants and T1 progeny plants, including both plants which comprised the transgene and segregants that lacked it as negative control plants, were tested for rust response with Pgt strain 98-1,2,3,5,6 as described above. The presence of the transgene and/or selectable marker gene was detected by Southern blot hybridization as described (Mago et al., 2004). For this, a PCR amplified sequence from the 5' end of Sr50 was used as a gene-specific probe. Alternatively, transgene-specific PCR could have been carried out to detect the transgene.

Yeast Two-Hybrid Analysis

Yeast two-hybrid experiments were performed in *Saccharomyces cerevisiae* reporter strain Hf7c. The cDNAs encoding full length or truncated Sr50 were cloned at EcoRI-XhoI sites of pGBKT7 and pGADT7 (Clontech). Yeast transformation was performed according to Gietz and Woods (2002) with co-transformants selected on SD media lacking leucine and tryptophan. The interaction analysis was performed by plating the yeast cells on media lacking leucine, tryptophan and histidine and incubating the plates at 30° C. for 3-4 days.

Constructs for in Planta Expression

All PCR products used for cloning were generated using Phusion High-Fidelity DNA Polymerase (Finnzymes) with primers listed in Table 2. Molecular cloning was performed using Gateway recombination (Life Technologies) or Quickchange Site-Directed Mutagenesis (Stratagene). For the creation of Gateway entry clones, pDONR207 (Life Technologies) was used. For *Agrobacterium tumefaciens* (agro) infiltration experiments, pBIN19-35S::GTW:3HA, pBIN19-35S::GTW:CFP (Cesari et al. 2014), pAM-PAT-35s::GTW: YFP:NLS; pAM-PAT-35s::GTW:YFP:nls; pAM-PAT-35s:: GTW:YFPv: NES and pAM-PAT-35s::GTW:YFPv:nes were used.

A functional NES from HIV Rev (NES: LQLPPLERLTL; SEQ ID NO:15) and non-functional nes (LQAPPAERATL; SEQ ID NO:16) (Wen et al., 1995) were introduced in the pAM-PAT-35s-GWY-YFPv vector (Bernoux et al., 2008) at the C-terminus end of the YFPv. YFPv-NES/nes fragments were PCR-amplified using a forward primer containing a 3' SmaI site and a reverse primer containing a 5' XbaI site as well as the NES or nes sequence. Corresponding PCR products were ligated into pAM-PAT-35s-GWY-YFPv cut with SmaI/XbaI to replace the original YFPv by YFPv-NES/nes fusions.

Transient Protein Expression and Cell Death Assays in *N. benthamiana*

For *Agrobacterium*-mediated transformation of *N. benthamiana* leaf cells, cultures of *Agrobacterium* strain GV3101 transformed with the genetic construct pMP90 were grown in Luria-Bertani liquid medium containing 50 mg ml-1 rifampicin, 15 mg ml-1 gentamycin and 25 mg ml-1 kanamycin at 28° C. for 24 hours. The constructs providing for expression of NLS-, NES-, nls- and nes-fused proteins were transformed in *A. tumefaciens* strain GV3103 and grown as described above with addition of 25 mg ml-1 of carbenicillin. Bacteria were harvested by centrifugation, resuspended in infiltration medium (10 mM IVIES pH 5.6, 10 mM MgCl2 and 150 µM acetosyringone) to an OD600 nm ranging from 0.5 to 1, and incubated for 2 hours at room temperature before leaf infiltration. The infiltrated plants were incubated in growth chambers under controlled conditions for co-immunoprecipitation experiments and cell death assays. For documentation of cell death, leaves were photographed 3-5 days after infiltration.

Confocal Microscopy

*N. benthamiana* epidermal cells were observed under a confocal microscope (TCS SP8; Leica) 20 hours after infiltration. Specific YFP fluorescence was detected using the following spectral settings: excitation, 488 nm; detection, 515-545 nm. Auto-fluorescence of the chloroplasts was detected at 670-730 nm. All images were acquired using a water immersion lens (HC PL APO 63x/1.20 W CORR CS2, Leica).

Protein Extraction Western Blot and Co-Immunoprecipitation

Protein extraction from *N. benthamiana* leaves and co-immunoprecipitation experiments were performed as described by Cesari et al. (2014). For immunoblot analysis, proteins were separated by SDS-PAGE and transferred to a nitrocellulose membrane (Pall). Membranes were blocked in 5% skimmed milk and probed with anti-HA or anti-Myc mouse monoclonal antibodies (Roche), followed by goat anti-mouse antibodies conjugated with horseradish peroxidase (Pierce). Labelling was detected using the SuperSignal West Pico or Femto chemiluminescence kits (Pierce). Membranes were stained with Ponceau S to confirm equal loading.

Example 2. The Sr50 Gene Encodes a Unique Resistance Specificity Effective Against Ug99

To determine whether the fungal resistance gene Sr50 conferred the same resistance specificity as, or a different resistance specificity to, Sr31, wheat plants of defined lines carrying one or other of these genes, or none of these genes as a control, were tested for their reaction to a set of Pgt strains of different virulence specificities as described in Example 1. Mutant plants carrying mutations in the Sr50 gene were also tested; these were expected to be susceptible to Ptg strains carrying the avirulence gene having Sr50 specificity. The data from the inoculation tests are summarised in Table 3.

TABLE 3

Infection types produced by lines containing Sr31 and Sr50 lines when inoculated with Pgt strain TTKSK (Ug99).

| Plant name/genotype | Race of Pgt inoculum | | | |
|---|---|---|---|---|
| | QFCS | TPMK | TTKSK | TTKST |
| Federation | 3+ | 4 | 4 | 4 |
| Federation*4/Kavkaz Sr31 | 1 | 1+ | 4 | 4 |
| Federation*4/Kavkaz -sr31 (02.010-2) | 3+ | 4 | 4 | 4 |
| Gabo | 1−; | 2++ | 2 | 2 |
| Gabo 1DL.1RS- DR.A1 Sr50 | ;1− | ;1 | 1 | 1 |
| Gabo 1BL.1RS Sr50 | ;1 | 1 | 1 | 1 |
| Gabo 1BL.1RS Sr50 (M7) | 0; | 2++ | 2 | 2 |

The results showed that while Sr31 was, as expected, ineffective in providing resistance to Ptg strains Ug99 (TTKSK) and its derivative TTKST, the Sr50 gene in the genetic background of the wheat variety Gabo provided effective resistance to these strains, yielding an infection type 1 (Table 3). A mutant of Sr50 in this same genetic background (M7 in Table 3) showed a similar phenotype (infection type 2) to the Gabo parent lacking the Sr50 gene, indicating that the mutation in the Sr50 gene in the mutant inactivated the resistance gene. With some inoculations, an intermediate infection phenotype was observed in plants of these lines—this was due to the presence of other stem rust resistance genes in the Gabo background that conferred partial resistance to Ug99 derivatives.

To aid in specifically testing for the Sr50 gene, a spontaneous mutant Pgt strain with virulence for Sr50, designated 98-1,2,3,5,6+Sr50 (available from Plant Breeding Institute accession #130176) was isolated from a single pustule observed after infection of Sr50 plants with strain 98-1,2,3,5,6 (#781219). Infection of a set of differential wheat lines, each containing different R genes, confirmed that the mutant Pgt strain was identical to the parental isolate but with virulence to Sr50. This pair of Pgt strains could therefore be used to specifically detect the presence of Sr50.

The genotypic and phenotypic difference between the Sr31 and Sr50 resistance genes in plants was further confirmed by inoculation of the plants with the parental Ptg and the mutant Ptg derivative, 98-1,2,3,5,6+Sr50. The parental Ptg strain 98-1,2,3,5,6 was virulent on plants of cultivar Gabo, this cultivar having no resistance genes against this Ptg strain, and avirulent on plants containing individually Sr31 or Sr50. In contrast, the mutant Ptg 98-1,2,3,5,6+Sr50 retained avirulence to Sr31 but was virulent to Sr50 (Table 4). Furthermore, the parental strain and the mutant Ptg were both avirulent to plants containing Sr33, a wheat ortholog of Sr50 (see below), as well as to the $Sr^{Amigo}$ (1AL.1RS) present in plants of variety Amigo. Therefore, it was concluded that the mutant Sr50 Ptg strain had lost activity of the Sr50 avirulence gene (AvrSr50), and that the Sr50 resistance gene encoded a unique resistance specificity which could be distinguished from the other 1RS located stem rust resistance genes. It was also concluded that Sr50 could be distinguished from the other stem rust resistance genes by inoculation of the plants with different Ptg races.

TABLE 4

Comparative infection types produced by various lines when infected with Pgt race 98-1, 2 , 3, 5, 6 and its Sr50-mutant.

| | Ptg strain | |
|---|---|---|
| Plant name/genotype | 98-12357 | 98-12357 + Sr50 |
| Westonia (Sr33) | 2− | 2 |
| Gabo 1DL.1RS-DR.A1 (Sr50) | 12= | 3+ |
| Gabo 1BL.1RS (Sr50) | 12= | 3+ |
| Mildress (Sr31) | 12= | ;1 |
| Amigo (1AL.1RS) derivative ($Sr^{Amigo}$) | 2 − 2 | 2 − 2 |

Example 3. Physical Mapping of the Sr50 Locus

Mago et al. (2004) observed that a DNA hybridisation probe designated B76, derived from the LRR coding region of the barley powdery mildew resistance gene Mla1, detected at least 17 hybridising fragments in DraI-restricted genomic DNA at the Sr50 locus of wheat and that several Sr50 mutants with small deletions had lost just two of these fragments of about 10 and 12 kbp. In an attempt to isolate the Sr50 gene, a lambda phage genomic DNA library was prepared as described in Example 1 from plants of the Sr50 line Gabo1BL.1RS and screened. The lambda library containing DraI fragments that ranged in size from 9 to 13 kbp. Using the B76 hybridisation probe, six unique clones were isolated from the library and selected for further analysis (FIG. 1).

Sequence analysis showed that all of these encoded Mla-related CC-NB-LRR sequences. Three contained various truncations or frameshifts and therefore could not encode full length CC-NB-LRR proteins and two were sequences with some similarity to the LRR region of the B76 probe. The sixth, clone 5 (FIG. 1), contained a mostly full length gene with no internal interruptions of the reading frame but was truncated at a DraI site in the LRR-encoding region and therefore was missing the 3' end of the predicted gene.

To improve physical coverage of the deleted region including Sr50, probe B76 was then used to screen a 1RS chromosome-specific BAC library constructed from a Sr50-containing wheat-rye ditelosomic addition line, as described in Example 1. This probe identified 175 BAC clones. High-information content BAC fingerprinting grouped these into 6 non-overlapping contigs based on 2, 3, 11, 24, 71 and 72 clones. Eighteen BACs forming the minimum tiling path of these contigs were screened by PCR using primers specific to the Mla homolog in lambda clone 5. By this, BAC p2D7 (FIG. 2) was identified as containing this sequence. The PCR product was also amplified from four BAC clones overlapping p2D7, p2E7 p2B12, p2B9 and p1H3, confirming the presence of the candidate gene in this contig (FIG. 2).

To map the Sr50 gene and its surrounding locus onto the physical contig, BACs forming the minimum tiling path from the contig were end-sequenced and PCR markers developed from the BAC ends were used to screen the Sr50 parent and the deletion mutant M2 (00.002). This analysis revealed that the deletion in mutant M2, and therefore the Sr50 gene, was wholly contained in the region spanned by 3 BAC clones, namely p2D7, p2A3 and p2C2, with the proximal and distal ends of p2D7 and p2C2 respectively retained (FIG. 2).

These three BAC clones spanning the deletion, as well as BAC p2E7, which was wholly contained in p2D7 and the adjacent BAC, p2C7, were sequenced. Annotation of the nucleotide sequences from this 250 kbp region identified six Mla-related NB-LRR protein coding regions (open reading frames) within the deleted region, and a single NB-LRR ORF in the adjacent region on BAC p2C7 (FIG. 2). These were designated as ScRGA1-A to ScRGA1-G. The ORFs varied in length from 3.6 to 12.1 kb and each had either one or two predicted introns. They encoded predicted polypeptides in the range of 944 to 974 amino acids. A single copy of a chymotrypsin inhibitor (Ci) gene, a homolog of which was also present at the Mla locus of barley, was also detected within the deleted region. This was consistent with previous DNA hybridization analyses which identified 4 copies of a related Ci gene on 1RS, only one of which was deleted in the interstitial deletion mutants (Mago et al., 2004). The amino acid sequence encoded by the lambda clone 5 was 100% identical to the ScRGA1-A amino acid sequence, but the other lambda clones identified as described above did not correspond to any of the other ScRGA1 genes in the BAC contig.

Example 4. Identification of the Sr50 Gene

In addition to the M2 deletion mutant described above, the inventors had previously isolated several EMS-derived Sr50 gene mutants that retained all of the B76-hybridising fragments and therefore possibly represented point mutations of Sr50 (Mago et al. 2004). Two mutant plants, M7 (00.007) and M13 (01.013), were recovered and progeny plants produced. A cross between M7 and M13 plants produced no resistant progeny indicating they carried a mutation in the same gene. The six ScRGA1 genes identified within the M2 deletion as described above were amplified from M7 and from M13 as well as from Gabo1DL.1RS DR.A1 and sequenced. One gene candidate of the six, namely ScRGA1-A, contained a single base pair deletion in M7 and a 23 bp deletion in M13. Both mutations resulted in translational frame shifts which led to premature stop codons in the ORF (FIG. 3). All the other candidate genes were identical in sequence in the wild-type plants and the mutants M7 and M13. The identification of multiple, independent mutations in the same coding region indicated that the ScRGA1-A coding region corresponded to the Sr50 gene. This conclusion was confirmed by transformation experiments (see below).

Example 5. Transformation of Wheat with Sr50 Genes

To confirm that ScRGA1-A conferred Sr50 resistance, two constructs containing this gene were used to transform plants of the stem rust-susceptible wheat cultivar Fielder as described in Example 1. The first construct, pVecBarSr50 (SEQ ID NO: 12), contained a 7.9 kb PCR-amplified genomic sequence of ScRGA1-A including the native promoter and terminator (2.4 and 1.4 kbp, respectively) within the T-DNA. The second construct, pVecNeoSr50 (SEQ ID NO: 11), contained a 9.7 kb NotI genomic fragment from BAC p2D7 with larger 5' and 3' regions, within the T-DNA. Both constructs therefore contained the genomic form of ScRGA1-A including all of its introns as well as the native promoter, but linked to heterologous sequences within a chimeric T-DNA construct. The constructs were used to transform wheat and confirmed transgenic plants and their progeny tested as described in Example 1.

Independent T0 transgenic plants and T1 progeny plants containing the T-DNA from pVecBarSr50 were inoculated with Pgt strains. The transgenic plants exhibited responses to Pgt typical of Sr50-mediated resistance whereas segregant plants that lacked the transgene were as susceptible as untransformed parental plants. Likewise, T0 wheat lines transformed with pVecNeoSr50 showed resistance typical of Sr50. To confirm that the observed resistance phenotype was race specific and not due to general enhancement of defense pathways, T1 progeny of four stem rust resistant transgenic plants (lines 2, 10b, 13 and 19d) were tested for their reactions to leaf rust and stripe rust by inoculation with the strains described in Example 1.

All transgenic progeny plants were as susceptible to leaf rust and stripe rust as the non-transformed controls. Moreover, the T1 progeny populations showed a 3:1 segregation ratio (resistant:susceptible) for reaction to stem rust, indicative of Mendelian inheritance ratios for insertion of a single transgene in the nuclear genome. The combined mutational and complementation data conclusively demonstrated that the gene designated ScRGA1-A was the Sr50 resistance gene.

The experiment also proved that the gene provided rust resistance when used to transform a cereal plant. Thus, as the skilled person would appreciate, the same or similar constructs (for example with different promoter regions) can be used to produce other cereal plants (such as rice, barley, maize or sorghum) which express Sr50 resulting in resistance to one or more races *Puccinia graminis.*

Example 6. Structure of Sr50 and Comparison to Barley and Wheat Functional Mla Genes The presence of two predicted introns in the protein coding region of Sr50 was confirmed by RT-PCR and comparison of the cDNA and genomic nucleotide sequences. Rapid amplification of cDNA ends (RACE) analysis, carried out as described by Jordan et al. (2011), identified 5' and 3' UTRs of 629 and 238 bp, respectively, containing 3 additional introns (FIG. 3). Sizes of the exons and introns of Sr50 are shown in FIG. 3.

The predicted Sr50 polypeptide was 77-78% identical in amino acid sequence to polypeptides in the barley MLA protein family, some of which confer resistance to powdery mildew, not rust resistance. Phylogenetic analysis of cereal Mla homologs using their amino acid sequences placed the Sr50 protein in a clade with other ScRGA1 polypeptides as well as with the orthologous proteins TmMla1 and Sr33 from diploid wheat species, *T. monococcum* and *Ae. tauschii* (FIG. 4). The extent of amino acid sequence identity amongst ScRGA1 members ranged between 78-89% whereas the Sr50 polypeptide showed 81% and 80% identity with the TmMla1 and Sr33 amino acid sequences, respectively. The Lr1, Lr10 and Lr21 wheat leaf rust resistance proteins were highly divergent from the Mla/Sr33/Sr50 clade (FIG. 4), with sequence identities ranging from 19% to 33%, indicating a lack of relatedness with leaf rust resistance polypeptides. The leaf rust polypeptides were vastly different to the rust resistance polypeptides and could be easily distinguished. The polypeptide encoded by the only other cloned wheat stem rust resistance gene, Sr35 from *T. monococcum*, showed 48% amino acid identity with Sr50.

Example 7. Presence of Sr50 Gene and Variants in Cereals

To detect the presence of the Sr50 gene in rye, the origin species of the Sr50 gene in wheat, 114 geographically diverse rye accessions were screened by PCR with primers flanking Sr50. The PCR amplification was done using PfuUltra II Fusion HS DNA Polymerase and oligonucleotide primers F1-R1 followed by nested PCR with primers F3-R3. These reactions amplified a 4.17 kb PCR product including the entire Sr50 gene.

Amplification of Sr50 sequences occurred from only 10 of the 114 accessions, indicating the presence of a Sr50 gene or a close homolog in those 10 accessions. For five of those accessions, the amplified gene was identical to Sr50, while three of the others contained small substitutions and two were disrupted by a sequence inversion. All of these rye accessions except for Dwarf Petkus R1 showed resistance to several races of stem rust, including the Sr50-virulent mutant, indicating the presence of additional Sr genes, which may be on other chromosomes. Despite the sequence similarity of the Sr50 gene in most of these accessions, they contained diverse haplotypes of this complex locus, suggesting extensive recombination within this cluster in rye. Both of the Sr31 and stripe rust resistance Yr9 genes occur in the same 1RS region, and may also belong to this gene family. Therefore, this locus appears to be a hotspot for evolution of fungal resistance specificities in cereals, including in wheat, barley and rye.

Example 8. Functional Analysis of Sr50 Polypeptide

The Coiled-Coil Domain of MLA10, Sr33 and Sr50 is Sufficient for Induction of Cell Death Previous functional analysis of the MLA N-terminal region showed that a 225 amino acid fragment including the CC and part of the NB domains could self-associate in yeast, whereas a 160 amino acid fragment containing the CC domain alone was autoactive in signalling cell death in planta. A 120 amino acid fragment, which was a truncated CC domain, could dimerise in vitro (Maekawa et al., 2011; Bai et al., 2012).

To investigate whether the wheat and rye orthologs Sr33 and Sr50 functioned similarly to MLA and to determine the minimal functional region in cell death signalling, various N-terminal fragments of the Sr50 and Sr33 polypeptides were fused to either a C-terminal HA or CFP tag. These fusion polypeptides were transiently expressed in N. benthamiana leaf cells under the control of the 35S promoter as described in Example 1. The constructs that expressed the full CC domains of Sr33 and Sr50, namely amino acids 1-160 and 1-163, respectively, triggered a strong cell death response in the leaf cells that was visible 40 hours after agro-infiltration as a leaf tissue necrosis of the infiltrated zones.

Similar to previous reports (Makeawa et al., 2011; Bai et al., 2012), the corresponding domain form barley MLA, MLA101-160, also induced a strong cell death response that was visible within 24 hours when expressed in N. benthamiana leaf cells. Another construct made to express a positive control protein fusion, the rice autoactive CC-NB-LRR RGA4 (Cesari et al., 2014), also produced a strong cell death response, while a mutant variant of RGA4 did not cause a response in N. benthamiana leaf cells. Expression of the CC domains together with a portion of the NB domains of Sr33 (1-225), Sr50 (1-228) and MLA10 (1-225) also triggered strong cell death responses. However, the truncated CC domains of MLA10 (1-120), Sr33 (1-120) and Sr50 (1-123) fused to the HA tag did not induce cell death in N. benthamiana. Western blot analysis showed that all fusion proteins were properly expressed in the leaf cells.

Taken together, these results showed that the full CC domains of MLA10, Sr33 and Sr50 were required and sufficient for induction of cell death signalling, and although the truncated CC domain of MLA10 dimerized in solution and its crystal structure had been resolved (Maekawa et al., 2011), it was not sufficient to trigger a cell death response. These data demonstrated that the function of the CC domain in each polypeptide was to trigger the induction of cell death, which is associated with the resistance response in wheat stem cells when the pathogen is present.

The Coiled-Coil Domains of Sr33, Sr50 and Lr21 Form Homo-Complexes

Although the truncated MLA10 CC5-120 fragment was able to self-associate in solution to form a dimer, only the MLA10 CC-NB1-225 domain had been shown to self-interact when tested in a yeast two-hybrid assay (Maekawa et al., 2011). Self-interaction had not been demonstrated with the minimal active CC1-160 domain. Therefore, yeast-two-hybrid experiments were carried out to test for interaction between the truncated CC, CC and CC-NB fragments of MLA10 and Sr50. Immunoblotting showed that all the protein fragments were expressed in the yeast cells in the experiments. The results showed that the full CC domains of MLA10 and Sr50 were required for self association in yeast, whereas no interaction was detected for the truncated CC domains of these proteins.

To determine whether the active CC domains of MLA10, Sr33 and Sr50 self-associated in planta, combinations of the HA and CFP-tagged MLA10, Sr33 and Sr50 domains were co-expressed in N. benthamiana leaf cells and co-immuno-precipitation assays were performed. The CC1-284 domain of the unrelated Lr21 resistance polypeptide, which was known to be autoactive in planta, was also included in the experiment to test its ability to self-interact. The RGA4 CC domain (amino acids 1-171) fused to CFP was used as a control for binding specificity. Immunoblotting using anti-GFP and anti-HA antibodies showed that all of the polypeptides were expressed as intended, except for the MLA10 fusions, which was likely due to the more rapid cell death response induced by these polypeptides and their consequent degradation in the cells. Immunoprecipitation was used to assay for association of the co-expressed polypeptides. Immunoprecipitation with anti-GFP antibodies resulted in enrichment of all CFP-fused proteins and Sr331-160:HA, Sr501-163:HA and Lr211-284:HA specifically co-precipitated with Sr331-160:CFP, Sr501-163:CFP and Lr211-284:CFP, respectively, but not with RGA41-171:CFP. Taken together, these results showed that the CC domains of Sr33, Sr50 and Lr21 had the capability to form specific homo-complexes in planta, i.e. the could self-associate.

Cytoplasmic Localization of MLA10, Sr33 and Sr50 Coiled-Coil Domains is Required for Cell Death Induction The MLA10 full length polypeptide and its CC-NB1-225 domain have been shown to trigger cell-death signalling when localised in the cytoplasm of N. benthamiana leaf cells (Bai et al., 2012). To determine whether the shorter MLA10 CC1-160 domain, thought to be needed for cell death induction, by itself could induce cell death when localised in the cytoplasm and to test this feature for the Sr33 and Sr50 CC domains, those domains were transiently expressed in N. benthamiana fused to YFP along with a nuclear localisation signal (NLS), a mutated NLS (nls), a nuclear export signal (NES) or a mutated NES (nes). Upon expression of the YFP:NLS fused CC domains, specific YFP fluorescence was detected exclusively in the nuclei of N. benthamiana cells. In contrast, the CC domains fused to YFP:NES were effectively excluded from the nuclei, with YFP fluorescence detected in the cytosol and surrounding the nuclei only, while the mutated nls and nes variants allowed detection of YFP fluorescence in both the cytosol and the nuclei as intended. Cell death assays in N. benthamiana leaf cells revealed that forced nuclear localization of all CC domains reduced their cell-death activity. Other fusions with YFP:NES, YFP:nes or YFP:nls did not affect the cell-death inducing activity of MLA10 or Sr33 CC domains. In the case of the Sr50 CC domain, the mutant nls also showed some reduction in cell death activity relative to the NES and nes fusions. Protein expression of all constructs was verified by immunoblotting. The NES fusion constructs consistently showed lower protein accumulation. Nevertheless, these constructs gave the strongest cell death (hypersensitive response, HR) phenotype, suggesting that cell death and protein degradation processes were already activated at the time of sampling. These results indicated that cytosolic localization of those CC domains was required for cell death induction.

Example 9. Discussion

Both Powdery Mildew and Rust Resistances are Encoded by Mla Genes

The Mla gene clade of CC-NB-LRR genes, originally identified on chromosome 1HS in barley as a powdery mildew resistance gene also occurs in wheat, where orthologs include the powdery mildew resistance gene TmMla1 (Jordon et al., 2011) and the stem rust resistance gene Sr33 (Periyannan et al., 2013). The genes occur as a small gene family of about 5 members in wheat and barley. DNA gel blot analysis has shown that this family has greatly expanded to over 20 members on chromosome 1RS in rye (Mago et al., 2004). The experiments described above have now shown that the Sr50 stem rust resistance gene is a member of the rye Mla orthologous gene family.

Although the wheat stem rust resistance genes Sr33 and Sr35 were isolated previously (Periyannan et al., 2013; Saintenac et al., 2013), originating from wheat, the Sr50 gene was the first stem rust resistance gene to be cloned which originated from rye and which is effective against all known field races of Pgt including Ug99. High resolution mapping and mutation studies have also placed both Sr31 and the stripe rust resistance gene Yr9 from Petkus rye 1RS in the region homologous to Sr50 (Mago et al., 2005), suggesting that these genes may also belong to the Mla gene family. Therefore, this multi-species locus appears to be a hotspot for evolution of resistance specificities in the cereals.

Subcellular Localization of NB-LRR Proteins and Cell Death Activation

Increasing knowledge about localization of NB-LRR proteins has revealed that they can be observed and activated in a wide diversity of cellular compartments. Some are exclusively nuclear such as RRS1 (Deslandes et al., 2003; Tasset et al., 2010), whereas others like RGA4 and RGA5 are mainly localized in the cytosol (Cesari et al., 2014). Rpm1 (Gao et al., 2011), RPS2 (Axtell and Staskawicz, 2003) and RPS5 (Qi et al., 2012) are located at the plasma membrane, and the flax L6 and M proteins occur on the Golgi and tonoplast membranes, respectively (Takemoto et al., 2012). However, many show a nucleo-cytoplasmic localization such as N (Burch-Smith et al., 2007; Caplan et al., 2008), RPS4 (Wirthmueller et al., 2007), SNC1 (Cheng et al., 2009), Pik1/Pik2 (Zhai et al., 2014), Rx (Slootweg et al., 2010) and MLA10 (Shen et al., 2007).

In the case of the potato CC-NB-LRR polypeptide Rx that triggers recognition of the Potato Virus X (PVX) coat protein (CP), it was shown that CP activates Rx in the cytoplasm, and forced nuclear localization of Rx severely compromised both virus resistance and cell death (Slootweg et al., 2010; Tameling et al., 2010). However, Rx nuclear exclusion only moderately reduced PVX resistance (Slootweg et al., 2010), suggesting that the cytosolic pool was most important, although both nuclear and cytoplasmic pools of the resistance protein may have contributed to resistance signalling. Conversely, another study on MLA10 demonstrated that a nuclear localised receptor was sufficient to confer resistance to B. graminis in a transient single cell assay in barley, while a nuclear-excluded MLA10 was not (Shen et al., 2007). However, forced nuclear localisation of autoactive MLA protein variants impaired induction of cell death whereas nuclear excluded variants were sufficient to trigger resistance (Bai et al., 2012). To explain this, it has been proposed that MLA10-triggered cell death signalling and disease resistance signalling occur in different compartments (Bai et al., 2012). Alternatively, $AVR_{A10}$ recognition may occur exclusively in the nucleus, explaining the requirement for a nuclear localised receptor to confer resistance, with subsequent signalling events perhaps occurring in the cytoplasm.

Sr33 and, as demonstrated by the experiments described above, Sr50 are homologs of MLA10 and using their minimal CC signaling domains, a similar pattern of cell death induction was observed relative to that triggered by the full length MLA10 protein or the MLA10 CC-NB domain (Bai et al., 2012). Therefore, it appeared that the responses triggered by MLA10 in barley and its close wheat homologs were similar, suggesting a conserved cell death pathway triggered by different pathogens in two different cereal species.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

This application claims priority from AU 2015904976 filed 1 Dec. 2015, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotechnology 4:1087.
Axtell and Staskawicz (2003) Cell 112:369-377.
Bai et al. (2012) PLoS Pathog 8(6): e1002752. doi:10.1371/journal.ppat.1002752.
Bam et al. (2008) Proc S Afr Sug Technol Ass 81:508-512.
Barker et al. (1983) Plant Mol. Biol. 2: 235-350.

Bernoux et al. (2008) Plant Cell 20:2252-2264.
Bevan et al. (1983) Nucl. Acid Res. 11: 369-385.
Burch-Smith et al. (2007) PLoS Biol 5: e68.
Cadwell and Joyce (1992) PCR Methods Appl. 2:28-33.
Capecchi (1980) Cell 22:479-488.
Caplan et al. (2008) Cell 132:449-462.
Césari et al. (2014) EMBO J 33:1941-1959.
Chakraborty et al. (2011) Euphytica 179:19-32.
Cheng et al. (1996) Plant Cell Rep. 15:653-657.
Cheng et al. (2009) Plant Cell 21:2503-2516.
Clapp (1993) Clin. Perinatol. 20:155-168.
Cloutier et al. (2007) Plant Mol Biol 65:93-106.
Coco et al. (2001) Nature Biotechnology 19:354-359.
Coco et al. (2002) Nature Biotechnology 20:1246-1250.
Comai et al. (2004) Plant J 37: 778-786.
Cooley et al. (2000) Plant Cell 12:663-676.
Crameri et al. (1998) Nature 391:288-291.
Curiel et al. (1992) Hum. Gen. Ther. 3:147-154.
Deslandes et al. (2003) Proc Natl Acad Sci USA 100:8024-8029.
Duplessis et al. (2011) Proc Natl Acad Sci USA 108:9166-9171.
Eggert et al. (2005) Chembiochem 6:1062-1067.
Eglitis et al. (1988) Biotechniques 6:608-614.
Ellis et al. (2014) Frontiers in Plant Science 5:641.
Enkhbayar et al. (2004) Proteins 54:394-403.
Feuillet et al. (2003) Proc Natl Acad Sci 100:15253-15258.
Fujimura et al. (1985) Plant Tissue Cultural Letters 2:74.
Gao et al. (2011) Proc Natl Acad Sci USA 108:7619-7624.
Garfinkel et al. (1983) Cell 27: 143-153.
Gietz and Woods (2002) Meth. Enzymol. 350:87-96.
Graham et al. (1973) Virology 54:536-539.
Grant et al. (1995) Plant Cell Rep. 15:254-258.
Greve (1983) J. Mol. Appl. Genet. 1: 499-511.
Harayama (1998) Trends Biotechnol. 16:76-82.
Hellinga (1997) Proc. Natl. Acad. Sci. 94:10015-10017.
Henikoff et al. (2004) Plant Physiol 135: 630-636.
Hinchee et al. (1988) Biotech. 6:915
Huang et al. (2003) Genetics 164:655-664.
Ishida et al. (2014) Wheat (*Triticum aestivum* L.) transformation using immature wheat embryos. In Wang (ed.) *Agrobacterium* protocols: Volume 1, Methods in Molecular Biology, vol. 1223. Springer, New York.
Jézéquel et al. (2008) Biotechniques 45:523-532.
Jin and Singh (2006) Plant Dis 90:476-480.
Jordan et al. (2011) Plant J 65:610-621.
Joshi (1987) Nucl. Acid Res. 15: 6643-6653.
Kerber and Dyck (1979) Resistance to stem and leaf rust of wheat in *Aegilops squarrosa* and transfer of a gene for stem rust resistance to hexaploid wheat. P.358-364. In S. Ramanujam (ed.) Proc. 5th Int. Wheat Genet Symp, New Delhi, India, 23-28 Feb. 1978.
Krattinger et al. (2009) Science 323:37-395.
Langridge et al. (2001) Aust. J. Agric. Res. 52: 1043-1077.
Lemieux (2000) Current Genomics 1: 301-311.
Leung et al. (1989) Technique 1:11-15.
Lu and Berry (2007) Protein Structure Design and Engineering, Handbook of Proteins 2: 1153-1157.
Lu et al. (1993) J. Exp. Med. 178: 2089-2096.
Maas et al. (1997) Mol. Breed 3:15-28.
Maekawa et al. (2011) Cell Host Microbe 9:187-199.
Mago et al. (2004) Genome 47, 112-121.
Mago et al. (2005) Theor Appl Genet 112: 41-50.
Mago et al. (2009) Theor Appl Genet 124:65-70.
McIntosh et al. (1995) Wheat rusts: an atlas of resistance genes (CSIRO Publishing, 1995).
Medberry et al. (1992) Plant Cell 4: 185-192.
Medberry et al. (1993) Plant J. 3: 619-626.
Meyers et al. (1999) Plant Journal 20:317-332.
Michelmore and Meyers (1998) Genome Res. 8:1113-1130.
Needleman and Wunsch (1970) J. Mol Biol. 45:443-453.
Ness et al. (2002) Nature Biotechnology 20:1251-1255.
Niedz et al. (1995) Plant Cell Reports 14: 403-406.
Olson et al. (2013) Theor Appl Genet (DOI 10.1007/s00122-013-2045-5).
Ostermeier et al. (1999) Nature Biotechnology 17:1205-1209.
Ow et al. (1986) Science 234: 856-859.
Pan et al. (2000) J. Mol. Evol. 50:203-2013.
Periyannan et al. (2013) Science 341:786-788.
Prasher et al. (1985) Biochem. Biophys. Res. Comm. 126: 1259-68.
Qi et al. (2012) Plant Physiology 158:1819-1832.
Richardson et al. (2014) Plant Cell, Tissue and Organ Culture 119:647-659.
Rogowsky et al. (1991) Theor Appl Genet 82:537-544.
Salomon et al. (1984) EMBO J. 3: 141-146.
Saintenac et al. (2013) Science 341:783-786.
Seeholzer et al. (2010) Mol Plant Microbe Interact 23:497-509.
Shen et al. (2007) Science 325:1098-103.
Shepherd, K. W. in Proceedings of the 4th International Wheat Genetics Symposium, Columbia, Mo., USA (eds Sears E. R. & Sears L. M. S.). 745-760 (University of Missouri, 1973).
Sieber et al. (2001) Nature Biotechnology 19:456-460.
Simkova et al. (2008) BMC Genomics. 9:237.
Singh et al. (2011) Annu Rev Phytopathol 49:465-481.
Sinnett et al. (1998) BioTechniques 24:752-754.
Slade and Knauf (2005) Transgenic Res. 14: 109-115.
Slootweg et al. (2010) Plant Cell 22:4195-4215.
Stalker et al. (1988) Science 242:419-423.
Stemmer (1994a) Proc. Natl. Acad. Sci. USA 91:10747-10751.
Stemmer (1994b) Nature 370(6488):389-391.
Takemoto et al. (2012) Mol Plant Microbe Interact 25:379-392.
Tameling et al. (2002) Plant Cell 14:2929-2939.
Tameling et al. (2010) Plant Cell 22:4176-4194.
Tasset et al. (2010) PLoS Pathog 6(11): e1001202. doi:10.1371/journal.ppat.1001202.
Thillet et al. (1988) J. Biol. Chem. 263:12500.
Toriyama et al. (1986) Theor. Appl. Genet. 205:34.
Traut (1994) Eur. J. Biochem. 222:9-19.
Volkov et al. (1999) Nucleic Acids Research 27:e18.
Wagner et al. (1992) Proc. Natl. Acad. Sci. USA 89:6099-6103.
Wang et al. (1998) Acta. Hortic. 461:401-405.
Wang et al. (2011) New Phytologist. 191: 418-431.
Wei et al. (1999) Genetics 153:1929-1948.
Wei et al. (2002) Plant Cell 14:1903-1917.
Wen et al. (1995) Cell 82:463-473.
Wirthmueller et al. (2007) Curr Biol 17:2023-2029.
Zeller, F. J. in Proceedings of the 4th International Wheat Genetics Symposium, Columbia, Mo., USA (eds Sears E. R. & Sears L. M. S.). 209-221 (University of Missouri, 1973).
Zeller and Fuchs (1983) Z. PfiZiicht 90:285296.
Zhai et al. (2014) PLoSONE 9:e98067. doi:10.1371/journal.pone.0098067.
Zhao et al. (1998) Nature Biotechnology 16:258-261.

The invention claimed is:

1. A plant genetically modified to comprise a gene encoding a polypeptide which is at least 99% identical to SEQ ID NO:1, wherein the polypeptide confers resistance to one or more races of *Puccinia graminis*, and wherein the plant is a cereal plant.

2. The plant of claim 1, wherein the *Puccinia graminis* is *Puccinia graminis* f. sp. *tritici*.

3. The plant of claim 2, wherein the *Puccinia graminis* f. sp. *tritici* is a race of the Ug99 group.

4. The plant of claim 1 which has enhanced resistance to *Puccinia graminis* when compared to an isogenic plant lacking the gene encoding the polypeptide.

5. The plant of claim 1 which comprises one or more further exogenous polynucleotides encoding another plant pathogen resistance polypeptide.

6. The plant of claim 1 which is homozygous for the gene encoding the polypeptide.

7. A seed of a plant of claim 1 comprising the gene encoding the polypeptide.

8. The plant of claim 1, wherein the polypeptide comprises the amino acid sequence of SEQ ID NO: 1.

9. The plant of claim 1, wherein the polypeptide is encoded by the nucleic acid having the polynucleotide sequence of SEQ ID NO: 10.

10. The plant of claim 1, wherein the polypeptide is encoded by a nucleic acid having a polynucleotide sequence which is at least 99% identical to SEQ ID NO:10.

11. The plant of claim 1, wherein the cereal plant is a wheat plant.

12. The plant of claim 1, wherein the polypeptide comprises a coiled coil (CC) domain, a nucleotide binding (NB) domain and a leucine rich repeat (LRR) domain.

13. The plant of claim 1, wherein the cereal plant is a rye plant.

* * * * *

SEQUENCE LISTING

<160> NUMBER OF SEQ ID NOS: 60

<210> SEQ ID NO 1
<211> LENGTH: 956
<212> TYPE: PRT
<213> ORGANISM: Secale cereale

<400> SEQUENCE: 1

```
Met Asn Ile Val Thr Gly Ala Met Gly Ser Leu Ile Pro Lys Leu Gly
1               5                   10                  15

Glu Leu Leu Met Asp Glu Tyr Lys Leu His Lys Arg Ile Lys Lys Asp
            20                  25                  30

Val Glu Phe Leu Lys Lys Glu Leu Glu Ser Met His Ala Ala Leu Ile
        35                  40                  45

Lys Val Gly Glu Val Pro Arg Asp Gln Leu Asp Arg Gln Val Lys Leu
    50                  55                  60

Trp Ala Asp Glu Val Arg Glu Leu Ser Tyr Asn Met Glu Asp Val Val
65                  70                  75                  80

Asp Lys Phe Leu Val Arg Val Asp Gly Asp Gly Ile Gln Gln Pro His
                85                  90                  95

Asp Asn Ser Gly Arg Phe Lys Glu Leu Lys Asn Lys Met Ile Gly Leu
            100                 105                 110

Phe Lys Lys Gly Arg Asn His His Arg Ile Ala Asp Ala Ile Lys Glu
        115                 120                 125

Ile Lys Glu Gln Leu Gln Glu Val Ala Ala Arg Arg Asp Arg Asn Lys
    130                 135                 140

Val Ala Val Pro Asn Pro Met Glu Pro Ile Thr Ile Asp Pro Cys Leu
145                 150                 155                 160

Arg Ala Leu Tyr Ala Glu Ala Thr Glu Leu Val Gly Ile Tyr Gly Lys
                165                 170                 175

Arg Asp Glu Glu Leu Met Arg Leu Leu Ser Met Glu Gly Asp Asp Ala
            180                 185                 190

Ser Asn Lys Arg Leu Lys Lys Val Ser Ile Val Gly Phe Gly Gly Leu
        195                 200                 205

Gly Lys Thr Thr Leu Ala Arg Ala Val Tyr Asp Lys Ile Lys Gly Asp
    210                 215                 220

Phe Asp Cys Arg Ala Phe Val Pro Val Gly Gln Asn Pro Asp Met Lys
225                 230                 235                 240

Lys Val Leu Arg Asp Ile Leu Ile Asp Leu Gly Asn Pro His Ser Asp
                245                 250                 255

Leu Ala Ile Leu Asp Asp Lys Gln Leu Val Lys Lys Leu His Asp Phe
            260                 265                 270

Leu Glu Asn Lys Arg Tyr Leu Val Ile Ile Asp Asp Ile Trp Asp Glu
        275                 280                 285

Met Leu Trp Glu Gly Ile Asn Phe Ala Phe Ser Asn Arg Asn Asn Leu
    290                 295                 300

Gly Ser Arg Leu Ile Thr Thr Thr Arg Asn Phe Asp Val Ser Lys Ser
305                 310                 315                 320

Cys Cys Leu Ser Ala Asp Asp Ser Ile Tyr Lys Met Lys Pro Leu Ser
                325                 330                 335

Thr Asp Asp Ser Arg Arg Leu Phe His Lys Arg Ile Phe Pro Asp Ala
            340                 345                 350

Gly Gly Cys Pro Ser Glu Phe Gln Gln Val Ser Glu Asp Ile Leu Lys
        355                 360                 365
```

-continued

```
Lys Cys Gly Gly Val Pro Leu Ala Ile Ile Thr Ile Ala Ser Ala Leu
    370                 375                 380
Ala Ser Gly Gln His Val Lys Pro Lys His Glu Trp Asp Ile Leu Leu
385                 390                 395                 400
Gln Ser Leu Gly Ser Gly Val Thr Lys Asp Asn Ser Leu Val Glu Met
                405                 410                 415
Arg Arg Ile Leu Ser Phe Ser Tyr Tyr Asn Leu Pro Ser His Leu Lys
            420                 425                 430
Thr Cys Leu Leu Tyr Leu Cys Ile Tyr Pro Glu Asp Ser Thr Ile Gly
            435                 440                 445
Arg Asp Arg Leu Ile Trp Lys Trp Val Ala Glu Gly Phe Val His His
450                 455                 460
Gly Asp Gln Gly Thr Ser Leu Phe Leu Val Gly Leu Asn Tyr Phe Asn
465                 470                 475                 480
Gln Leu Ile Asn Arg Ser Met Ile Gln Pro Ile Tyr Asp Glu Leu Gly
                485                 490                 495
Gln Val His Ala Cys Arg Val His Asp Met Val Leu Asp Leu Ile Cys
                500                 505                 510
Asn Phe Ser His Glu Ala Lys Phe Val Asn Val Leu Asp Gly Thr Gly
            515                 520                 525
Asn Ser Ile Ser Ser Gln Ser Asn Val Arg Arg Leu Ser Leu Gln Asn
530                 535                 540
Lys Met Glu Asp His Gln Ala Lys Pro Leu Thr Asn Ile Met Ser Met
545                 550                 555                 560
Ser Arg Val Arg Ser Ile Thr Ile Phe Pro Pro Ala Val Ser Ile Met
                565                 570                 575
Pro Ser Leu Ser Met Phe Glu Val Leu Arg Val Leu Asp Leu Ser Asn
                580                 585                 590
Cys Asp Leu Gly Lys Ser Ser Leu Gln Leu Asn Leu Lys Gly Val
            595                 600                 605
Gly His Leu Ile His Leu Arg Tyr Leu Asp Leu Gln Gly Thr Gln Ile
            610                 615                 620
Ser Glu Leu Pro Thr Glu Ile Gly Asn Leu Gln Phe Leu Glu Val Leu
625                 630                 635                 640
Asp Leu Asp Asn Asn Tyr Glu Leu Asp Glu Leu Pro Ser Thr Leu Phe
                645                 650                 655
Lys Leu Arg Arg Leu Ile Tyr Leu Asn Val Met Leu Tyr Lys Val Val
            660                 665                 670
Pro Thr Pro Gly Val Leu Gln Asn Met Thr Ser Ile Glu Val Leu Arg
            675                 680                 685
Gly Val Leu Val Ser Leu Asn Ile Ile Ala Gln Glu Leu Gly Asn Leu
690                 695                 700
Thr Arg Leu Arg Glu Leu Lys Ile Cys Phe Lys Asp Gly Asn Leu Asp
705                 710                 715                 720
Ser Tyr Lys Leu Phe Val Lys Ser Leu Gly Asn Leu His His Ile Glu
                725                 730                 735
Ser Leu Ser Ile Ser Tyr Asn Ser Lys Glu Thr Ser Phe Glu Leu Met
            740                 745                 750
Asp Leu Leu Gly Glu Arg Trp Val Pro Val His Leu Arg Glu Phe
            755                 760                 765
Val Ser Trp Met Pro Ser Gln Leu Ser Ala Leu Arg Gly Trp Ile Lys
770                 775                 780
Arg Asp Pro Ser His Leu Ser Asn Leu Ser Glu Leu Ile Leu Trp Pro
```

```
                785                 790                 795                 800
Val Lys Glu Val Gln Gln Glu Asp Val Glu Ile Ile Gly Gly Leu Leu
                805                 810                 815

Ser Leu Arg Arg Leu Trp Ile Lys Ser Thr His Gln Thr Gln Arg Leu
                820                 825                 830

Leu Val Ile Arg Ala Asp Gly Phe Arg Cys Met Met Asp Phe Glu Leu
                835                 840                 845

Asn Cys Gly Ser Ala Ala Gln Ile Met Phe Glu Pro Gly Ala Leu Pro
                850                 855                 860

Arg Ala Glu Val Leu Val Phe Ser Leu Gly Val Arg Val Ala Gln Glu
865                 870                 875                 880

Asp Gly Asn Cys Gly Phe Asp Leu Gly Leu Gln Gly Asn Leu Leu Ser
                885                 890                 895

Leu Arg His Asp Val Phe Val Arg Ile Tyr Cys Gly Gly Ala Arg Val
                900                 905                 910

Gly Glu Ala Lys Glu Ala Glu Ala Ala Val Arg His Ala Leu Glu Ala
                915                 920                 925

His Pro Asn His Pro Pro Ile Asp Ile Glu Met Thr Pro Tyr Ile Ala
                930                 935                 940

Glu Gly Ala Arg Asp Asp Leu Cys Glu Glu Asn
945                 950                 955

<210> SEQ ID NO 2
<211> LENGTH: 956
<212> TYPE: PRT
<213> ORGANISM: Secale cereale

<400> SEQUENCE: 2

Met Asn Ile Val Thr Gly Ala Met Gly Ser Leu Ile Pro Lys Leu Gly
1               5                   10                  15

Glu Leu Leu Met Asp Glu Tyr Lys Leu His Lys Arg Ile Lys Lys Asp
                20                  25                  30

Val Glu Phe Leu Lys Lys Glu Leu Glu Ser Met His Ala Ala Leu Ile
                35                  40                  45

Lys Val Gly Glu Val Pro Arg Asp Gln Leu Asp Arg Gln Val Lys Leu
            50                  55                  60

Trp Ala Asp Glu Val Arg Glu Leu Ser Tyr Asn Met Glu Asp Val Val
65              70                  75                  80

Asp Lys Phe Leu Val Arg Val Asp Gly Asp Gly Ile Gln Gln Pro His
                85                  90                  95

Asp Asn Ser Gly Arg Phe Lys Glu Leu Lys Asn Lys Met Ile Gly Leu
                100                 105                 110

Phe Lys Lys Gly Arg Asn His His Arg Ile Ala Asp Ala Ile Lys Glu
                115                 120                 125

Ile Lys Glu Gln Leu Gln Glu Val Ala Ala Arg Arg Asp Arg Asn Lys
            130                 135                 140

Val Ala Val Pro Asn Pro Met Glu Pro Ile Thr Ile Asp Pro Cys Leu
145                 150                 155                 160

Arg Ala Leu Tyr Ala Glu Ala Thr Glu Leu Val Gly Ile Tyr Gly Lys
                165                 170                 175

Arg Asp Glu Glu Leu Met Arg Leu Leu Ser Met Glu Gly Asp Asp Ala
                180                 185                 190

Ser Asn Lys Arg Leu Lys Lys Val Ser Ile Val Gly Phe Gly Gly Leu
            195                 200                 205
```

-continued

```
Gly Lys Thr Thr Leu Ala Arg Ala Val Tyr Asp Lys Ile Lys Gly Asp
    210                 215                 220
Phe Asp Cys Arg Ala Phe Val Pro Val Gly Gln Asn Pro Asp Met Lys
225                 230                 235                 240
Lys Val Leu Arg Asp Ile Leu Ile Asp Leu Gly Asn Pro His Ser Asp
                245                 250                 255
Leu Ala Ile Leu Asp Asp Lys Gln Leu Val Lys Lys Leu His Asp Phe
            260                 265                 270
Leu Glu Asn Lys Arg Tyr Leu Val Ile Ile Asp Asp Ile Trp Asp Glu
        275                 280                 285
Met Leu Trp Glu Gly Ile Asn Phe Ala Phe Ser Asn Arg Asn Asn Leu
    290                 295                 300
Gly Ser Arg Leu Ile Thr Thr Thr Arg Asn Phe Asp Val Ser Lys Ser
305                 310                 315                 320
Cys Cys Leu Ser Ala Asp Asp Ser Ile Tyr Lys Met Lys Pro Leu Ser
                325                 330                 335
Thr Asp Asp Ser Arg Arg Leu Phe His Lys Arg Ile Phe Pro Asp Ala
            340                 345                 350
Gly Gly Cys Pro Ser Glu Phe Gln Gln Val Ser Glu Asp Ile Leu Lys
        355                 360                 365
Lys Cys Gly Gly Val Pro Leu Ala Ile Ile Thr Ile Ala Ser Ala Leu
    370                 375                 380
Ala Ser Gly Gln His Val Lys Pro Lys His Glu Trp Asp Ile Leu Leu
385                 390                 395                 400
Gln Ser Leu Gly Ser Gly Val Thr Lys Asp Asn Ser Leu Val Glu Met
                405                 410                 415
Arg Arg Ile Leu Ser Phe Ser Tyr Tyr Asn Leu Pro Ser His Leu Lys
            420                 425                 430
Thr Cys Leu Leu Tyr Leu Cys Ile Tyr Pro Glu Asp Ser Thr Ile Gly
        435                 440                 445
Arg Asp Arg Leu Ile Trp Lys Trp Val Ala Glu Gly Phe Val His His
    450                 455                 460
Gly Asp Gln Gly Thr Ser Leu Phe Leu Val Gly Leu Asn Tyr Phe Asn
465                 470                 475                 480
Gln Leu Ile Asn Arg Ser Met Ile Gln Pro Ile Tyr Asp Glu Leu Gly
                485                 490                 495
Gln Val His Ala Cys Arg Val His Asp Met Val Leu Asp Leu Ile Cys
            500                 505                 510
Asn Phe Ser His Glu Ala Lys Phe Val Asn Val Leu Asp Gly Thr Gly
        515                 520                 525
Asn Ser Ile Ser Ser Gln Ser Asn Val Arg Arg Leu Ser Leu Gln Asn
    530                 535                 540
Lys Met Glu Asp His Gln Ala Lys Pro Leu Thr Asn Ile Met Ser Met
545                 550                 555                 560
Ser Arg Val Arg Ser Ile Thr Ile Phe Pro Pro Ala Val Ser Ile Met
                565                 570                 575
Pro Ser Leu Ser Met Phe Glu Val Leu Arg Val Leu Asp Leu Ser Asn
            580                 585                 590
Cys Asp Leu Gly Lys Ser Ser Leu Gln Leu Asn Leu Lys Gly Val
        595                 600                 605
Gly His Leu Ile His Leu Arg Tyr Leu Asp Leu Gln Gly Thr Gln Ile
    610                 615                 620
Ser Glu Leu Pro Thr Glu Ile Gly Asn Leu Gln Phe Leu Glu Val Leu
```

```
                625                 630                 635                 640
Asp Leu Asp Asn Asn Tyr Glu Leu Asp Glu Leu Pro Ser Thr Leu Phe
                        645                 650                 655

Lys Leu Arg Arg Leu Ile Tyr Leu Asn Val Met Leu Tyr Lys Val Val
                660                 665                 670

Pro Thr Pro Gly Val Leu Gln Asn Met Thr Ser Ile Glu Val Leu Arg
            675                 680                 685

Gly Val Leu Val Ser Leu Asn Ile Ile Ala Gln Glu Leu Gly Asn Leu
        690                 695                 700

Thr Arg Leu Arg Glu Leu Lys Ile Cys Phe Lys Asp Gly Asn Leu Asp
705                 710                 715                 720

Ser Tyr Lys Leu Phe Val Lys Ser Leu Gly Asn Leu His His Ile Glu
                725                 730                 735

Ser Leu Ser Ile Ser Tyr Asn Ser Lys Glu Thr Ser Phe Glu Leu Met
                740                 745                 750

Asp Leu Leu Gly Glu Arg Trp Val Pro Val His Leu Arg Glu Phe
            755                 760                 765

Val Ser Trp Met Pro Ser Gln Leu Ser Ala Leu Arg Gly Trp Ile Lys
    770                 775                 780

Arg Asp Pro Ser His Leu Ser Asn Leu Ser Glu Leu Ile Leu Trp Pro
785                 790                 795                 800

Val Lys Glu Val Gln Gln Glu Asp Val Glu Ile Ile Gly Gly Leu Leu
                805                 810                 815

Ser Leu Arg Arg Leu Gly Ile Lys Ser Thr His Gln Thr Gln Arg Leu
                820                 825                 830

Leu Val Ile Arg Ala Asp Gly Phe Arg Cys Met Met Asp Phe Glu Leu
            835                 840                 845

Asn Cys Gly Ser Ala Ala Gln Ile Met Phe Glu Pro Gly Ala Leu Pro
        850                 855                 860

Arg Ala Glu Val Leu Val Phe Ser Leu Gly Val Arg Val Ala Gln Glu
865                 870                 875                 880

Asp Gly Asn Cys Gly Phe Asp Leu Gly Leu Gln Gly Asn Leu Leu Ser
                885                 890                 895

Leu Arg His Asp Val Phe Val Arg Ile Tyr Cys Gly Gly Ala Arg Val
                900                 905                 910

Gly Glu Ala Lys Glu Ala Glu Ala Ala Val Arg His Ala Leu Glu Ala
            915                 920                 925

His Pro Asn His Pro Pro Ile Asp Ile Glu Met Thr Pro Tyr Ile Ala
        930                 935                 940

Glu Gly Ala Arg Asp Asp Asp Leu Cys Glu Glu Asn
945                 950                 955

<210> SEQ ID NO 3
<211> LENGTH: 959
<212> TYPE: PRT
<213> ORGANISM: Secale cereale

<400> SEQUENCE: 3

Met Asn Ile Val Thr Gly Ala Met Gly Ser Leu Ile Pro Lys Leu Gly
1               5                   10                  15

Glu Leu Leu Met Asp Glu Tyr Lys Leu His Lys Arg Ile Lys Lys Asp
                20                  25                  30

Val Glu Phe Leu Lys Lys Glu Leu Glu Ser Met His Ala Ala Leu Ile
            35                  40                  45
```

```
Lys Val Gly Glu Val Pro Arg Asp Gln Leu Asp Arg Gln Val Lys Leu
 50                  55                  60

Trp Ala Asp Glu Val Arg Glu Leu Ser Tyr Asn Met Glu Asp Val Val
 65                  70                  75                  80

Asp Lys Phe Leu Val Arg Val Asp Gly Asp Gly Ile Gln Gln Pro His
                 85                  90                  95

Asp Asn Ser Gly Arg Phe Lys Glu Leu Lys Asn Lys Met Ile Gly Leu
            100                 105                 110

Phe Lys Lys Gly Arg Asn His His Arg Ile Ala Asp Ala Ile Lys Glu
        115                 120                 125

Ile Lys Glu Gln Leu Gln Glu Val Ala Ala Arg Arg Asp Arg Asn Lys
130                 135                 140

Val Ala Val Pro Asn Pro Met Glu Pro Ile Thr Ile Asp Pro Cys Leu
145                 150                 155                 160

Arg Ala Leu Tyr Ala Glu Ala Thr Glu Leu Val Gly Ile Tyr Gly Lys
                165                 170                 175

Arg Asp Glu Glu Leu Met Arg Leu Leu Ser Met Glu Gly Asp Asp Ala
            180                 185                 190

Ser Asn Lys Arg Leu Lys Lys Val Ser Ile Val Gly Phe Gly Gly Leu
        195                 200                 205

Gly Lys Thr Thr Leu Ala Arg Ala Val Tyr Asp Lys Ile Lys Gly Asp
210                 215                 220

Phe Asp Cys Arg Ala Phe Val Pro Val Gly Gln Asn Pro Asp Met Lys
225                 230                 235                 240

Lys Val Leu Arg Asp Ile Leu Ile Asp Leu Gly Asn Pro His Ser Asp
                245                 250                 255

Leu Ala Ile Leu Asp Asp Lys Gln Leu Val Lys Lys Leu His Asp Phe
            260                 265                 270

Leu Glu Asn Lys Arg Tyr Leu Val Ile Ile Asp Asp Ile Trp Asp Glu
        275                 280                 285

Met Leu Trp Glu Gly Ile Asn Phe Ala Phe Ser Asn Arg Asn Asn Leu
290                 295                 300

Gly Ser Arg Leu Ile Thr Thr Thr Arg Asn Phe Asp Val Ser Lys Ser
305                 310                 315                 320

Cys Cys Leu Ser Ala Asp Asp Ser Ile Tyr Lys Met Lys Pro Leu Ser
                325                 330                 335

Thr Asp Asp Ser Arg Arg Leu Phe His Lys Arg Ile Phe Pro Asp Ala
            340                 345                 350

Gly Gly Cys Pro Ser Glu Phe Gln Gln Val Ser Glu Asp Ile Leu Lys
        355                 360                 365

Lys Cys Gly Gly Val Pro Leu Ala Ile Ile Thr Ile Ala Ser Ala Leu
370                 375                 380

Ala Ser Gly Gln His Val Lys Pro Lys His Glu Trp Asp Ile Leu Leu
385                 390                 395                 400

Gln Ser Leu Gly Ser Gly Val Thr Lys Asp Asn Ser Leu Val Glu Met
                405                 410                 415

Arg Arg Ile Leu Ser Phe Ser Tyr Tyr Asn Leu Pro Ser His Leu Lys
            420                 425                 430

Thr Cys Leu Leu Tyr Leu Cys Ile Tyr Pro Glu Asp Ser Thr Ile Gly
        435                 440                 445

Arg Asp Arg Leu Ile Trp Lys Trp Val Ala Glu Gly Phe Val His His
450                 455                 460

Gly Asp Gln Gly Thr Ser Leu Phe Leu Val Gly Leu Asn Tyr Phe Asn
```

```
                465                 470                 475                 480
        Gln Leu Ile Asn Arg Ser Met Ile Gln Pro Ile Tyr Asp Glu Leu Gly
                            485                 490                 495

Gln Val His Ala Cys Arg Val His Asp Met Val Leu Asp Leu Ile Cys
                            500                 505                 510

Asn Phe Ser His Glu Ala Lys Phe Val Asn Val Leu Asp Gly Thr Gly
                            515                 520                 525

Asn Ser Ile Ser Ser Gln Ser Asn Val Arg Arg Leu Ser Leu Gln Asn
                    530                 535                 540

Lys Met Glu Asp His Gln Ala Lys Pro Leu Thr Asn Ile Met Ser Met
        545                 550                 555                 560

Ser Arg Val Arg Ser Ile Thr Ile Phe Pro Ala Val Ser Ile Met
                            565                 570                 575

Pro Ser Leu Ser Met Phe Glu Val Leu Arg Val Leu Asp Leu Ser Asn
                    580                 585                 590

Cys Asp Leu Gly Lys Ser Ser Leu Gln Leu Asn Leu Lys Gly Val
                595                 600                 605

Gly His Leu Ile His Leu Arg Tyr Leu Asp Leu Gln Gly Thr Gln Ile
                610                 615                 620

Ser Glu Leu Pro Thr Glu Ile Gly Asn Leu Gln Phe Leu Glu Val Leu
        625                 630                 635                 640

Asp Leu Asp Asn Asn Tyr Glu Leu Asp Glu Leu Pro Ser Thr Leu Phe
                            645                 650                 655

Lys Leu Arg Arg Leu Ile Tyr Leu Asn Val Met Leu Tyr Lys Val Val
                            660                 665                 670

Pro Thr Pro Gly Val Leu Gln Asn Met Thr Ser Ile Glu Val Leu Arg
                    675                 680                 685

Gly Val Leu Val Ser Leu Asn Ile Ile Ala Gln Glu Leu Gly Asn Leu
                    690                 695                 700

Thr Arg Leu Arg Glu Leu Lys Ile Cys Phe Lys Asp Gly Asn Leu Asp
        705                 710                 715                 720

Ser Tyr Lys Leu Phe Val Lys Ser Leu Gly Asn Leu His His Ile Glu
                            725                 730                 735

Ser Leu Ser Ile Ser Tyr Asn Ser Lys Glu Thr Ser Phe Glu Leu Met
                            740                 745                 750

Asp Leu Leu Gly Glu Arg Trp Val Pro Pro Val His Leu Arg Glu Phe
                            755                 760                 765

Val Ser Trp Met Pro Ser Gln Leu Ser Ala Leu Arg Gly Trp Ile Lys
                    770                 775                 780

Arg Asp Pro Ser His Leu Ser Asn Leu Ser Glu Leu Ile Leu Trp Pro
        785                 790                 795                 800

Val Lys Glu Val Gln Gln Glu Asp Val Glu Ile Ile Gly Gly Leu Leu
                            805                 810                 815

Ser Leu Arg Arg Leu Trp Ile Lys Ser Thr His Gln Thr Gln Arg Leu
                    820                 825                 830

Leu Val Ile Arg Ala Asp Gly Phe Arg Cys Met Met Asp Phe Glu Leu
                    835                 840                 845

Asn Cys Gly Ser Ala Ala Gln Ile Met Phe Glu Pro Gly Ala Leu Pro
        850                 855                 860

Arg Ala Glu Val Leu Val Phe Ser Leu Gly Val Arg Val Ala Gln Glu
        865                 870                 875                 880

Asp Gly Asn Cys Gly Phe Asp Leu Gly Leu Gln Gly Asn Leu Leu Ser
                    885                 890                 895
```

```
Leu Arg His Asp Val Phe Val Arg Ile Tyr Cys Gly Ala Arg Val
            900                 905                 910

Gly Glu Ala Lys Glu Ala Glu Ala Ala Val Arg His Ala Leu Glu Ala
        915                 920                 925

His Pro Asn His Pro Pro Ile Asp Ile Glu Met Thr Pro Tyr Ile Ala
    930                 935                 940

Glu Gly Ala Arg Asp Asp Leu Cys Glu Arg Thr Asp Leu
945                 950                 955

<210> SEQ ID NO 4
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: x
<222> LOCATION: (2)..(3)
<223> OTHER INFORMATION: any amino acid
<220> FEATURE:
<221> NAME/KEY: x
<222> LOCATION: (5)..(5)
<223> OTHER INFORMATION: any amino acid
<220> FEATURE:
<221> NAME/KEY: x
<222> LOCATION: (8)..(8)
<223> OTHER INFORMATION: T or S

<400> SEQUENCE: 4

Gly Xaa Xaa Gly Xaa Gly Lys Xaa Thr
1               5

<210> SEQ ID NO 5
<211> LENGTH: 9
<212> TYPE: PRT
<213> ORGANISM: Artificial Sequence
<220> FEATURE:
<223> OTHER INFORMATION: p-loop motif of NB domain

<400> SEQUENCE: 5

Gly Phe Gly Gly Leu Gly Lys Thr Thr
1               5

<210> SEQ ID NO 6
<211> LENGTH: 9
<212> TYPE: PRT
<213> ORGANISM: Artificial Sequence
<220> FEATURE:
<223> OTHER INFORMATION: kinase 3a motif of NB domain
<220> FEATURE:
<221> NAME/KEY: X
<222> LOCATION: (2)..(5)
<223> OTHER INFORMATION: any amino acid
<220> FEATURE:
<221> NAME/KEY: X
<222> LOCATION: (6)..(6)
<223> OTHER INFORMATION: any amino acid or absent
<220> FEATURE:
<221> NAME/KEY: X
<222> LOCATION: (8)..(8)
<223> OTHER INFORMATION: any amino acid

<400> SEQUENCE: 6

Gly Xaa Xaa Xaa Xaa Xaa Thr Xaa Arg
1               5

<210> SEQ ID NO 7
<211> LENGTH: 9
```

```
<212> TYPE: PRT
<213> ORGANISM: Artificial Sequence
<220> FEATURE:
<223> OTHER INFORMATION: kinase 3a motif of NB domain

<400> SEQUENCE: 7

Gly Ser Arg Leu Ile Thr Thr Thr Arg
1               5

<210> SEQ ID NO 8
<211> LENGTH: 9
<212> TYPE: PRT
<213> ORGANISM: Artificial Sequence
<220> FEATURE:
<223> OTHER INFORMATION: LRR repeat motif
<220> FEATURE:
<221> NAME/KEY: X
<222> LOCATION: (1)..(2)
<223> OTHER INFORMATION: any amino acid
<220> FEATURE:
<221> NAME/KEY: X
<222> LOCATION: (4)..(4)
<223> OTHER INFORMATION: any amino acid
<220> FEATURE:
<221> NAME/KEY: X
<222> LOCATION: (6)..(9)
<223> OTHER INFORMATION: any amino acid

<400> SEQUENCE: 8

Xaa Xaa Leu Xaa Leu Xaa Xaa Xaa Xaa
1               5

<210> SEQ ID NO 9
<211> LENGTH: 3803
<212> TYPE: DNA
<213> ORGANISM: Secale cereale

<400> SEQUENCE: 9
agaggcatcg tgggtgctct cttatctctt gacctgctgt tgttggtctg catctcagtc      60
ctctcctcca ttgcgctgcc tggaataagg tcgatccggc ttcttgattg gtgagctcgt     120
ccaacctcca gctcacccct gccaactgac tgccagagac ctttgacacc tgtggaggga     180
gggagtggaa cagctagcaa gaagcatgga gcttccggtc attattcaga gcaccacaca     240
tggaatccac tgacctggct agcggcctcg taacttcgtc tcatctttct gctactgaa      300
atatatttca gatccacacc ttcccgtcca gatcgagaga gagagaccgc ccttccaac      360
tgacgcctgt gaagctagga tctaaaaaat gacttctcct gctctactga aatctttcac     420
acccgcacgt tcttgttaat ctgctgattt cctatattat aatttcttat ttcgtccgga     480
ttcagtgaag ttgccgctgt gttgtcccat ccatattcag tgcagcgacc ctcacgcatc     540
tggcctctgg tatgccaccg ccgtactctg ctctgccgtg aagaattaag gtgggcttgg     600
tccagatctc gcagttctat tctggtttcc aattgatcga tccagagagc tcatcctcct     660
gctctcatga atattgtcac gggggccatg ggcagcctga tccccaagtt gggcgagctg     720
ctcatggatg agtacaagct gcacaagcgc atcaagaaag atgttgagtt cctcaagaag     780
gagcttgaga gcatgcacgc tgccctcatc aaggttggcg aggtgccgcg ggaccagctc     840
gacaggcaag tcaagctctg gccgacgag gtcagagagc tctcctacaa catgaggat      900
gtcgtcgaca agttcctcgt acgcgtcgac ggcgacggca ttcagcagcc tcacgcaaac     960
tccggcagat ttaaggagct caagaacaag atgatcggct tgtttaagaa aggcaggaat    1020
caccatcgca tagctgacgc gatcaaggaa atcaaggagc aactccagga ggtggctgct    1080
```

```
aggcgtgaca ggaacaaggt agctgttcct aatcctatgg aaccaattac tatcgatcct    1140
tgtcttcgag ctttgtacgc agaagcgaca gagctagttg gcatatatgg aagagggat    1200 gaggagctca tgaggttgct ctccatggag ggtgatgatg cctctaacaa gagactaaag    1260
aaggtctcca ttgttggatt tggagggttg ggcaagacca ctcttgctag agcagtatac    1320
gacaagatta aaggtgattt tgattgtcgg gcatttgttc ccgtcggtca gaaccctgac    1380
atgaagaagg ttttaaggga tatcctcatt gatctcggca accctcactc agatcttgct    1440
atactggatg acaaacaact tgttaaaaag cttcatgatt tcctagagaa caaaaggtat    1500
cttgtcataa ttgatgatat atgggacgaa atgttgtggg aaggcatcaa ctttgctttc    1560
tccaatagga ataatctagg cagtcggcta atcaccacaa cccgcaattt cgatgtctcc    1620
aaatcatgtt gcttatcggc tgatgattca atatataaaa tgaaacctct ttctactgat    1680
gactccagaa ggctcttcca taagagaata tttcctgacg ctggtggatg tccaagtgaa    1740
tttcaacaag tgtctgaaga catattgaag aaatgtggtg gagtaccact ggccatcatt    1800
actattgcta gtgctttggc tagtggccag catgtgaaac caaagcatga gtgggatatt    1860
ctactccagt cccttggctc cggagtaaca aaagataata gtttggttga gatgcggaga    1920
atactatctt tcagctatta taatctaccg tctcatctga aaacttgtct actttaccta    1980
tgtatatatc cagaagatag caccattggt agagatagac tgatatggaa gtgggtggcc    2040
gaaggatttg tccaccatgg agatcaaggg accagtctgt ttttggtcgg attaaactac    2100
ttcaaccagc tcattaatag aagtatgatc cagccaatat atgatgaact aggccaggta    2160
catgcttgcc gtgtacatga tatggttctt gatcttatct gcaacttctc acatgaagca    2220
aagtttgtta atgtattgga tggcacaggg aatagcatat cttcacaaag taatgtccgt    2280
cgtttgtccc ttcagaataa aatggaagat catcaagcca agcctctcac aaatatcatg    2340
agtatgtcac gagtgaggtc aattactatc tttccacctg ctgttagtat catgccaagt    2400
ctgtcaatgt tgaagttct gcgtgtactt gatctgtcga actgtgattt gggaaaaagt    2460
agcagcctgc agcttaacct caagggtgtt ggacatttaa tccacctaag gtaccttgat    2520
ctacaaggca ctcaaattag tgaactcccg actgagatag gaaacctgca attttttggag    2580 gtgttggatc ttgacaacaa ttatgagcta gatgaattgc cttccactct tttttaaattg    2640 agaagattaa tctacttaaa tgttatgttg tataaggtgg ttccaactcc tggtgtgttg    2700
cagaatatga catccattga agtgttgagg ggggtcttgg tctctctgaa cattattgca    2760
caagagcttg gcaacctgac aaggctgagg gagcttaaga tttgcttcaa ggatggtaat    2820
ttggattcat ataaactttt cgtgaagtct ctgggcaacc tgcatcatat cgaaagccta    2880
agtattagtt acaattccaa agaaacatct tttgaactga tggatctctt gggagagcgt    2940
tgggtgcctc ctgtacatct ccgcgaattt gtgtcttgga tgcccagcca actctctgca    3000
ttgcgaggat ggataaagag agaccctctcg catctctcga acctctccga gttaatcctc    3060
tggccagtga aggaagtgca gcaggaggac gtggaaatca ttgggggtt gctgtcccttt    3120 cgccgtctct ggataaagag cacccaccaa acacagcggc tgctagtcat tcgtgcagat    3180
gggttccgct gcatgatgga ctttgagttg aattgtggat cagcagcgca aatcatgttt    3240
gaaccaggag ctttgccgag gcggaagta cttgtgttca gcctgggcgt gcgggtggcg    3300
caagaggatg gaaactgtgg tttcgacttg ggcctgcagg ggaacctgct ctcccttcgg    3360
catgatgtct ttgttcgtat atattgtggt ggggcgaggg ttggggaggc aaaggaagcg    3420
gaggctgcgg tgaggcacgc gctcgaagcc catcccaacc atcccccgat tgatattgag    3480
```

```
atgaccccgt atatagcaga aggtgctcgt gatgatgatt tgtgtgagga gaactgattt    3540
atgatgtaga ggactcacag tgaatcaggt agcaggggcg tgggattact gctggtggca    3600
tcggagaatt tgtgtggttt cactaacatt ttgggtgggc gccggccctg caagaattg     3660 aaggatggaa aggtttcgac cttggctgga agttgtgtga tgagcctgca gaaaagata     3720 ttgcttggtt ttgtaatgaa ttagtaacgg tgttggggtg aattgatcct taccgaaaaa    3780
atgttttccg cggctttgtt tta                                            3803

<210> SEQ ID NO 10
<211> LENGTH: 2871
<212> TYPE: DNA
<213> ORGANISM: Secale cereale

<400> SEQUENCE: 10
atgaatattg tcacgggggc catgggcagc ctgatcccca gttgggcga gctgctcatg      60 gatgagtaca agctgcacaa gcgcatcaag aaagatgttg agttcctcaa gaaggagctt    120
gagagcatgc acgctgccct catcaaggtt ggcgaggtgc cgcgggacca gctcgacagg    180
caagtcaagc tctgggccga cgaggtcaga gagctctcct acaacatgga ggatgtcgtc    240
gacaagttcc tcgtacgcgt cgacggcgac ggcattcagc agcctcacga caactccggc    300
agatttaagg agctcaagaa caagatgatc ggcttgttta agaaaggcag gaatcaccat    360
cgcatagctg acgcgatcaa ggaaatcaag gagcaactcc aggaggtggc tgctaggcgt    420
gacaggaaca aggtagctgt tcctaatcct atggaaccaa ttactatcga tccttgtctt    480
cgagctttgt acgcagaagc gacagagcta gttggcatat atgggaagag ggatgaggag    540
ctcatgaggt tgctctccat ggagggtgat gatgcctcta acaagagact aaagaaggtc    600
tccattgttg gatttggagg gttgggcaag accactcttg ctagagcagt atacgacaag    660
attaaaggtg attttgattg tcgggcattt gttcccgtcg gtcagaaccc tgacatgaag    720
aaggttttaa gggatatcct cattgatctc ggcaacccct actcagatct tgctatactg    780
gatgacaaac aacttgttaa aaagcttcat gatttcctag agaacaaaag gtatcttgtc    840
ataattgatg atatatggga cgaaatgttg tgggaaggca tcaactttgc tttctccaat    900
aggaataatc taggcagtcg gctaatcacc acaacccgca atttcgatgt ctccaaatca    960
tgttgcttat cggctgatga ttcaatatat aaaatgaaac ctctttctac tgatgactcc   1020
agaaggctct tccataagag aatatttcct gacgctggtg gatgtccaag tgaatttcaa   1080
caagtgtctg aagacatatt gaagaaatgt ggtggagtac cactggccat cattactatt   1140
gctagtgctt tggctagtgg ccagcatgtg aaaccaaagc atgagtggga tattctactc   1200
cagtcccttg gctccggagt aacaaaagat aatagtttgg ttgagatgcg gagaatacta   1260
tctttcagct attataatct accgtctcat ctgaaaactt gtctacttta cctatgtata   1320
tatccagaag atagcaccat tggtagagat agactgatat ggaagtgggt ggccgaagga   1380
tttgtccacc atggagatca agggaccagt ctgttttttgg tcggattaaa ctacttcaac   1440
cagctcatta atagaagtat gatccagcca atatatgatg aactaggcca ggtacatgct   1500
tgccgtgtac atgatatggt tcttgatctt atctgcaact tctcacatga agcaaagttt   1560
gttaatgtat tggatggcac agggaatagc atatcttcac aaagtaatgt ccgtcgtttg   1620
tcccttcaga ataaaatgga agatcatcaa gccaagcctc tcacaaatat catgagtatg   1680
tcacgagtga ggtcaattac tatctttcca cctgctgtta gtatcatgcc aagtctgtca   1740
```

| | | | | |
|---|---|---|---|---|
| atgtttgaag | ttctgcgtgt | acttgatctg | tcgaactgtg | atttgggaaa | aagtagcagc | 1800 |
| ctgcagctta | acctcaaggg | tgttggacat | ttaatccacc | taaggtacct | tgatctacaa | 1860 |
| ggcactcaaa | ttagtgaact | cccgactgag | ataggaaacc | tgcaattttt | ggaggtgttg | 1920 |
| gatcttgaca | acaattatga | gctagatgaa | ttgccttcca | ctcttttaa | attgagaaga | 1980 |
| ttaatctact | taaatgttat | gttgtataag | gtggttccaa | ctcctggtgt | gttgcagaat | 2040 |
| atgcatcca | ttgaagtgtt | gagggggtc | ttggtctctc | tgaacattat | tgcacaagag | 2100 |
| cttggcaacc | tgacaaggct | gagggagctt | aagatttgct | tcaaggatgg | taatttggat | 2160 |
| tcatataaac | ttttcgtgaa | gtctctgggc | aacctgcatc | atatcgaaag | cctaagtatt | 2220 |
| agttacaatt | ccaaagaaac | atcttttgaa | ctgatggatc | tcttgggaga | gcgttgggtg | 2280 |
| cctcctgtac | atctccgcga | atttgtgtct | tggatgccca | gccaactctc | tgcattgcga | 2340 |
| ggatggataa | agagagaccc | ctcgcatctc | tcgaacctct | ccgagttaat | cctctggcca | 2400 |
| gtgaaggaag | tgcagcagga | ggacgtgaaa | atcattgggg | ggttgctgtc | ccttcgccgt | 2460 |
| ctctggataa | agagcaccca | ccaaacacag | cggctgctag | tcattcgtgc | agatgggttc | 2520 |
| cgctgcatga | tggactttga | gttgaattgt | ggatcagcag | cgcaaatcat | gtttgaacca | 2580 |
| ggagctttgc | cgagggcgga | agtacttgtg | ttcagcctgg | gcgtgcgggt | ggcgcaagag | 2640 |
| gatgaaaact | gtggtttcga | cttgggcctg | caggggaacc | tgctctccct | tcggcatgat | 2700 |
| gtctttgttc | gtatatattg | tggtggggcg | agggttgggg | aggcaaagga | agcggaggct | 2760 |
| gcggtgaggc | acgcgctcga | agcccatccc | aaccatcccc | cgattgatat | tgagatgacc | 2820 |
| ccgtatatag | cagaaggtgc | tcgtgatgat | gatttgtgtg | aggagaactg | a | 2871 |

<210> SEQ ID NO 11
<211> LENGTH: 9795
<212> TYPE: DNA
<213> ORGANISM: Artificial Sequence
<220> FEATURE:
<223> OTHER INFORMATION: pVecNeoSr50 expression construct

<400> SEQUENCE: 11

| | | | | |
|---|---|---|---|---|
| gcggccgccc | atccagcgtc | gtcttcctcc | actgctgcag | tcaccgttct | cccgcagtct | 60 |
| acgtcgatcc | gtcaagggct | cggtgccgtg | ctctcctctg | cttccccgag | tccacgtcgg | 120 |
| aggtcccttg | ctcgtgagtt | ctctgctccg | ccgctgtgct | gcatgcatga | tgcgccccga | 180 |
| gaggatggaa | gcacatcatg | catgcatggc | ctttaatata | acccaggcga | tccggccagg | 240 |
| ttcaggagca | cggcgcccta | tctccaagac | ctcgtattgt | actacttacg | agccaaggaa | 300 |
| ttaccgtaca | tgttttttt | ttcacccgc | aaaaaaaaa | ctcgcttttt | ttcttcccaa | 360 |
| attccggcac | cggcatgccg | ttcgtcgcca | caccggcgct | agcttcgggg | tgcatgcagc | 420 |
| ctcgccacgc | caccgccgcc | cgcttttgag | ggagtacttg | tcaattctca | tcactgaaac | 480 |
| ttggtaagaa | aaaagctct | ggattccgct | tttgagcata | cttcaacact | gaacttcaaa | 540 |
| acttaaaaaa | aagggaaaga | aaaaaccat | tagtgccaaa | ctacctctca | ccactcacct | 600 |
| atgctaagaa | aaatgaaaat | gaagaagaa | agaaaaaaag | cagcaccgat | cgctgataaa | 660 |
| aagatatgca | gagctctgaa | gtatgctact | gaacatagat | taacactgaa | gtatagacag | 720 |
| cgcgtaatgt | aatccccaca | actacagcga | gacagacatc | acatgggaaa | aagatcaccg | 780 |
| gcgagcaggc | gacgggcggt | gattccgggc | gagcatgcta | tatatccatc | ccctccttcc | 840 |
| ttcctcccgc | tgctccggtc | cgcctccgcc | tccctcgtcg | gcgacgcccg | gaccctcgct | 900 |
| gttccggagg | cagcatcgat | catctgctat | tcgcgggcat | caatcaagtg | aatcccaagc | 960 |

```
acgccctgac cctcactctc gtcatccgtc tccttccatt aatcctatat ataattatat   1020
acagtatctc tctcagtggt gatgtctcag tcaccacacc caaggtgttt gacaaaatga   1080
ccaactaaga taagggtggc tttcacagca cgtactagta gtatttgtgt tttcctttct   1140
ctctgctaat gtaactaatg tgggtctaac atttctaatg tcgtgggtgg cagtgtgagc   1200
ggctgcagct gcacaagacg tcgtggtctg ctgatttgcc gcggatgctg ccatagtagc   1260
gctggaggac gccgccttag cctgctacaa gaaatcgagg ctgcttcctg gacgcccttg   1320
agttactcga cgaaatgcac aggagagaga gagagactgc ggtccaccac aacaacgaca   1380
ctattggcag gtgcgtaaca acttgcttgc cttcactctc ttcctatttt tctgcatgta   1440
gattaatgta ctagtttatg aatgcatagt ttgtagcatg tccggctcct ccccaccacc   1500
cgtagaacgc aaccgctgct ctgtcccgcc tcgaccgtct gccccttcct atagcattag   1560
cgctgctcac atccacctca aggcactgcc tccatccgcc cagtttgaga ttgggacgtg   1620
tatctttggg tctcgggtga tgatgcatcc gaatcgagag aaataattta gaaactgaaa   1680
aaataagtca aaattgtgat ttgtttagaa caaacatgat attatgttac actcatgtga   1740
aaagattcac gaatgaatga ctttcatgta ctcttgccga aagaaaccaa aatcgacact   1800
atataaaagt tactattcat gcttttatac tcactaatat ctttttttgcc cagaagtcat   1860 tctttcgcga agagtatcac actagatcta gtatgttccc aaaatgttcc agaattttgt   1920
gacctttttt gcaatttcta aattatttct tcaattcagg tgcattggga cccgagaccc   1980
attgggtatt ttcggtatcg attgcttttg agtactgcat aagagtattt accacctggc   2040
aaatgtctga tttttaggagg gagggtaaa tgcatgatgt ggactgacca accaaccgag   2100
agagattcag agaaatgaga ggatcagagt aattgtagtg aagtagagga tcagagtagt   2160
atgcaattat tttctttgaa tccctgtgtc tctatgaccc actgaataga cagatcagcc   2220
aaaagcagta ctgttccgag ggatcgtggg ggcttctttc caccgcaccc accgaaagca   2280
ctactccatt tcttctttac gcaccttctc ccacatccaa cgcatcgacc actgatgaac   2340
aaacacatga gccaaaagca ttactgttcc gagggattcg tatcttgact tgctgttgtg   2400
ggtcttcctc tgctcctcgc ctccactgag tgctccctta atctcgtctc agtcctctcc   2460
ttcatttcta agttgtgagc tgaaactatg tgtttattgt tacagtttag cgtatgttca   2520
tgatcactca gttttgtagg tatggtttca ggttctgtta cagtttaacg tgtgctatgg   2580
aagtctctca ttgagaagct aggtctcgcg cacatggata catccgagtg gcccatgtac   2640
gattccgtct accagtggtg ggacaagaga accgacaacc gcaatcctaa ccggcaagct   2700
atggcttccc tcaccatgct cgtctcgtgg accatttgga atgaaagaaa cgcacgggtg   2760
ttccgccaca agagtgcgcc acccaccatc ctactcaccg ccatcgtcga ggaggccaag   2820
ctttggatgg tcgcgggcgc aaagcaatta gggaatattt ttctaggcga gtagttgtca   2880
tgacgtatgt gcgggtgtgt tgtaactctc taaactctat tctttcctta tttaatagat   2940
gaggcaaagc ttatgcctcc gtttcgaaaa aaaaaacagt ttaacgtgtg ctcatcaact   3000
gaaactatgc ttcaggcatt gagtattcac taccaaatcg aaattttcaa actgaacgga   3060
gggattcaat tctttacccg ttgcaaagat gaaagctagt gaaaaaaatt aatagtgtca   3120
ttgcctgata aatgcatgaa ggatggagag acggtgggg ctctgtatca ttgcctggca   3180
ggtgcatgag gtagattcag agaaatgaga ggacgtacaa ttattgtctc tgagtcactg   3240
tccatgaatg acccactgca ctgaatgatt gcatgagcca aaagcactac tattcagagg   3300
```

```
catcgtgggt gctctcttat ctcttgacct gctgttgttg gtctgcatct cagtcctctc   3360
ctccattgcg ctgcctggaa taaggtcgat ccggcttctt gattggtgag ctcgtccaac   3420
ctccagctca cccctgccaa ctgactgcca gagacctttg acacctgtgg aggtatatat   3480
cctttcgatt tctttccagc tgaagtacgc ttggatctaa aaacttagtt gtccagagct   3540
tgggagactg atttgtgttg gttgaatcca gggagggagt ggaacagcta gcaagaagca   3600
tggagcttcc ggtcattatt cagagcacca cacatggaat ccactgacct ggctagcggc   3660
ctcgtaactt cgtctcatct ttcttgctac tgaaatatat ttcagatcca caccttcccg   3720
tccagatcga gagagagaga ccgccccttc caactgacgc ctgtgaagct aggatctaaa   3780
aaatgacttc tcctgctcta ctgaaatctt tcacacccgc acgttcttgt taatctgctg   3840
atttcctata ttataatttc ttatttcgtc cggattcagt gaagttgccg ctgtgttgtc   3900
ccatccatat tcagtgcagc gaccctcacg catctggcct ctggtatgcc accgccgtac   3960
tctgctctgc cgtgaagaat taaggtgggc ttggtccaga tctcgcagtt ctattctggt   4020
cagttctata gctcgatgaa attaaagctt cacacaattt cgattggatc acggctcccc   4080
ttatgctaag ctttaattttg gcagctctgt tctagagctc gttcacacaa tttggattgc   4140
attacagctc ccctcattca tcaatttaca ggtttccaat tgatcgatcc agagagctca   4200
tcctcctgct ctcatgaata ttgtcacggg ggccatgggc agcctgatcc ccaagttggg   4260
cgagctgctc atggatgagt acaagctgca caagcgcatc aagaaagatg ttgagttcct   4320
caagaaggag cttgagagca tgcacgctgc cctcatcaag gttggcgagg tgccgcggga   4380
ccagctcgac aggcaagtca agctctgggc cgacgaggtc agagagctct cctacaacat   4440
ggaggatgtc gtcgacaagt tcctcgtacg cgtcgacggc gacggcattc agcagcctca   4500
cgacaactcc ggcagattta aggagctcaa gaacaagatg atcggcttgt ttaagaaagg   4560
caggaatcac catcgcatag ctgacgcgat caaggaaatc aaggagcaac tccaggaggt   4620
ggctgctagg cgtgacagga acaaggtagc tgttcctaat cctatggaac caattactat   4680
cgatccttgt cttcgagctt tgtacgcaga agcgacagag ctagttggca tatatgggaa   4740
gagggatgag gagctcatga ggttgctctc catggagggt gatgatgcct ctaacaagag   4800
actaaagaag gtctccattg ttggatttgg agggttgggc aagaccactc ttgctagagc   4860
agtatacgac aagattaaag gtgattttga ttgtcgggca tttgttcccg tcggtcagaa   4920
ccctgacatg aagaaggttt aagggatat cctcattgat ctcggcaacc ctcactcaga   4980
tcttgctata ctggatgaca aacaacttgt taaaaagctt catgatttcc tagagaacaa   5040
aaggtatgca tcagttacag caacaattta cactatatga tatatttgtt tcgcatgcta   5100
gctgtacaag taatactgta atagtagtgt gtaaatatat tgtacgtcac acggaagggt   5160
tcagaataat tttcaaggtc acctttactg atgtatgcag tatgcactaa actgtaaacc   5220
ttataggtgc tcacttttcaa gcctgtataa gtttatatgt ttgattcttt cctcctttat   5280
cgaaatatat aattagtaac tacttcctgt tgcatttatt acaatggctg aaacttattg   5340
gcattggtcc aagaaatcca tctaaacttc tttagaatct tactatcagc aaaatataga   5400
caaaaggata atgctacact atttgagtgg tcttcccaa tatatctacc tgaccaattt   5460
aacttccgta gttaattttta ttttacgtgt gatcactgat gcagcaattt gctatttgtg   5520
ttttactccc ttgaatctta aatatagttc attttgttca tcatctgact gtaggatcat   5580
aatacatgct tcatgagaat cagattatcg agtttgagac gcatgctgct tactagttcg   5640
tttttgaata tatgccctta ccgatgtata gttccaccca tatattcata tggcgctcag   5700
```

```
ctttgtgata ttatagacct tacactgata ctctgaacta atgtaggtat cttgtcataa   5760
ttgatgatat atgggacgaa atgttgtggg aaggcatcaa ctttgctttc tccaatagga   5820
ataatctagg cagtcggcta atcaccacaa cccgcaattt cgatgtctcc aaatcatgtt   5880
gcttatcggc tgatgattca atatataaaa tgaaacctct ttctactgat gactccagaa   5940
ggctcttcca taagagaata tttcctgacg ctggtggatg tccaagtgaa tttcaacaag   6000
tgtctgaaga catattgaag aaatgtggtg gagtaccact ggccatcatt actattgcta   6060
gtgctttggc tagtggccag catgtgaaac caaagcatga gtgggatatt ctactccagt   6120
cccttggctc cggagtaaca aaagataata gtttggttga gatgcggaga atactatctt   6180
tcagctatta taatctaccg tctcatctga aaacttgtct actttaccta tgtatatatc   6240
cagaagatag caccattggt agagatagac tgatatggaa gtgggtggcc gaaggatttg   6300
tccaccatgg agatcaaggg accagtctgt ttttggtcgg attaaactac ttcaaccagc   6360
tcattaatag aagtatgatc cagccaatat atgatgaact aggccaggta catgcttgcc   6420
gtgtacatga tatggttctt gatcttatct gcaacttctc acatgaagca aagtttgtta   6480
atgtattgga tggcacaggg aatagcatat cttcacaaag taatgtccgt cgtttgtccc   6540
ttcagaataa aatggaagat catcaagcca agcctctcac aaatatcatg agtatgtcac   6600
gagtgaggtc aattactatc tttccacctg ctgttagtat catgccaagt ctgtcaatgt   6660
ttgaagttct gcgtgtactt gatctgtcga actgtgattt gggaaaaagt agcagcctgc   6720
agcttaacct caagggtgtt ggacatttaa tccacctaag gtaccttgat ctacaaggca   6780
ctcaaattag tgaactcccg actgagatag gaaacctgca atttttggag gtgttggatc   6840
ttgacaacaa ttatgagcta gatgaattgc cttccactct ttttaaattg agaagattaa   6900
tctacttaaa tgttatgttg tataaggtgg ttccaactcc tggtgtgttg cagaatatga   6960
catccattga agtgttgagg ggggtcttgg tctctctgaa cattattgca caagagcttg   7020
gcaacctgac aaggctgagg gagcttaaga tttgcttcaa ggatggtaat ttggattcat   7080
ataaactttt cgtgaagtct ctgggcaacc tgcatcatat cgaaagccta agtattagtt   7140
acaattccaa agaaacatct tttgaactga tggatctctt gggagagcgt tgggtgcctc   7200
ctgtacatct ccgcgaattt gtgtcttgga tgcccagcca actctctgca ttgcgaggat   7260
ggataaagag agaccctcg catctctcga acctctccga gttaatcctc tggccagtga   7320
aggaagtgca gcaggaggac gtggaaatca ttgggggggtt gctgtccctt cgccgtctct   7380
ggataaagag cacccaccaa acacagcggc tgctagtcat tcgtgcagat gggttccgct   7440
gcatgatgga ctttgagttg aattgtggat cagcagcgca aatcatgttt gaaccaggag   7500
ctttgccgag gcggaagta cttgtgttca gcctgggcgt gcgggtggcg caagaggatg   7560
gaaactgtgg tttcgacttg ggcctgcagg ggaacctgct ctcccttcgg catgatgtct   7620
ttgttcgtat atattgtggt ggggcgaggg ttggggaggc aaaggaagcg gaggctgcgg   7680
tgaggcacgc gctcgaagcc catcccaacc atccccgat tgatattgag atgacccgt   7740 atatagcaga aggtactcac gtcgcatcta actaattact cgtgcactta cgcatgtgtt   7800 ttttttctc aatgacggac tgaccttatt actttctgca tgggtttgat ctctgaatct   7860
cctcaggtgc tcgtgatgat gatttgtgtg aggagaactg atttatgatg tagaggactc   7920
acagtgaatc aggtgtgctc tccatatgta tgtatttact ggtcatattt tccactacct   7980
ttctttctcc atctctagag ctcagcttgt ttctacattg ataaactgcg ctacagaagt   8040
```

```
tgcttagtct gaaaccacgc aatctcattt ttggcaagtg ctgatgaaag ctaatgattt    8100
taggattttt atgcaaactt gtagaaggat agtttgtagt cacctgcta taaatagttt     8160 ttaggatttt tcgacagaag tagattttgg gaagatttgt ggataggga tgttggtttt     8220 agctgacaag tgacaagtac tccatgttat acaatttatt tttatgtaag ggtatctctg    8280
tagctctcga gtcctagcac taatttaact cactgaaatt tagaagggg ctactgattg     8340 tgaaggtttt actctgagaa ataagcagga tttgtaata ggggtatttt ctgttcattc     8400
tatgcatata gctctcgaaa ttcacagttg aaacaaccct gctgaaaatt tggtatgta    8460 aaagttctac ttaattaaga tcaaattatt actatggtta gcaatcagaa atatagtatc    8520
ttaaccggag ataatctaaa tcatagaggt agtgtggtgc aggaaaactg tttttttttt    8580
ttgcagtaga aaagagtcaa tggatcatat gcttttaac tgttcgattg ctctcgttat    8640
atttggaaca catgtggtct taatacagtt cctgttagca tggagagact tagttattgg    8700
gtaatgaatt ccaggggtaa agataggaat ctggtttctg atagggtagt ggctgttatt    8760
tgaaaacgag gaaagataat tgcttgaaaa aaaaattcac tatggatccc agctgtacgt   8820
gtgtaggttg taaagctgta tattgcatat tttactggtc tagcttacag agaaaagaat    8880
tgcacgattg caggtagcag gggcgtggga ttactgctgg tggcatcgga gaatttgtgt    8940
ggtttcacta acattttggg tgggcgccgg ccctgcaaag aattgaagga tggaaaggtt    9000
tcgaccttgg ctggaagttg tgtgatgagc ctgcagaaaa agatattgct tggttttgta    9060
atgaattagt aacggtgttg gggtgaattg atccttaccg aaaaaatgtt ttccgcggct   9120
ttgttttact ctctccgtcc aaaagtactt gtcatcaaaa tggacaaaaa aagatgtatc    9180
tagaactaaa atacatctag atatatctcc ttttcttcat tttgatgaca agtatttccg    9240
gacggaggga gtacaaagca accaaccgaa ccattcaggg ataggtgctg ggcggaagca    9300
gcacagtcac gcccaaaaga aacgacagag aaagagcaaa agaaacaaat gccgacaacg    9360
gcggatcaac aaaaacgaag aagcaaagca attgctgcgc ccaccaagat cttccactag    9420
gctccaagac tccgaagcgc cggcacctat caacacctcc aagaaggatc gcgacgatga    9480
cgacgctgtt gccaagggtt ctcccggta cacgacgagg cgagaggaag ggtagccccc     9540
gacgccctcc cggaaggcca ggtggcaccc ataggcgcca ccgcgccggt gtcagccatg    9600
ccgacagggg tttccccgat cccaacccac acctcggacg ctccgaagcc taccaccaaa    9660
ccaaccacca cccttcgcca acacggtcaa gaggcccaca cgccgtctca ccacggcacc    9720
gtgaagtgag gatagcacgg cgaagaatca gagccgggat tagggcatca acaccttcgg    9780
cacgtgggag ggccc                                                     9795
```

<210> SEQ ID NO 12  
<211> LENGTH: 8001  
<212> TYPE: DNA  
<213> ORGANISM: Artificial Sequence  
<220> FEATURE:  
<223> OTHER INFORMATION: pVecBarSr50 expression construct

<400> SEQUENCE: 12

```
tgcgtaacaa cttgcttgcc ttcactctct tcctattttt ctgcatgtag attaatgtac      60
tagtttatga atgcatagtt tgtagcatgt ccggctcctc cccaccaccc gtagaacgca    120
accgctgctc tgtcccgcct cgaccgtctg ccccttccta tagcattagc gctgctcaca    180
tccacctcaa ggcactgcct ccatccgccc agtttgagat tgggacgtgt atctttgggt    240
ctcgggtgat gatgcatccg aatcgagaga aataatttag aaactgaaaa aataagtcaa    300
```

```
aattgtgatt tgtttagaac aaacatgata ttatgttaca ctcatgtgaa aagattcacg    360
aatgaatgac tttcatgtac tcttgccgaa agaaaccaaa atcgacacta tataaaagtt    420
actattcatg cttttatact cactaatatc ttttttgccc agaagtcatt ctttcgcgaa    480
gagtatcaca ctagatctag tatgttccca aaatgttcca gaattttgtg acctttttg    540 caatttctaa attatttctt caattcaggt gcattgggac ccgagaccca ttgggtattt    600
tcggtatcga ttgcttttga gtactgcata agagtattta ccacctggca aatgtctgat    660
tttaggaggg agggtaaat gcatgatgtg gactgaccaa ccaaccgaga gagattcaga    720
gaaatgagag gatcagagta attgtagtga agtagaggat cagagtagta tgcaattatt    780
ttctttgaat ccctgtgtct ctatgaccca ctgaatagac agatcagcca aaagcagtac    840
tgttccgagg gatcgtgggg gcttctttcc accgcaccca ccgaaagcac tactccattt    900
cttctttacg caccttctcc cacatccaac gcatcgacca ctgatgaaca aacacatgag    960
ccaaaagcat tactgttccg agggattcgt atcttgactt gctgttgtgg gtcttcctct   1020
gctcctcgcc tccactgagt gctcccttaa tctcgtctca gtcctctcct tcatttctaa   1080
gttgtgagct gaaactatgt gtttattgtt acagtttagc gtatgttcat gatcactcag   1140
ttttgtaggt atggtttcag gttctgttac agtttaacgt gtgctatgga agtctctcat   1200
tgagaagcta ggtctcgcgc acatggatac atccgagtgg cccatgtacg attccgtcta   1260
ccagtggtgg gacaagagaa ccgacaaccg caatcctaac cggcaagcta tggcttccct   1320
caccatgctc gtctcgtgga ccatttggaa tgaaagaaac gcacgggtgt tccgccacaa   1380
gagtgcgcca cccaccatcc tactcaccgc catcgtcgag gaggccaagc tttggatggt   1440
cgcgggcgca aagcaattag gaatatttt tctaggcgag tagttgtcat gacgtatgtg   1500
cgggtgtgtt gtaactctct aaactctatt cttcccttat ttaatagatg aggcaaagct   1560
tatgcctccg tttcgaaaaa aaaaacagtt taacgtgtgc tcatcaactg aaactatgct   1620
tcaggcattg agtattcact accaaatcga aattttcaaa ctgaacggag ggattcaatt   1680
ctttacccgt tgcaaagatg aaagctagtg aaaaaaatta atagtgtcat tgcctgataa   1740
atgcatgaag gatggagaga cggtgggggc tctgtatcat tgcctggcag gtgcatgagg   1800
tagattcaga gaaatgagag gacgtacaat tattgtctct gagtcactgt ccatgaatga   1860
cccactgcac tgaatgattg catgagccaa aagcactact attcagaggc atcgtgggtg   1920
ctctcttatc tcttgacctg ctgttgttgg tctgcatctc agtcctctcc tccattgcgc   1980
tgcctggaat aaggtcgatc cggcttcttg attggtgagc tcgtccaacc tccagctcac   2040
ccctgccaac tgactgccag agacctttga cacctgtgga ggtatatatc ctttcgattt   2100
ctttccagct gaagtacgct tggatctaaa aacttagttg tccagagctt gggagactga   2160
tttgtgttgg ttgaatccag ggagggagtg gaacagctag caagaagcat ggagcttccg   2220
gtcattattc agagcaccac acatggaatc cactgacctg gctagcggcc tcgtaacttc   2280
gtctcatctt tcttgctact gaaatatatt tcagatccac accttcccgt ccagatcgag   2340
agagagagac cgccccttcc aactgacgcc tgtgaagcta ggatctaaaa aatgacttct   2400
cctgctctac tgaaatcttt cacacccgca cgttcttgtt aatctgctga tttcctatat   2460
tataatttct tatttcgtcc ggattcagtg aagttgccgc tgtgttgtcc catccatatt   2520
cagtgcagcg accctcacgc atctggcctc tggtatgcca ccgccgtact ctgctctgcc   2580
gtgaagaatt aaggtgggct tggtccagat ctcgcagttc tattctggtc agttctatag   2640
```

```
ctcgatgaaa ttaaagcttc acacaatttc gattggatca cggctcccct tatgctaagc    2700
tttaatttgg cagctctgtt ctagagctcg ttcacacaat ttggattgca ttacagctcc    2760
cctcattcat caatttacag gtttccaatt gatcgatcca gagagctcat cctcctgctc    2820
tcatgaatat tgtcacgggg gccatgggca gcctgatccc caagttgggc gagctgctca    2880
tggatgagta caagctgcac aagcgcatca agaaagatgt tgagttcctc aagaaggagc    2940
ttgagagcat gcacgctgcc ctcatcaagg ttggcgaggt gccgcgggac cagctcgaca    3000
ggcaagtcaa gctctgggcc gacgaggtca gagagctctc ctacaacatg gaggatgtcg    3060
tcgacaagtt cctcgtacgc gtcgacggcg acggcattca gcagcctcac gacaactccg    3120
gcagatttaa ggagctcaag aacaagatga tcggcttgtt taagaaaggc aggaatcacc    3180
atcgcatagc tgacgcgatc aaggaaatca aggagcaact ccaggaggtg gctgctaggc    3240
gtgacaggaa caaggtagct gttcctaatc ctatggaacc aattactatc gatccttgtc    3300
ttcgagcttt gtacgcagaa gcgacagagc tagttggcat atatgggaag agggatgagg    3360
agctcatgag gttgctctcc atggagggtg atgatgcctc taacaagaga ctaaagaagg    3420
tctccattgt tggatttgga gggttgggca agaccactct tgctagagca gtatacgaca    3480
agattaaagg tgattttgat tgtcgggcat tgttcccgt cggtcagaac cctgacatga    3540
agaaggtttt aagggatatc ctcattgatc tcggcaaccc tcactcagat cttgctatac    3600
tggatgacaa acaacttgtt aaaaagcttc atgatttcct agagaacaaa aggtatgcat    3660
cagttacagc aacaatttac actatatgat atatttgttt cgcatgctag ctgtacaagt    3720
aatactgtaa tagtagtgtg taaatatatt gtacgtcaca cggaagggtt cagaataatt    3780
ttcaaggtca cctttactga tgtatgcagt atgcactaaa ctgtaaacct tataggtgct    3840
cactttcaag cctgtataag tttatatgtt tgattctttc ctcctttatc gaaatatata    3900
attagtaact acttcctgtt gcatttatta caatggctga aacttattgg cattggtcca    3960
agaaatccat ctaaacttct ttagaatctt actatcagca aaatatagac aaaaggataa    4020
tgctacacta tttgagtggg tcttcccaat atatctacct gaccaattta acttccgtag    4080
ttaattttat tttacgtgtg atcactgatg cagcaatttg ctatttgtgt tttactccct    4140
tgaatcttaa atatagttca ttttgttcat catctgactg taggatcata atacatgctt    4200
catgagaatc agattatcga gtttgagacg catgctgctt actagttcgt ttttgaatat    4260
atgcccttac cgatgtatag ttccacccat atattcatat ggcgctcagc tttgtgatat    4320
tatagacctt acactgatac tctgaactaa tgtaggtatc ttgtcataat tgatgatata    4380
tgggacgaaa tgttgtggga aggcatcaac tttgctttct ccaataggaa taatctaggc    4440
agtcggctaa tcaccacaac ccgcaatttc gatgtctcca aatcatgttg cttatcggct    4500
gatgattcaa tatataaaat gaaacctctt tctactgatg actccagaag gctcttccat    4560
aagagaatat ttcctgacgc tggtggatgt ccaagtgaat ttcaacaagt gtctgaagac    4620
atattgaaga aatgtggtgg agtaccactg gccatcatta ctattgctag tgctttggct    4680
agtggccagc atgtgaaacc aaagcatgag tgggatattc tactccagtc ccttggctcc    4740
ggagtaacaa aagataatag tttggttgag atgcggagaa tactatcttt cagctattat    4800
aatctaccgt ctcatctgaa aacttgtcta ctttacctat gtatatatcc agaagatagc    4860
accattggta gagatagact gatatggaag tgggtggccg aaggatttgt ccaccatgga    4920
gatcaaggga ccagtctgtt tttggtcgga ttaaactact tcaaccagct cattaataga    4980
agtatgatcc agccaatata tgatgaacta ggccaggtac atgcttgccg tgtacatgat    5040
```

```
atggttcttg atcttatctg caacttctca catgaagcaa agtttgttaa tgtattggat   5100
ggcacaggga atagcatatc ttcacaaagt aatgtccgtc gtttgtccct tcagaataaa   5160
atggaagatc atcaagccaa gcctctcaca aatatcatga gtatgtcacg agtgaggtca   5220
attactatct ttccacctgc tgttagtatc atgccaagtc tgtcaatgtt tgaagttctg   5280
cgtgtacttg atctgtcgaa ctgtgatttg ggaaaaagta gcagcctgca gcttaacctc   5340
aagggtgttg acatttaat ccacctaagg taccttgatc tacaaggcac tcaaattagt    5400
gaactcccga ctgagatagg aaacctgcaa ttttttggagg tgttggatct tgacaacaat  5460
tatgagctag atgaattgcc ttccactctt tttaaattga agagattaat ctacttaaat   5520
gttatgttgt ataaggtggt tccaactcct ggtgtgttgc agaatatgac atccattgaa   5580
gtgttgaggg gggtcttggt ctctctgaac attattgcac aagagcttgg caacctgaca   5640
aggctgaggg agcttaagat ttgcttcaag gatggtaatt tggattcata taaacttttc   5700
gtgaagtctc tgggcaacct gcatcatatc gaaagcctaa gtattagtta caattccaaa   5760
gaaacatctt ttgaactgat ggatctcttg ggagagcgtt gggtgcctcc tgtacatctc   5820
cgcgaatttg tgtcttggat gcccagccaa ctctctgcat tgcgaggatg gataaagaga   5880 gaccctcgc atctctcgaa cctctccgag ttaatcctct ggccagtgaa ggaagtgcag    5940
caggaggacg tggaaatcat tggggggttg ctgtcccttc gccgtctctg gataaagagc   6000
acccaccaaa cacagcggct gctagtcatt cgtgcagatg ggttccgctg catgatggac   6060
tttgagttga attgtggatc agcagcgcaa atcatgtttg aaccaggagc tttgccgagg   6120
gcggaagtac ttgtgttcag cctgggcgtg cgggtggcgc aagaggatgg aaactgtggt   6180
ttcgacttgg gcctgcaggg gaacctgctc tcccttcggc atgatgtctt tgttcgtata   6240
tattgtggtg gggcgagggt tggggaggca aaggaagcgg aggctgcggt gaggcacgcg   6300
ctcgaagccc atcccaacca tcccccgatt gatattgaga tgaccccgta tatagcagaa   6360
ggtactcacg tcgcatctaa ctaattactc gtgcacttac gcatgtgttt tttttctca    6420 atgacggact gacctattta ctttctgcat gggtttgatc tctgaatctc ctcaggtgct   6480
cgtgatgatg atttgtgtga ggagaactga tttatgatgt agaggactca cagtgaatca   6540
ggtgtgctct ccatatgtat gtatttactg gtcatatttt ccactacctt tctttctcca   6600
tctctagagc tcagcttgtt tctacattga taaactgcgc tacagaagtt gcttagtctg   6660
aaaccacgca atctcatttt tggcaagtgc tgatgaaagc taatgatttt aggatttta   6720 tgcaaacttg tagaaggata gtttgtagta cacctgctat aaatagtttt taggatttt   6780 cgacagaagt agatttgg aagatttgtg gataggggat gttggtttta gctgacaagt    6840
gacaagtact ccatgttata caatttattt ttatgtaagg gtatctctgt agctctcgag   6900
tcctagcact aatttaactc actgaaattt agaaggggc tactgattgt gaaggtttta   6960
ctctgagaaa taagcaggat ttgtgaatag gggtattttc tgttcattct atgcatatag   7020
ctctcgaaat tcacagttga aacaaccctg ctgaaaattt tggtatgtaa agttctact    7080 taattaagat caaattatta ctatggttag caatcagaaa tatagtatct taaccggaga   7140
taatctaaat catagaggta gtgtggtgca ggaaaactgt ttttttttt tgcagtagaa    7200 aagagtcaat ggatcatatg cttttaact gttcgattgc tctcgttata tttggaacac    7260
atgtggtctt aatacagttc ctgttagcat ggagagactt agttattggg taatgaattc   7320 cagggtaaa gataggaatc tggtttctga tagggtagtg gctgttattt gaaaacgagg    7380
```

-continued

```
aaagataatt gcttgaaaaa aaaattcact atggatccca gctgtacgtg tgtaggttgt    7440
aaagctgtat attgcatatt ttactggtct agcttacaga gaaaagaatt gcacgattgc    7500
aggtagcagg ggcgtgggat tactgctggt ggcatcggag aatttgtgtg gtttcactaa    7560
cattttgggt gggcgccggc cctgcaaaga attgaaggat ggaaaggttt cgaccttggc    7620
tggaagttgt gtgatgagcc tgcagaaaaa gatattgctt ggttttgtaa tgaattagta    7680
acggtgttgg ggtgaattga tccttaccga aaaaatgttt tccgcggctt tgttttactc    7740
tctccgtcca aaagtacttg tcatcaaaat ggacaaaaaa agatgtatct agaactaaaa    7800
tacatctaga tatatctcct tttcttcatt ttgatgacaa gtatttccgg acggagggag    7860
tacaaagcaa ccaaccgaac cattcaggga taggtgctgg gcggaagcag cacagtcacg    7920
cccaaaagaa acgacagaga aagagcaaaa gaaacaaatg ccgacaacgg cggatcaaca    7980
aaaacgaaga agcaaagcaa t                                              8001
```

<210> SEQ ID NO 13
<211> LENGTH: 961
<212> TYPE: PRT
<213> ORGANISM: Aegilops tauschii

<400> SEQUENCE: 13

```
Met Asp Ile Val Thr Gly Ala Ile Ala Lys Leu Ile Pro Lys Leu Gly
1               5                   10                  15

Glu Leu Leu Val Gly Glu Tyr Lys Leu His Lys Gly Val Lys Lys Asn
            20                  25                  30

Ile Glu Asp Leu Leu Lys Glu Leu Lys Thr Met Asn Ala Ala Leu Ile
        35                  40                  45

Lys Ile Gly Glu Val Pro Pro Asp Gln Leu Asp Ser Gln Asp Lys Leu
    50                  55                  60

Trp Ala Asp Glu Val Arg Glu Leu Ser Tyr Val Ile Glu Asp Ala Val
65                  70                  75                  80

Asp Lys Phe Leu Val Arg Val His Gly Val Glu Pro Asp Asp Asn Thr
                85                  90                  95

Asn Gly Phe Lys Gly Leu Met Lys Arg Thr Thr Lys Leu Leu Lys Lys
            100                 105                 110

Val Val Asp Lys His Gly Ile Ala His Ala Ile Lys Asp Ile Lys Lys
        115                 120                 125

Glu Leu Gln Glu Val Ala Ala Arg Arg Asp Arg Asn Lys Phe Asp Gly
    130                 135                 140

Ile Ala Ser Ile Pro Thr Glu Ala Ile Asp Pro Arg Leu Arg Ala Leu
145                 150                 155                 160

Tyr Ile Glu Ala Ala Glu Leu Val Gly Ile Tyr Gly Lys Arg Asp Gln
                165                 170                 175

Glu Leu Met Ser Leu Leu Ser Leu Glu Gly Asp Asp Ala Ser Thr Lys
            180                 185                 190

Lys Leu Lys Lys Val Ser Ile Val Gly Phe Gly Gly Leu Gly Lys Thr
        195                 200                 205

Thr Leu Ala Lys Ala Val Tyr Glu Lys Ile Lys Gly Asp Phe Asp Cys
    210                 215                 220

His Ala Phe Val Pro Val Gly Gln Asn Pro Asp Lys Lys Val Phe
225                 230                 235                 240

Arg Asp Ile Leu Met Asp Leu Ser Asn Ser Asn Ser Asp Leu Ala Leu
                245                 250                 255

Leu Asp Glu Arg Gln Leu Ile Asn Lys Leu His Lys Phe Leu Glu Asn
```

-continued

```
                260                 265                 270
Lys Arg Tyr Leu Val Ile Ile Asp Asp Val Trp Asp Glu Gly Leu Trp
                275                 280                 285
Lys Asp Ile Asn Leu Ala Phe Ser Asn Arg Asn Asn Leu Gly Ser Arg
                290                 295                 300
Leu Ile Ile Thr Thr Arg Ile Phe Gly Val Ser Glu Ser Cys Cys Ser
305                 310                 315                 320
Ser Ala Asp Asp Pro Val Tyr Glu Ile Glu Pro Leu Ser Ile Asp Asp
                325                 330                 335
Ser Ser Lys Leu Phe Tyr Thr Arg Ile Phe Ser Asp Ser Gly Cys Pro
                340                 345                 350
Lys Glu Phe Glu Gln Val Ser Lys Asp Ile Leu Lys Lys Cys Gly Gly
                355                 360                 365
Val Pro Leu Ala Ile Ile Thr Ile Ala Ser Ala Leu Ala Ser Gly Gln
                370                 375                 380
Gln Val Lys Pro Lys His Glu Trp Asp Ile Leu Leu Gln Ser Leu Gly
385                 390                 395                 400
Ser Gly Val Thr Lys Asp Asn Ser Leu Val Glu Met Arg Arg Ile Leu
                405                 410                 415
Ser Phe Ser Tyr Tyr Asn Leu Pro Ser His Leu Lys Thr Cys Leu Leu
                420                 425                 430
Tyr Leu Cys Ile Tyr Pro Glu Asp Ser Met Ile His Arg Asp Arg Leu
                435                 440                 445
Ile Trp Lys Trp Val Ala Glu Gly Phe Val His His Gly Asp Gln Gly
                450                 455                 460
Thr Ser Leu Phe Leu Val Gly Leu Asn Tyr Phe Asn Gln Leu Ile Asn
465                 470                 475                 480
Arg Ser Met Leu Gln Pro Ile Tyr Ser Asp Met Gly Asn Val Tyr Ala
                485                 490                 495
Cys Arg Val His Asp Met Val Leu Asp Leu Ile Cys Asn Leu Ser His
                500                 505                 510
Glu Ala Lys Phe Val Asn Val Phe Asp Gly Thr Gly Asn Ile Met Ser
                515                 520                 525
Ser Gln Ser Asn Val Arg Arg Leu Ser Leu Gln Asn Lys Asn Glu Asp
                530                 535                 540
His Gln Ala Lys Pro Leu Thr Asn Ile Met Ser Ile Ser Gln Val Arg
545                 550                 555                 560
Ser Ile Thr Ile Phe Pro Pro Ala Val Ser Ile Met Pro Ala Leu Ser
                565                 570                 575
Arg Phe Glu Val Leu Arg Val Leu Asp Leu Ser Asp Cys Asn Leu Gly
                580                 585                 590
Glu Ser Ser Ser Leu Gln Pro Asn Leu Lys Gly Val Gly His Leu Ile
                595                 600                 605
His Leu Arg Tyr Leu Gly Leu Ser Gly Thr Arg Ile Ser Lys Leu Pro
                610                 615                 620
Ala Glu Ile Gly Thr Leu Gln Phe Leu Glu Val Leu Asp Leu Gly Tyr
625                 630                 635                 640
Asn His Glu Leu Asp Glu Leu Pro Ser Thr Leu Phe Lys Leu Arg Arg
                645                 650                 655
Leu Ile Tyr Leu Asn Val Ser Pro Tyr Lys Val Val Pro Thr Pro Gly
                660                 665                 670
Val Leu Gln Asn Met Thr Ser Ile Glu Val Leu Arg Gly Ile Phe Val
                675                 680                 685
```

```
Ser Leu Asn Ile Ile Ala Gln Glu Leu Gly Lys Leu Ala Arg Leu Arg
        690                 695                 700

Glu Leu Gln Ile Tyr Phe Lys Asp Gly Ser Leu Asp Leu Tyr Glu Gly
705                 710                 715                 720

Phe Val Lys Ser Leu Cys Asn Leu His His Ile Glu Ser Leu Ile Val
                725                 730                 735

Ser Cys Asn Ser Gly Glu Thr Ser Phe Glu Leu Met Asp Leu Leu Gly
            740                 745                 750

Glu Gln Trp Val Pro Val His Leu Arg Glu Phe Val Ser Glu Met
        755                 760                 765

Pro Ser Gln Leu Ser Ala Leu Arg Gly Trp Ile Lys Arg Asp Pro Ser
770                 775                 780

His Leu Ser Asn Leu Ser Glu Leu Ile Leu Pro Thr Val Lys Glu Val
785                 790                 795                 800

Gln Gln Glu Asp Val Glu Ile Ile Gly Leu Leu Ser Leu Arg Arg
                805                 810                 815

Leu Leu Ile Glu Ser Thr His Gln Thr Gln Arg Leu Leu Val Ile Arg
            820                 825                 830

Ala Asp Gly Phe Arg Cys Met Val Asp Phe Tyr Leu Asn Cys Gly Ser
        835                 840                 845

Ala Thr Gln Ile Met Phe Glu Ser Gly Ala Leu Pro Arg Ala Glu Glu
850                 855                 860

Val Cys Phe Ser Leu Gly Val Arg Val Ala Lys Glu Asp Gly Asn Arg
865                 870                 875                 880

Gly Phe Asp Leu Gly Leu Gln Gly Asn Leu Leu Ser Leu Arg Arg Val
                885                 890                 895

Val Trp Val Lys Met Tyr Cys Gly Gly Ala Arg Val Gly Glu Ala Lys
            900                 905                 910

Glu Ala Lys Ala Ala Val Arg His Ala Leu Glu Asp His Pro Asn His
        915                 920                 925

Pro Pro Ile Gln Ile Asn Met Phe Pro Arg Ile Ala Glu Gly Ala Gln
930                 935                 940

Asp Asp Asp Leu Met Cys Tyr Pro Val Gly Gly Pro Ile Ser Asp Ala
945                 950                 955                 960

Glu

<210> SEQ ID NO 14
<211> LENGTH: 961
<212> TYPE: PRT
<213> ORGANISM: Aegilops tauschii

<400> SEQUENCE: 14

Met Asp Ile Val Thr Gly Ala Ile Ala Lys Leu Ile Pro Lys Leu Gly
1               5                   10                  15

Glu Leu Leu Val Gly Glu Tyr Lys Leu His Lys Gly Val Lys Lys Asn
            20                  25                  30

Ile Glu Asp Leu Leu Lys Glu Leu Lys Thr Met Asn Ala Ala Leu Ile
        35                  40                  45

Lys Ile Gly Glu Val Pro Pro Asp Gln Leu Asp Ser Gln Asp Lys Leu
    50                  55                  60

Trp Ala Asp Glu Val Arg Glu Leu Ser Tyr Val Ile Glu Asp Ala Val
65                  70                  75                  80

Asp Lys Phe Leu Val Arg Val His Gly Val Glu Pro Asp Asp Asn Thr
                85                  90                  95
```

```
Asn Gly Phe Lys Gly Leu Met Lys Arg Thr Thr Lys Leu Leu Lys Lys
            100                 105                 110

Val Val Asp Lys His Gly Ile Ala His Ala Ile Lys Asp Ile Lys Lys
115                 120                 125

Glu Leu Gln Glu Val Ala Ala Arg Arg Asp Arg Asn Lys Phe Asp Gly
        130                 135                 140

Ile Ala Ser Ile Pro Thr Glu Ala Ile Asp Pro Arg Leu Arg Ala Leu
145                 150                 155                 160

Tyr Ile Glu Ala Ala Glu Leu Val Gly Ile Tyr Gly Lys Arg Asp Gln
                165                 170                 175

Glu Leu Met Ser Leu Leu Ser Leu Glu Gly Asp Ala Ser Thr Lys
            180                 185                 190

Lys Leu Lys Lys Val Ser Ile Val Gly Phe Gly Gly Leu Gly Lys Thr
        195                 200                 205

Thr Leu Ala Lys Ala Val Tyr Glu Lys Ile Lys Gly Asp Phe Asp Cys
210                 215                 220

His Ala Phe Val Pro Val Gly Gln Asn Pro Asp Lys Lys Val Phe
225                 230                 235                 240

Arg Asp Ile Leu Met Asp Leu Ser Asn Ser Asn Ser Asp Leu Ala Leu
            245                 250                 255

Leu Asp Glu Arg Gln Leu Ile Asn Lys Leu His Lys Phe Leu Glu Asn
        260                 265                 270

Lys Arg Tyr Leu Val Ile Ile Asp Asp Val Trp Asp Glu Gly Leu Trp
    275                 280                 285

Lys Asp Ile Asn Leu Ala Phe Ser Asn Arg Asn Asn Leu Gly Ser Arg
290                 295                 300

Leu Ile Ile Thr Thr Arg Ile Phe Gly Val Ser Glu Ser Cys Cys Ser
305                 310                 315                 320

Ser Ala Asp Asp Pro Val Tyr Glu Ile Glu Pro Leu Ser Ile Asp Asp
            325                 330                 335

Ser Ser Lys Leu Phe Tyr Thr Arg Ile Phe Ser Asp Ser Gly Cys Pro
        340                 345                 350

Lys Glu Phe Glu Gln Val Ser Lys Asp Ile Leu Lys Lys Cys Gly Gly
    355                 360                 365

Val Pro Leu Ala Ile Ile Thr Ile Ala Ser Ala Leu Ala Ser Gly Gln
370                 375                 380

Gln Val Lys Pro Lys His Glu Trp Asp Ile Leu Leu Gln Ser Leu Gly
385                 390                 395                 400

Ser Gly Val Thr Lys Asp Asn Ser Leu Val Glu Met Arg Arg Ile Leu
            405                 410                 415

Ser Phe Ser Tyr Tyr Asn Leu Pro Ser His Leu Lys Thr Cys Leu Leu
        420                 425                 430

Tyr Leu Cys Ile Tyr Pro Glu Asp Ser Met Ile His Arg Asp Arg Leu
    435                 440                 445

Ile Trp Lys Trp Val Ala Glu Gly Phe Val His Gly Asp Gln Gly
450                 455                 460

Thr Ser Leu Phe Leu Val Gly Leu Asn Tyr Phe Asn Gln Leu Ile Asn
465                 470                 475                 480

Arg Ser Met Leu Gln Pro Ile Tyr Ser Asp Met Gly Asn Val Tyr Ala
            485                 490                 495

Cys Arg Val His Asp Met Val Leu Asp Leu Ile Cys Asn Leu Ser His
        500                 505                 510
```

```
Glu Ala Lys Phe Val Asn Val Phe Asp Gly Thr Gly Asn Ile Met Ser
            515                 520                 525

Ser Gln Ser Asn Val Arg Arg Leu Ser Leu Gln Asn Lys Asn Glu Asp
        530                 535                 540

His Gln Ala Lys Pro Leu Thr Asn Ile Met Ser Ile Ser Gln Val Arg
545                 550                 555                 560

Ser Ile Thr Ile Phe Pro Pro Ala Val Ser Ile Met Pro Ala Leu Ser
                565                 570                 575

Arg Phe Glu Val Leu Arg Val Leu Asp Leu Ser Asn Cys Asn Leu Gly
            580                 585                 590

Glu Ser Ser Ser Leu Gln Pro Asn Leu Lys Gly Val Gly His Leu Ile
        595                 600                 605

His Leu Arg Tyr Leu Gly Leu Ser Gly Thr Arg Ile Ser Lys Leu Pro
610                 615                 620

Ala Glu Ile Gly Thr Leu Gln Phe Leu Glu Val Leu Asp Leu Gly Tyr
625                 630                 635                 640

Asn His Glu Leu Asp Glu Leu Pro Ser Thr Leu Phe Lys Leu Arg Arg
                645                 650                 655

Leu Ile Tyr Leu Asn Val Ser Pro Tyr Lys Val Val Pro Thr Pro Gly
            660                 665                 670

Val Leu Gln Asn Met Thr Ser Ile Glu Val Leu Arg Gly Ile Phe Val
        675                 680                 685

Ser Leu Asn Ile Ile Ala Gln Glu Leu Gly Lys Leu Ala Arg Leu Arg
    690                 695                 700

Glu Leu Gln Ile Tyr Phe Lys Asp Gly Ser Leu Asp Leu Tyr Glu Gly
705                 710                 715                 720

Phe Val Lys Ser Leu Cys Asn Leu His His Ile Glu Ser Leu Ile Val
                725                 730                 735

Ser Cys Asn Ser Gly Glu Thr Ser Phe Glu Leu Met Asp Leu Leu Gly
            740                 745                 750

Glu Gln Trp Val Pro Pro Val His Leu Arg Glu Phe Val Ser Glu Met
        755                 760                 765

Pro Ser Gln Leu Ser Ala Leu Arg Gly Trp Ile Lys Arg Asp Pro Ser
    770                 775                 780

His Leu Ser Asn Leu Ser Glu Leu Ile Leu Pro Thr Val Lys Glu Val
785                 790                 795                 800

Gln Gln Glu Asp Val Glu Ile Ile Gly Gly Leu Leu Ser Leu Arg Arg
                805                 810                 815

Leu Leu Ile Glu Ser Thr His Gln Thr Gln Arg Leu Leu Val Ile Arg
            820                 825                 830

Ala Asp Gly Phe Arg Cys Met Val Asp Phe Tyr Leu Asn Cys Gly Ser
        835                 840                 845

Ala Thr Gln Ile Met Phe Glu Ser Gly Ala Leu Pro Arg Ala Glu Glu
    850                 855                 860

Val Cys Phe Ser Leu Gly Val Arg Val Ala Lys Glu Asp Gly Asn Arg
865                 870                 875                 880

Gly Phe Asp Leu Gly Leu Gln Gly Asn Leu Leu Ser Leu Arg Arg Val
                885                 890                 895

Val Trp Val Lys Met Tyr Cys Gly Gly Ala Arg Val Gly Glu Ala Lys
            900                 905                 910

Glu Ala Lys Ala Ala Val Arg His Ala Leu Glu Asp His Pro Asn His
        915                 920                 925

Pro Pro Ile Gln Ile Asn Met Phe Pro Arg Ile Ala Glu Gly Ala Gln
```

```
                930              935              940
Asp Asp Asp Leu Met Cys Tyr Pro Val Gly Gly Pro Ile Ser Asp Ala
945              950              955              960

Glu
```

<210> SEQ ID NO 15
<211> LENGTH: 11
<212> TYPE: PRT
<213> ORGANISM: Artificial Sequence
<220> FEATURE:
<223> OTHER INFORMATION: Functional nuclear export signal NES from HIV
      Rev

<400> SEQUENCE: 15

```
Leu Gln Leu Pro Pro Leu Glu Arg Leu Thr Leu
1               5                   10
```

<210> SEQ ID NO 16
<211> LENGTH: 11
<212> TYPE: PRT
<213> ORGANISM: Artificial Sequence
<220> FEATURE:
<223> OTHER INFORMATION: Non-functional NES

<400> SEQUENCE: 16

```
Leu Gln Ala Pro Pro Ala Glu Arg Ala Thr Leu
1               5                   10
```

<210> SEQ ID NO 17
<211> LENGTH: 22
<212> TYPE: DNA
<213> ORGANISM: Artificial Sequence
<220> FEATURE:
<223> OTHER INFORMATION: Forward primer Sr50-F1, R1

<400> SEQUENCE: 17
tagcgctgct cacatccacc tc                                           22

<210> SEQ ID NO 18
<211> LENGTH: 23
<212> TYPE: DNA
<213> ORGANISM: Artificial Sequence
<220> FEATURE:
<223> OTHER INFORMATION: reverse primer Sr50-F1, R1

<400> SEQUENCE: 18
gatccgccgt tgtcggcatt tgt                                          23

<210> SEQ ID NO 19
<211> LENGTH: 27
<212> TYPE: DNA
<213> ORGANISM: Artificial Sequence
<220> FEATURE:
<223> OTHER INFORMATION: Forward primer Sr50-F2, R2

<400> SEQUENCE: 19
attcatgctt ttatactcac taatatc                                      27

<210> SEQ ID NO 20
<211> LENGTH: 19
<212> TYPE: DNA
<213> ORGANISM: Artificial Sequence
<220> FEATURE:
<223> OTHER INFORMATION: Reverse primer Sr50-F2, R2

<400> SEQUENCE: 20

```
gggcgtgact gtgctgctt                                                19

<210> SEQ ID NO 21
<211> LENGTH: 20
<212> TYPE: DNA
<213> ORGANISM: Artificial Sequence
<220> FEATURE:
<223> OTHER INFORMATION: Forward primer Sr50-F3

<400> SEQUENCE: 21
ttcagtgaag ttgccgctgt                                               20

<210> SEQ ID NO 22
<211> LENGTH: 20
<212> TYPE: DNA
<213> ORGANISM: Artificial Sequence
<220> FEATURE:
<223> OTHER INFORMATION: Forward primer ScRGA1-A-VIGS

<400> SEQUENCE: 22
cgacaactcc ggcagattta                                               20

<210> SEQ ID NO 23
<211> LENGTH: 25
<212> TYPE: DNA
<213> ORGANISM: Artificial Sequence
<220> FEATURE:
<223> OTHER INFORMATION: Reverse primer ScRGA1-A-VIGS

<400> SEQUENCE: 23
gacaaggatc gatagtaatt ggttc                                         25

<210> SEQ ID NO 24
<211> LENGTH: 24
<212> TYPE: DNA
<213> ORGANISM: Artificial Sequence
<220> FEATURE:
<223> OTHER INFORMATION: Forward primer ScRGA1-A RT-qPCR

<400> SEQUENCE: 24
tccacctaag gtaccttgat ctac                                          24

<210> SEQ ID NO 25
<211> LENGTH: 19
<212> TYPE: DNA
<213> ORGANISM: Artificial Sequence
<220> FEATURE:
<223> OTHER INFORMATION: Reverse primer ScRGA1-A RT-qPCR

<400> SEQUENCE: 25
gagttggaac caccttata                                                19

<210> SEQ ID NO 26
<211> LENGTH: 20
<212> TYPE: DNA
<213> ORGANISM: Artificial Sequence
<220> FEATURE:
<223> OTHER INFORMATION: Forward primer ScRGA1-A RT-PCR

<400> SEQUENCE: 26
gcgctgcctg gaataaggtc                                               20

<210> SEQ ID NO 27
<211> LENGTH: 21
<212> TYPE: DNA
```

```
<213> ORGANISM: Artificial Sequence
<220> FEATURE:
<223> OTHER INFORMATION: Reverse primer ScRGA1-A RT-PCR

<400> SEQUENCE: 27
taaaacaaag ccgcggaaaa c                                      21

<210> SEQ ID NO 28
<211> LENGTH: 27
<212> TYPE: DNA
<213> ORGANISM: Artificial Sequence
<220> FEATURE:
<223> OTHER INFORMATION: Forward primer RACE 5p,3p

<400> SEQUENCE: 28
gattcctgcc tttcttaaac aagccga                                27

<210> SEQ ID NO 29
<211> LENGTH: 21
<212> TYPE: DNA
<213> ORGANISM: Artificial Sequence
<220> FEATURE:
<223> OTHER INFORMATION: Reverse primer RACE 5p,3p

<400> SEQUENCE: 29
tcggcatgat gtctttgttc g                                      21

<210> SEQ ID NO 30
<211> LENGTH: 20
<212> TYPE: DNA
<213> ORGANISM: Artificial Sequence
<220> FEATURE:
<223> OTHER INFORMATION: Forward primer p2D7-F-end

<400> SEQUENCE: 30
ggcgggctgc tagtatttcc                                        20

<210> SEQ ID NO 31
<211> LENGTH: 20
<212> TYPE: DNA
<213> ORGANISM: Artificial Sequence
<220> FEATURE:
<223> OTHER INFORMATION: Reverse primer p2D7-F-end

<400> SEQUENCE: 31
gccatcggat ctggagagaa                                        20

<210> SEQ ID NO 32
<211> LENGTH: 22
<212> TYPE: DNA
<213> ORGANISM: Artificial Sequence
<220> FEATURE:
<223> OTHER INFORMATION: Forward primer p2D7-R-end

<400> SEQUENCE: 32
cgttgcaatg atgtaccata cg                                     22

<210> SEQ ID NO 33
<211> LENGTH: 19
<212> TYPE: DNA
<213> ORGANISM: Artificial Sequence
<220> FEATURE:
<223> OTHER INFORMATION: Reverse primer p2D7-R-end

<400> SEQUENCE: 33
accgagctcg tgtgctcaa                                         19
```

<210> SEQ ID NO 34
<211> LENGTH: 20
<212> TYPE: DNA
<213> ORGANISM: Artificial Sequence
<220> FEATURE:
<223> OTHER INFORMATION: Forward primer p2E7-F-end

<400> SEQUENCE: 34
caacaagacg cacaccacct                                               20

<210> SEQ ID NO 35
<211> LENGTH: 20
<212> TYPE: DNA
<213> ORGANISM: Artificial Sequence
<220> FEATURE:
<223> OTHER INFORMATION: Reverse primer p2E7-F-end

<400> SEQUENCE: 35
gtgcagttgc agaggacctg                                               20

<210> SEQ ID NO 36
<211> LENGTH: 20
<212> TYPE: DNA
<213> ORGANISM: Artificial Sequence
<220> FEATURE:
<223> OTHER INFORMATION: Forward primer p2C2-F-end

<400> SEQUENCE: 36
ttcgcaggtt catcatggtc                                               20

<210> SEQ ID NO 37
<211> LENGTH: 20
<212> TYPE: DNA
<213> ORGANISM: Artificial Sequence
<220> FEATURE:
<223> OTHER INFORMATION: Reverse primer p2C2-F-end

<400> SEQUENCE: 37
ctcccgaatt ggaaagtgga                                               20

<210> SEQ ID NO 38
<211> LENGTH: 20
<212> TYPE: DNA
<213> ORGANISM: Artificial Sequence
<220> FEATURE:
<223> OTHER INFORMATION: Forward primer p2C2-F-end

<400> SEQUENCE: 38
ccttggcctt tagcttgtgg                                               20

<210> SEQ ID NO 39
<211> LENGTH: 20
<212> TYPE: DNA
<213> ORGANISM: Artificial Sequence
<220> FEATURE:
<223> OTHER INFORMATION: Reverse primer p2C2-F-end

<400> SEQUENCE: 39
ttgccggaag caagaacttt                                               20

<210> SEQ ID NO 40
<211> LENGTH: 20
<212> TYPE: DNA
<213> ORGANISM: Artificial Sequence
<220> FEATURE:

<223> OTHER INFORMATION: Forward primer p1F7-F-end

<400> SEQUENCE: 40
cggagtgttt ggatgaaagg                                           20

<210> SEQ ID NO 41
<211> LENGTH: 20
<212> TYPE: DNA
<213> ORGANISM: Artificial Sequence
<220> FEATURE:
<223> OTHER INFORMATION: Reverse primer p1F7-F-end

<400> SEQUENCE: 41
ccgatccagg ggatataggt                                           20

<210> SEQ ID NO 42
<211> LENGTH: 20
<212> TYPE: DNA
<213> ORGANISM: Artificial Sequence
<220> FEATURE:
<223> OTHER INFORMATION: Forward primer p1F7-R-end

<400> SEQUENCE: 42
cttcgttagg aatggcaggt                                           20

<210> SEQ ID NO 43
<211> LENGTH: 20
<212> TYPE: DNA
<213> ORGANISM: Artificial Sequence
<220> FEATURE:
<223> OTHER INFORMATION: Reverse primer p1F7-R-end

<400> SEQUENCE: 43
catgcctgat tcaatgttgc                                           20

<210> SEQ ID NO 44
<211> LENGTH: 20
<212> TYPE: DNA
<213> ORGANISM: Artificial Sequence
<220> FEATURE:
<223> OTHER INFORMATION: Forward primer p2B8-F-end

<400> SEQUENCE: 44
gcacgcatgc atgtagttga                                           20

<210> SEQ ID NO 45
<211> LENGTH: 20
<212> TYPE: DNA
<213> ORGANISM: Artificial Sequence
<220> FEATURE:
<223> OTHER INFORMATION: Reverse primer p2B8-F-end

<400> SEQUENCE: 45
gggaagctcc tggtttgttg                                           20

<210> SEQ ID NO 46
<211> LENGTH: 20
<212> TYPE: DNA
<213> ORGANISM: Artificial Sequence
<220> FEATURE:
<223> OTHER INFORMATION: Forward primer p2B8-R-end

<400> SEQUENCE: 46
atccgtggga gctgtaggtg                                           20

```
<210> SEQ ID NO 47
<211> LENGTH: 20
<212> TYPE: DNA
<213> ORGANISM: Artificial Sequence
<220> FEATURE:
<223> OTHER INFORMATION: Reverse primer p2B8-R-end

<400> SEQUENCE: 47
agatggattg ggctgtggat                                               20

<210> SEQ ID NO 48
<211> LENGTH: 19
<212> TYPE: DNA
<213> ORGANISM: Artificial Sequence
<220> FEATURE:
<223> OTHER INFORMATION: Forward primer p2C8-F-end

<400> SEQUENCE: 48
cgctcagttt gccgaaaag                                                19

<210> SEQ ID NO 49
<211> LENGTH: 20
<212> TYPE: DNA
<213> ORGANISM: Artificial Sequence
<220> FEATURE:
<223> OTHER INFORMATION: Reverse primer p2C8-F-end

<400> SEQUENCE: 49
atcggagtcg tcggagagag                                               20

<210> SEQ ID NO 50
<211> LENGTH: 20
<212> TYPE: DNA
<213> ORGANISM: Artificial Sequence
<220> FEATURE:
<223> OTHER INFORMATION: Forward primer p2C8-R-end

<400> SEQUENCE: 50
ggtcccttgc tcgtgagttc                                               20

<210> SEQ ID NO 51
<211> LENGTH: 20
<212> TYPE: DNA
<213> ORGANISM: Artificial Sequence
<220> FEATURE:
<223> OTHER INFORMATION: Reverse primer p2C8-R-end

<400> SEQUENCE: 51
tgtgatggtg atgcttgtgc                                               20

<210> SEQ ID NO 52
<211> LENGTH: 21
<212> TYPE: DNA
<213> ORGANISM: Artificial Sequence
<220> FEATURE:
<223> OTHER INFORMATION: Forward primer p2C7-F-end

<400> SEQUENCE: 52
tctgaagccg gtcgagtctt c                                             21

<210> SEQ ID NO 53
<211> LENGTH: 21
<212> TYPE: DNA
<213> ORGANISM: Artificial Sequence
<220> FEATURE:
<223> OTHER INFORMATION: Reverse primer p2C7-F-end
```

```
<400> SEQUENCE: 53
gggagtacta gtctcgcatc a                                               21

<210> SEQ ID NO 54
<211> LENGTH: 20
<212> TYPE: DNA
<213> ORGANISM: Artificial Sequence
<220> FEATURE:
<223> OTHER INFORMATION: Forward primer p2C7-R-end

<400> SEQUENCE: 54
catggctgcc actctcaaag                                                 20

<210> SEQ ID NO 55
<211> LENGTH: 20
<212> TYPE: DNA
<213> ORGANISM: Artificial Sequence
<220> FEATURE:
<223> OTHER INFORMATION: Reverse primer p2C7-R-end

<400> SEQUENCE: 55
tcacgcacgt caagtcaaaa                                                 20

<210> SEQ ID NO 56
<211> LENGTH: 25
<212> TYPE: DNA
<213> ORGANISM: Artificial Sequence
<220> FEATURE:
<223> OTHER INFORMATION: Forward primer p2A3-F-end

<400> SEQUENCE: 56
tggtactgtg aaagcgattc ttatc                                           25

<210> SEQ ID NO 57
<211> LENGTH: 21
<212> TYPE: DNA
<213> ORGANISM: Artificial Sequence
<220> FEATURE:
<223> OTHER INFORMATION: Reverse primer p2A3-F-end

<400> SEQUENCE: 57
gacggcaaga tggagcaagg a                                               21

<210> SEQ ID NO 58
<211> LENGTH: 27
<212> TYPE: DNA
<213> ORGANISM: Artificial Sequence
<220> FEATURE:
<223> OTHER INFORMATION: Forward primer pIndigoBAC5

<400> SEQUENCE: 58
ggatgtgctg caaggcgatt aagttgg                                         27

<210> SEQ ID NO 59
<211> LENGTH: 26
<212> TYPE: DNA
<213> ORGANISM: Artificial Sequence
<220> FEATURE:
<223> OTHER INFORMATION: Reverse primer pIndigoBAC5

<400> SEQUENCE: 59
ctcgtatgtt gtgtggaatt gtgagc                                          26

<210> SEQ ID NO 60
<211> LENGTH: 23
```

```
<212> TYPE: DNA
<213> ORGANISM: Artificial sequence
<220> FEATURE:
<223> OTHER INFORMATION: synthetic sequence

<400> SEQUENCE: 60
ccaaatcatg ttgcttatcg gct                                        23
```